United States Patent [19]

McDonald et al.

[11] 4,275,738
[45] Jun. 30, 1981

[54] DIGITAL CARDIAC PACEMAKER CLOCKING MEANS

[75] Inventors: Ray S. McDonald, St. Paul; Martin A. Rossing, Anoka, both of Minn.

[73] Assignee: Medtronic, Inc., Minneapolis, Minn.

[21] Appl. No.: 958,322

[22] Filed: Nov. 6, 1978

[51] Int. Cl.³ .............................................. A61N 1/36
[52] U.S. Cl. .............................................. 128/419 PG
[58] Field of Search ................. 128/419 PG, 419 PS, 128/419 PT

[56] References Cited

U.S. PATENT DOCUMENTS

| | | | |
|---|---|---|---|
| 3,557,796 | 1/1971 | Keller, Jr. et al. | 128/419 PG |
| 4,095,603 | 6/1978 | Davies | 128/419 PT |
| 4,132,233 | 1/1979 | Hartlaub | 128/419 PG |

*Primary Examiner*—William E. Kamm
*Attorney, Agent, or Firm*—Joseph F. Breimayer

[57] ABSTRACT

A programmable cardiac pacemaker pulse generator utilizing digital circuitry for controlling the provision of cardiac stimulating pulses. The pulse generator is capable of having the rate, the pulse width, the pulse amplitude, the refractory period, the sensitivity and the mode of operation programmed. In addition, the pulse generator can have the output inhibited and can respond to programming signals causing a threshold margin test to be performed, effects of closure of the reed switch overridden, a hysteresis function added and a high rate exceeding the normal upper rate limit programmed. Many of the programmable functions of the pulse generator can either be programmed on a permanent or a temporary basis. The pulse generator further includes means for signaling the acceptance of a programming signal, and means to reset the program acceptance circuit if extraneous signals are detected as programming signals. The program signal acceptance circuit performs several different checks on the detected programming signal including a parity check, an access code check and determining if the proper number of signals were transmitted within a given time. The timing circuit of the pulse generator includes a crystal clock oscillator and counter means for counting the clock pulses therefrom to determine the rate of the pacemaker. The pulse width of each pacemaker pulse is determined by using a voltage controlled oscillator in place of the crystal oscillator to obtain energy compensation due to the battery voltage decreasing with time.

14 Claims, 40 Drawing Figures

| Fig.5A | Fig.5B | Fig.5C |
|---|---|---|

| Fig.6A | Fig.6C | Fig.6E | Fig.6G | Fig.6I | Fig.6K | Fig.6M |
|---|---|---|---|---|---|---|
| Fig.6B | Fig.6D | Fig.6F | Fig.6H | Fig.6J | Fig.6L | Fig.6N |

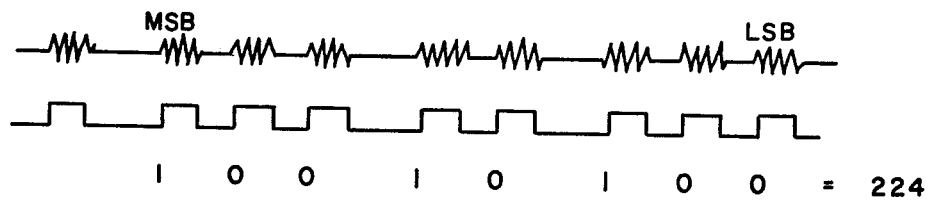
Fig.2
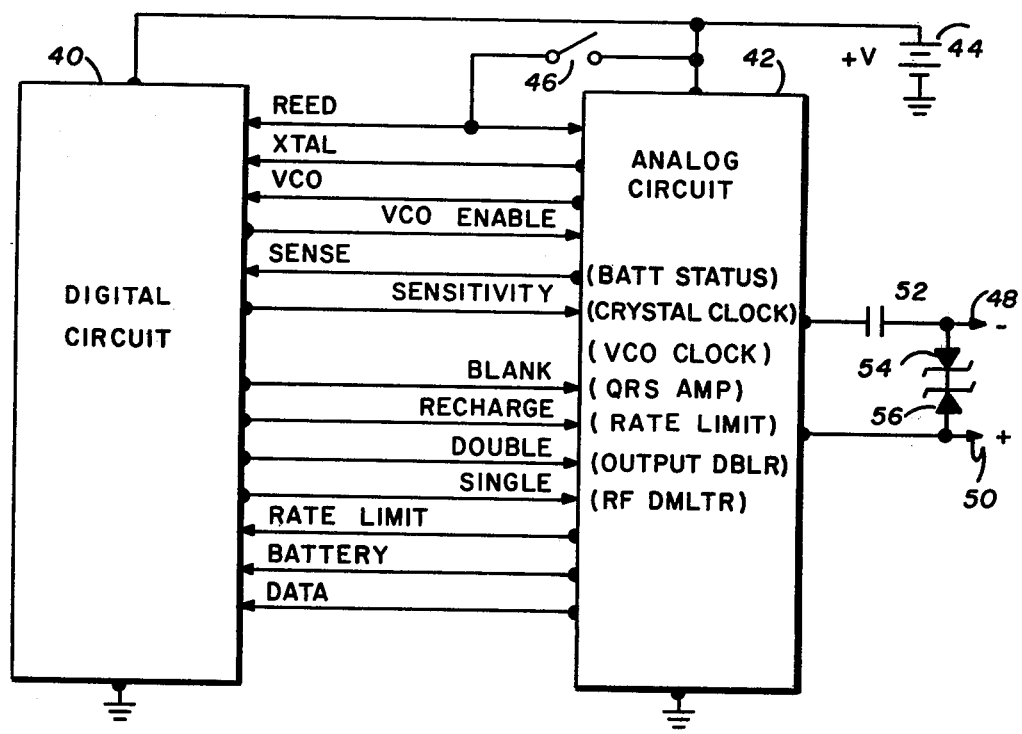

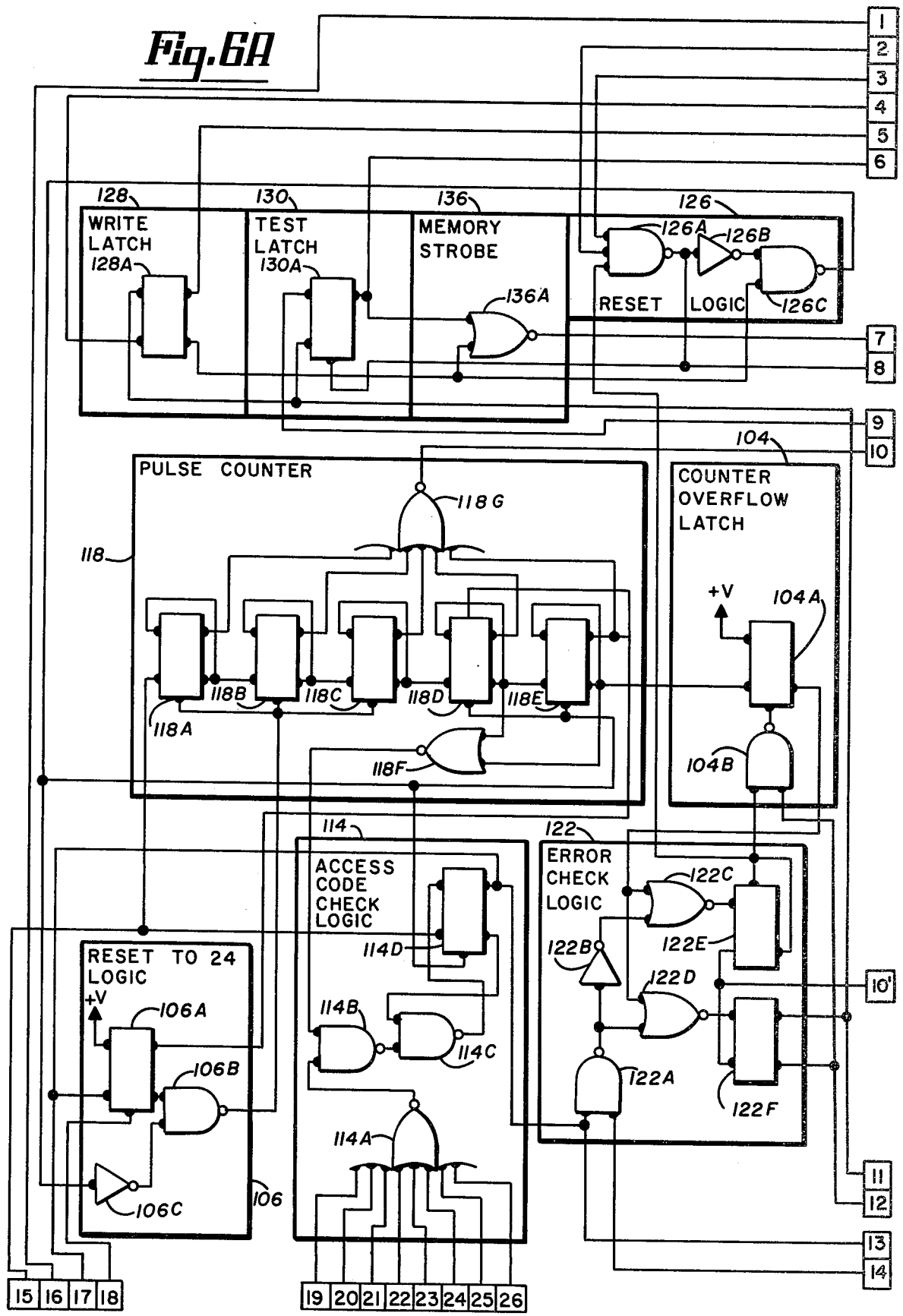

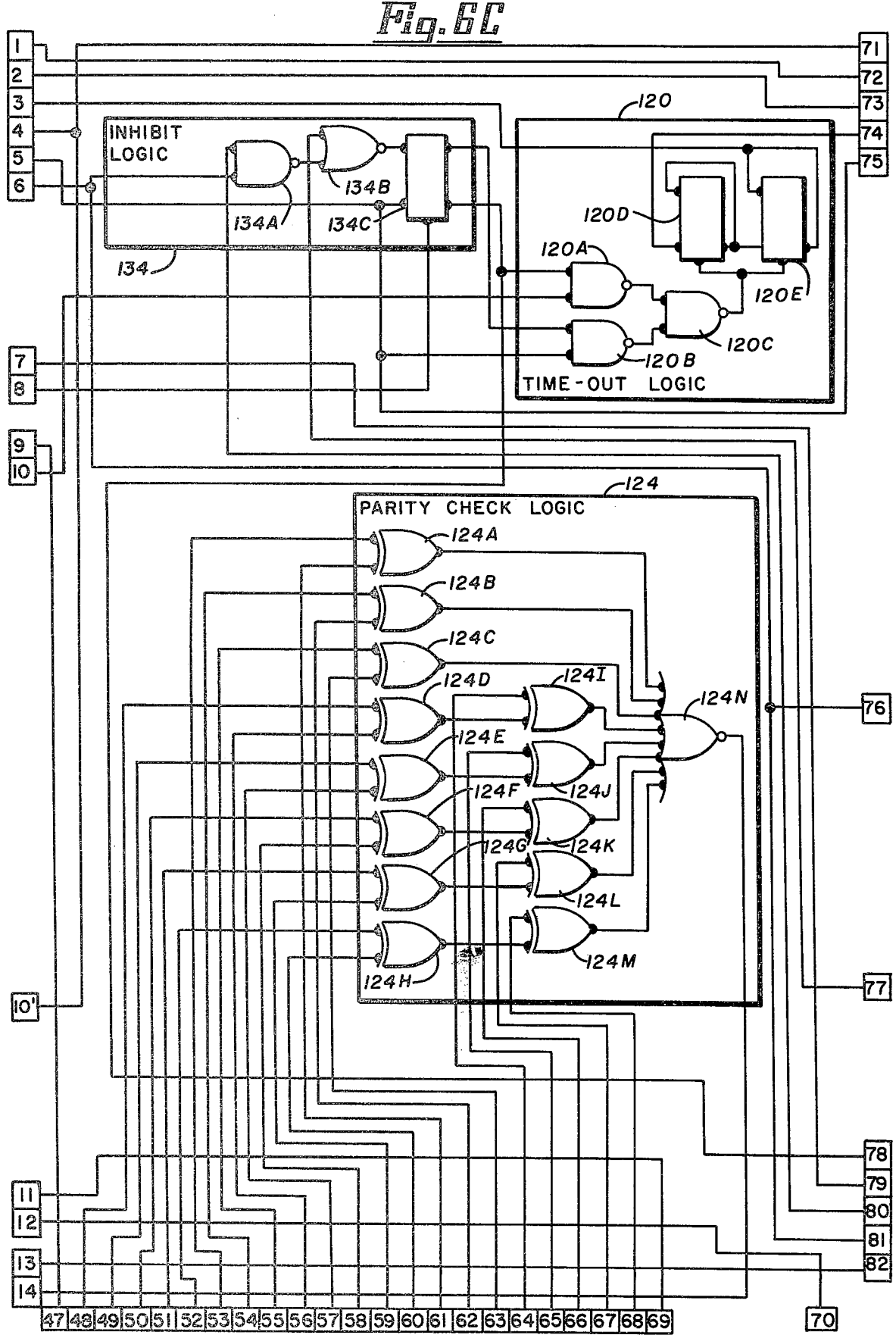

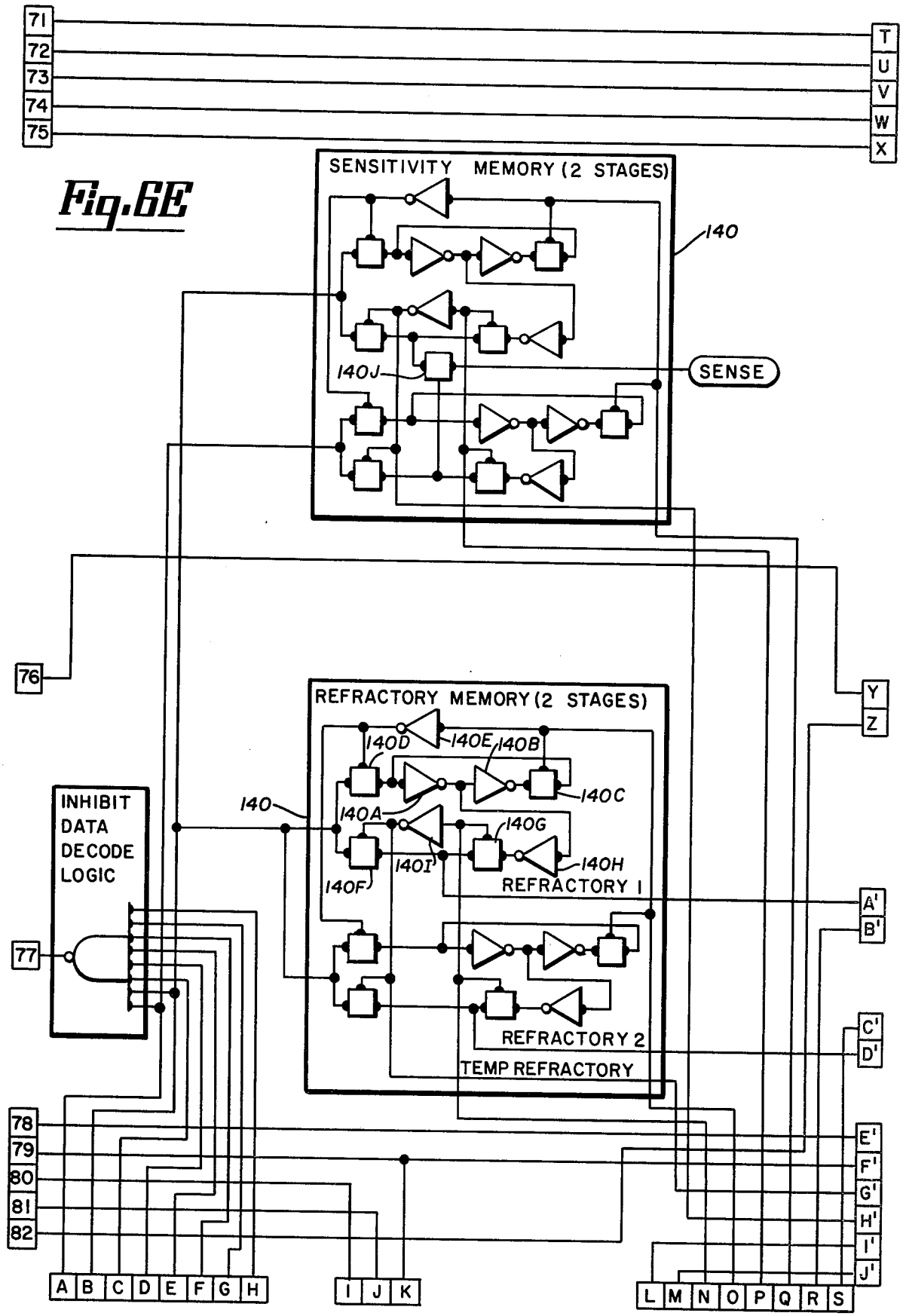

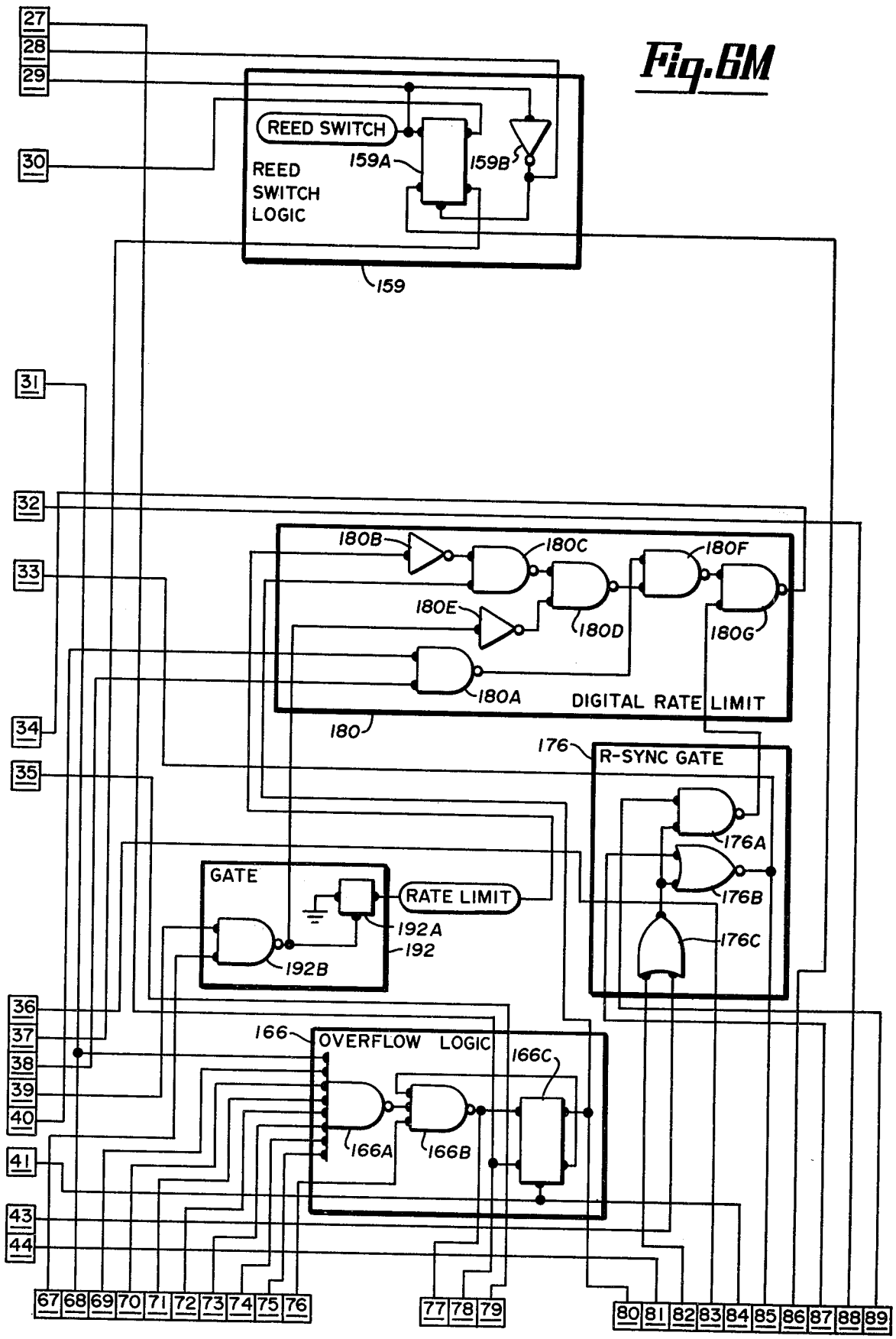

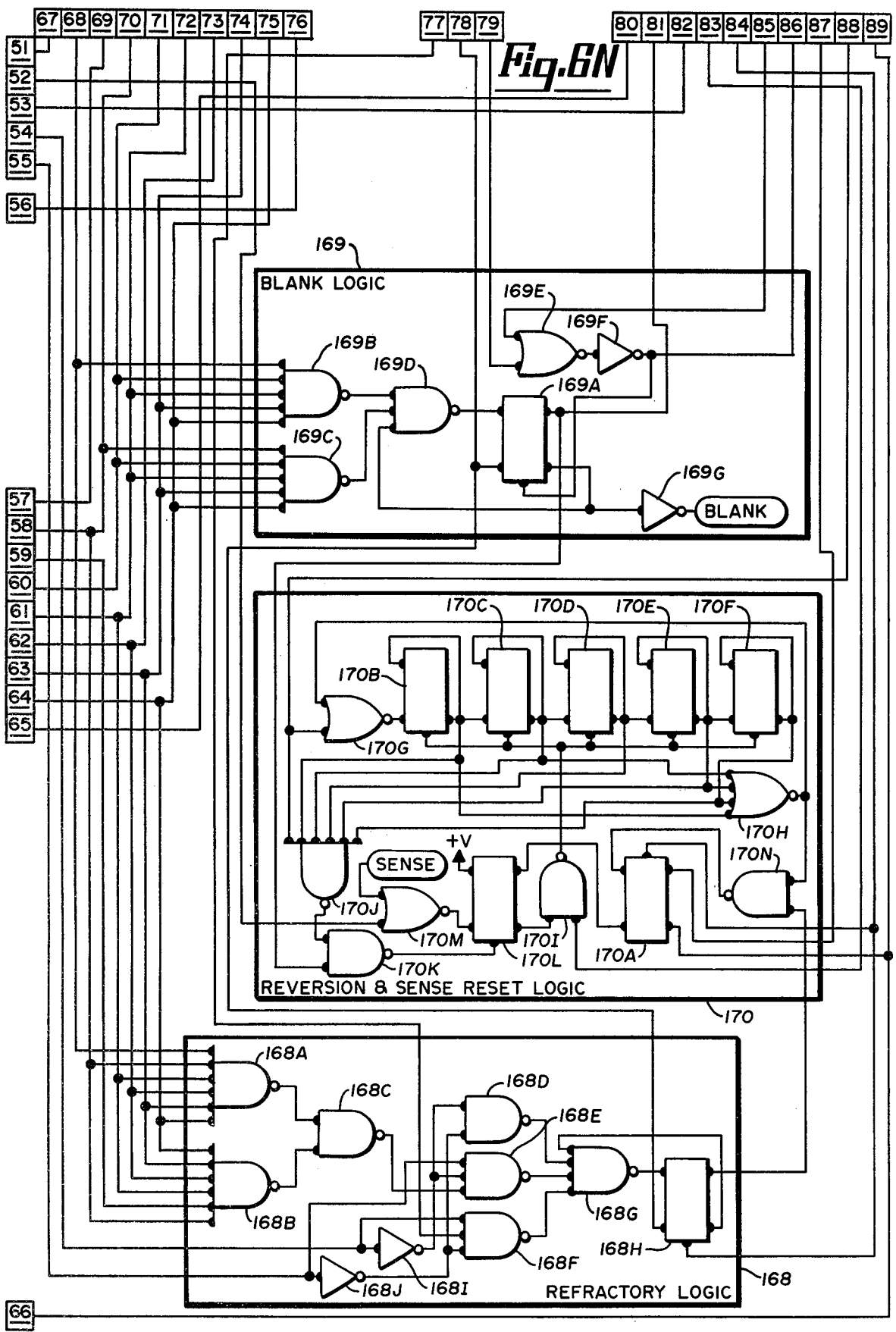

DIGITAL CARDIAC PACEMAKER CLOCKING MEANS

BACKGROUND OF THE INVENTION

1. Field of the Invention

This invention relates to medical devices and more particularly an implantable cardiac pacemaker capable of being programmed in a variety of different states.

2. Description of the Prior Art

The art of implantable cardiac pacemakers was first disclosed by Greatbatch in U.S. Pat. No. 3,057,356 entitled "Medical Cardiac Pacemaker", which issued in 1962. The device disclosed by Greatbatch included a relatively simple relaxation oscillator that generated electrical pulses at a fixed rate. These pulses were applied to the heart through a lead consisting of a conductor wire and an electrode to cause the heart to contract each time a pulse occurred. Since 1962, many improvements to cardiac pacemakers have occurred. These improvements include increased sophistication to the circuitry, including the inclusion of a sense amplifier to interact with the oscillator in providing stimulating pulses only when needed (the demand pacemaker), features to improve the reliability and longevity of pacemakers, improved packaging techniques, better power sources and improved leads and conductors.

Another improvement which has occurred since Greatbatch first disclosed the implantable cardiac pacemaker is means to allow the pacemaker to be reprogrammed after it has been implanted. In U.S. Pat. No. 3,805,796 in the name of Reese Terry, Jr. et al, entitled "Implantable Cardiac Pacer Having Adjustable Operating Parameters", which issued in 1974, circuitry is disclosed to allow the rate of the pacemaker to be noninvasively changed after it has been implanted. The rate varies in response to the number of times a magnetically operable reed switch is closed. The Terry et al device operates by counting the number of times the reed switch is closed and storing that count in a binary counter. Each stage of the counter is connected to either engage or bypass one resistor in a serially connected resistor chain, which chain is a part of the RC time constant controlling the pacemaker rate.

The concept of the Terry et al device has been improved upon by the apparatus shown in U.S. Pat. No. 4,066,086 in the name of John M. Adams et al, entitled "Programmable Body Stimulator", which issued in 1978, and which discloses a programmable cardiac pacemaker that responds to the application of radio frequency (RF) pulse bursts while a magnetic field held in close proximity to a magnetically operated reed switch included within the pacemaker package holds the reed switch closed. In the Adams et al circuit, again only the rate is programmable in response to the number of RF pulse bursts applied. The use of radio frequency signals to program cardiac pacemaker was first disclosed by Wingrove in the U.S. Pat. No. 3,833,005 entitled "Compared Count Digitally Controlled Pacemaker" which issued in 1974. The Wingrove device was capable of having both the rate and pulse width programmed. However, no pacemaker has ever been described which is capable of having more than two parameters programmed or selected features or tests programmed on command. Such a pacemaker could be called a universally programmable pacemaker.

One area where cardiac pacing technology has lagged behind conventional state of electronic technology involves utilization of digital electrical circuits. One reason for this has been the high energy required to operate digital electronic circuits. However, with more recent technology advances in complimentary metal oxide semiconductor (CMOS) devices fabricated on large scale integrated circuits, together with the improvements of cardiac pacemaker batteries, digital electronic circuits are beginning to be utilized in commercial pacemakers. The inherent advantages of digital circuits are their accuracy, and reliability. Typically, the digital circuit is operated in response to a crystal oscillator which provides a very stable frequency over extended periods of time. There have been suggestions in the prior art for utilizing digital techniques in cardiac stimulators and pacemakers since at least 1966. For instance, see the article by Leo F. Walsh and E. Neil Moore, entitled "Digital Timing Unit for Programming Biological Stimulators" in *The American Journal of Medical Electronics*, First Quarter, 1966, Pages 29 through 34. The first patent suggesting digital techniques is U.S. Pat. No. 3,557,796 in the name of John W. Keller, Jr., et al, and is entitled "Digital Counter Driven Pacer", which issued in 1971. This patent discloses an oscillator driving a binary counter. When the counter reaches a certain count, a signal is provided which causes a cardiac stimulator pulse to be provided. At the same time the counter is reset and again begins counting the oscillator pulses. Additionally, in the Keller et al patent, there is disclosed the digital demand concept, in which the counter is reset upon the sensing of a natural heartbeat, and the digital refractory concept, in which the output is inhibited for any certain time after the provision of a cardiac stimulating pulse or the sensing of a natural beat.

As mentioned above, digital programming techniques are shown in both the Terry et al U.S. Pat. No. 3,805,796 and the Wingrove U.S. Pat. No. 3,833,005. Wingrove additionally discloses digital control circuitry for controlling the rate of the stimulating pulses by providing a resettable counter to continually count up to a certain value that is compared against a value programmed into a storage register. The Wingrove patent also shows provisions for adjusting the output pulse width by switching the resistance in the RC circuit which controls the pulse width.

Other patents disclosing digital techniques useful in cardiac pacing include U.S. Pat. No. 3,631,860 in the name of Michael Lopin entitled "Variable Rate Pacemaker, Counter-Controlled, Variable Rate Pacer"; No. 3,857,399 in the name of Fred Zacouto entitled "Heart Pacer"; 3,865,119 in the name of Bengt Svensson and Gunnar Wallin entitled "Heartbeat Accentuated with Controlled Pulse Amplitude"; No. 3,870,050 in the name of Wilson Greatbatch entitled "Demand Pacer"; No. 4,038,991 in the name of Robert A. Walters entitled "Cardiac Pacer with Rate Limiting Means"; No. 4,043,347 in the name of Alexis M. Renirie entitled "Multiple-Function Demand Pacer with Low Current Drain"; No. 4,049,003 in the name of Robert A. Walters et al entitled "Digital Cardiac Pacer"; No. 4,049,004 in the name of Robert A. Walters entitled "Implantable Digital Cardiac Pacer Having Externally Selectable Operating Parameters and One Shot Digital Pulse Generator for Use Therein"; and No. 4,074,720 in the name of Franklin I. Malchman et al entitled "Cardiac Pacer with Rate Runaway Protection".

SUMMARY OF THE INVENTION

The prior art teaches utilizing a fixed frequency clock and counter to control the rate of a cardiac pacemaker. The clock provides pulses to be counted by the counter and when the counter reaches a certain count, a cardiac stimulating pulse is provided. Once the rate is determined additional means such as a resistor-capacitor timing circuit are utilized by the prior art devices to control the width of the stimulating pulses. It would be advantageous to eliminate the resistor-capacitor circuit of the prior art by utilizing the same counter to control pulse width as well as rate. One manner of accomplishing this would be to continue the count of the counter once the rate count is reached. However, in some instances, such as with rate programmable pacemakers, the rate count of the counter will change and one cannot know what the higher count will be to obtain a specific pulse width for a variety of rates. In other situations, such as where the pulse width is programmable as well as the rate, or where it is desirable to provide a diffrequency clock signal when determining the pulse width it also is not advantageous to utilize the technique of continuing to increment the counter upwards after the rate count is reached. It would be preferable to reset the counter to an initial count as soon as it reaches the rate count and again begin incrementing the counter until a certain pulse width count is reached.

In accordance with one aspect of this invention, there is provided a cardiac pacemaker pulse generator comprising clock means for providing a series of clock pulses and counter means for counting the clock pulses. Additionally, there is provided logic means responsive to the counter reaching a first count for causing a cardiac stimulating pulse to be provided and for resetting the counter means and further responsive to counter means reaching a second count less than the first count at a time after the stimulating pulse is provided for terminating the provision of the stimulating pulse.

BRIEF DESCRIPTION OF THE DRAWINGS

There is hereafter described one preferred embodiment of the subject invention with reference being made to the following Figures in which:

FIG. 2 shows the type of code provided from the programmer to the pulse generator;

FIG. 3 shows in block format, one programming word and the various portions thereof;

FIG. 4 shows an interconnect diagram between the digital and analog circuit portions of the present embodiment and the various signals provided between these two portions;

DESCRIPTION OF THE PREFERRED EMBODIMENTS

Figures 1, 5, 6:
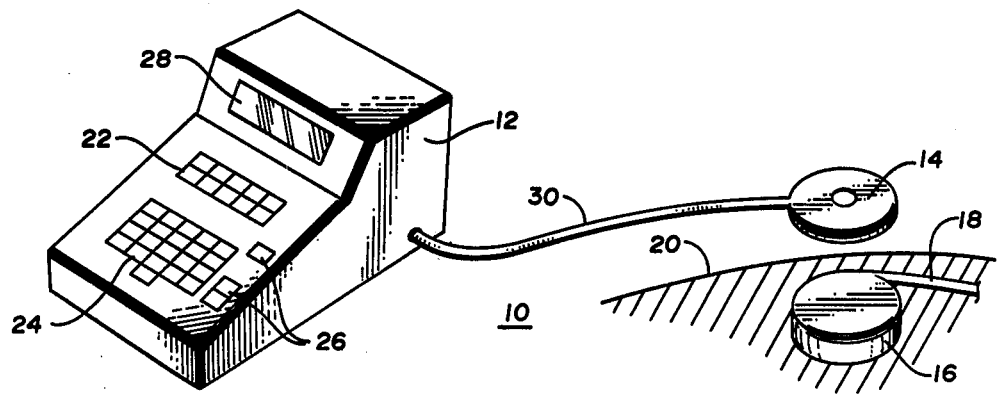
FIG. 1 shows the entire system of a programmer and implanted cardiac pacemaker pulse generator.
FIG. 5 shows the arrangement of FIGS. 5A, 5B and 5C, which in turn show, in block format, the digital circuitry portion of the subject invention.
FIG. 6 shows the arrangement of FIGS. 6A through 6N, which in turn show a more detailed circuit diagram, the digital circuitry of the subject invention.

Referring now to FIG. 1, the entire programmable pacemaker system 10 is shown and includes the programmer 12, programming head 14, and the pulse generator 16. Signals generated by pulse generator 16 are applied through leads 18 to the heart (not shown) to cause the contraction thereof. The type of signals applied from pulse generator 16 through leads 18, as well as the response of the heart to these signals, is well known in the art and will not be discussed herein.

It should be noted, however, that in the embodiment described herein, pulse generator 16 is of the implantable type and as such is placed beneath the surface of the skin 20. However, nothing herein should be construed as limiting the inventions described herein as pertaining solely to implantable type pulse generators.

Programmer 12 may be any type of radio frequency (RF) burst signal generator which is designed to provide a train of radio frequency signals of the type hereafter described with respect to FIGS. 2 and 3. Programmer 12 includes the plurality of operator depressable keys on its face. These keys include parameter keys 22, numeric keys 24, and funtion keys 26. In addition, a display 28 is included so that the operator can view a display of the depressed keys.

In order to program pulse generator 16, selected parameter, numeric and function keys are depressed. The parameter keys include keys for programming the rate, pulse width and magnitude of the cardiac stimulating pulse, the sensitivity of the amplifier, the refractory period, as well as causing pulse generator 16 to operate with or without a hysteresis function, or either in the ventricular-synchronous (R-sync) or the ventricular-inhibited (demand) mode, or either in the asynchronous or demand mode. Additionally, there are parameter keys to cause a threshold check to be performed and to inhibit the operation of pulse generator 16.

Numeric keys 24 are depressed to cause the programmer 12 to generate signals manifesting a particular value to which the selected parameter is to be programmed. For instance, if the rate parameter button 22 is depressed, it is necessary to depress keys manifesting the desired value of rate on the numeric keys 24.

Function keys 26 are utilized to cause programmer 12 to program pulse generator 16 either permanently or temporarily. In addition, one of the function keys is utilized when inhibiting pulse generator 13 in a manner such that it must be maintained depressed to cause continuous inhibit programming signals to be sent from programmer 12 through head 14 to pulse generator 16 in order to maintain the inhibited condition.

In order to program pulse generator 16, it is necessary that head 14 be placed at an appropriate position directly above pulse generator 16 and that a series of radio frequency burst signals be applied from programmer 12 through wire 30 to head 14. Head 14 includes a permanent magnet of sufficient size to cause a magnetically actuated reed switch within pulse generator 16 to be closed. The closure of the reed switch in pulse generator 16 allows circuitry within pulse generator 16 to detect and process the RF signals applied over wire 30 to head 14.

Referring now to FIGS. 2 and 3, the type of data generated by programmer 12 will be described. Each different programming operation requires the transmission by programmer 12 of a thirty-two binary digit (bit) word with each bit being either a logic "1" or a logic "0" binary number. The actual signals generated by programmer 12 are bursts of radio frequency signals at a frequency of approximately 175 kilohertz. For each word to be generated by programmer 12, thirty-three virtually identical RF bursts are applied. Each bit is in turn defined by the real time separation between successive RF bursts. In the preferred embodiment described herein a relatively long time will be defined as a logic "1" bit and a relatively short time will be defined as a logic "0" bit. The pulse burst duration may be approximately 0.35 msec, the relatively long time may be approximately 2.2 msec and the relatively short time may be approximately 1.0 msec. Thus, for example, as shown in FIG. 2, an arbitrary series of nine RF bursts are shown in the upper graph. These nine bursts have been processed into pulses by RF demodulation circuitry within pulse generator 16 and are seen as a series of pulses in the lower graph of FIG. 2. Beneath the lower graph of FIG. 2 is a series of eight binary numbers placed at the beginning of each of the second through ninth pulses. Each of these numbers represent the bit manifested by the duration between that pulse burst and the one preceding it. Thus, for the signal shown in the upper graph of FIG. 2, the binary code would be "10010100". This binary number can be written in an octal number system as "224" in a conventional manner. The first number of the octal number represents the first two most significant bits, the middle number of the octal number represents the next three bits and the last number of the octal number represents the last three least significant bits. Hereafter for convenience, all programming codes will be manifested in the octal number system.

Referring to FIG. 3, the thirty-two bit words generated by programmer 12 to pulse generator 16 will be described. The thirty-two bit words consist of four parts, each of which is eight bits in length. These four parts are parameter code, data code, access code and parity code and are generated in that order, least significant bit first. The first three bits of the eight bit parameter code are not used whatsoever and are always generated as logic "0" bits. The fourth bit of the parameter code is either a logic "1" or a logic "0" bit, which respectively manifests either a temporary or permanent programming command and the last four of the parameter bits represent the code for the particular one of the function keys 26 depressed by the operator in operating programmer 12.

The data code portion of the programming word consists of eight bits which define a particular value for the parameter selected.

Following the data portion of the programming word is the eight bit access word which always consists of the octal code "227". This word, as will be explained hereafter with respect to FIGS. 5 and 6, is utilized to start the process of programming pulse generator 16. One purpose for the access word is to prevent extraneous signals which may be detected by pulse generator 16 from causing a reprogramming.

The final eight bit portion of the programming words consists of an eight bit parity code which is generated to provide proper vertical parity based on the parameter and data portions of the word. Again the parity portion is used as a check to prevent extraneous or undesirable programming of pulse generator 16.

Referring to FIG. 4, an interconnect diagram between the digital and analog circuitry included in pulse generator 16 is shown. In general, the analog circuit 42 consists of various separate electrical systems. These systems include a battery monitor, a crystal clock, a voltage control oscillator clock, a QRS sensing amplifier, output circuitry including rate limit circuitry and a voltage doubler, and an RF demodulator. Each of these analog systems are well known in the art and will not be described in structural detail herein. However, for a complete description of certain of these circuits, reference is made to the following patent applications, filed even date herewith: Ser. No. 957,812, entitled "Demand Cardiac Pacemaker Having Reduced Polarity Disparity" invented by Jerome T. Hartlaub and Ray S. McDonald, and Ser. No. 957,828 entitled "Cardiac Pacemaker Having A Rate Limit" invented by David L. Thompson, Yong Sang Lee and Ray S. McDonald.

The digital circuit 40 includes all of the digital logic necessary to cause a programming change, memory to store the digital code manifesting the desired values for the programmed parameters and digital timing means for causing pulses to be generated from pulse generator 16 in the programmed manner. A more detailed description of digital circuit 40 is given in FIGS. 5A, 5B and 5C and still more detailed description is given with respect to FIGS. 6A through 6N.

The electrical interconnect diagram shown in FIG. 4 also shows battery 44, which may be a conventional lithium-iodide battery generating +V, or approximately 2.8, volts, connected between a source of reference potential, such as ground, and each of the digital and analog circuits 40 and 42. In addition, each of digital and analog circuits 40 and 42 are connected to ground.

A magnetic field actuated reed relay switch 46 is connected between the positive side of battery 44 and each of digital and analog circuits 40 and 42 respectively. Two outputs, 48 and 50, are provided from analog circuit 42 and these represent signals applied to the conventional lead as used with a cardiac pacemaker. Output 50 may consist only of the outer metal casing of the pulse generator 16 or it may be a second wire within the lead system, depending on the type of leads selected. Output 48 is coupled through a capacitor 52 to analog circuit 42 and to the heart (not shown). In addition, a pair of diodes 54 and 56 having their anodes coupled together and their cathodes coupled to outputs 48 and 50 respectively are provided. Diodes 54 and 56 in the presence of large extraneous signals such as are caused by electrocautery function in a conventional manner to prevent damage to circuitry included in pulse generator 16.

Whenever reed switch 46 is closed as a result of a magnet, such as is included in head 14, being placed in close proximity with pulse generator 16, a +V volts, or a logic "1" REED signal, is applied to both digital circuit 40 and analog circuit 42. When head 14 is removed reed switch 46 opens and a ground, or logic "0" signal is applied to digital circuit 40 and analog circuit 42. Analog circuit 42 provides the XTAL, VCO, SENSE, RATE LIMIT, BATTERY and DATA signals to digital circuit 40. Digital circuit 40 provides the VCO ENABLE, SENSITIVITY, BLANK, RECHARGE, DOUBLE, and SINGLE signals to analog circuit 42.

As mentioned above, the REED signal is a logic "1" whenever reed switch 46 is closed and a logic "0" whenever reed switch 46 is open, as normally would be the case. The XTAL signal is a generally square wave pulse signal occurring at a frequency of 32,768 hertz and the VCO signal is a square wave pulse signal having a frequency of 40,000 hertz whenever the voltage of battery 44 is equal to 2.8 volts. As the voltage of battery 44 decreases with time, the frequency of the VCO signal will also decrease according to the formula $F_{VCO} = 5.92 \times (V - 0.2)^2$ where V is the actual voltage provided by battery 44. As will be explained hereafter, the VCO signal used in providing timing to determine the exact width of the pulse provided by pulse generator 16. In order to maintain a constant energy of the pulse, it is necessary that the pulse increase in width as the voltage from battery 44 decreases. Thus, a VCO, which provides the decreasing frequency with decreasing voltage, is utilized.

The VCO ENABLE signal provided from digital circuit 40 to analog circuit 42 is normally logic "1". However, at the time the stimulating pulse is to be provided, the VCO ENABLE signal becomes logic "0" and the VCO is enabled to begin providing pulses. The VCO ENABLE signal remains logic "0" until after the stimulating pulse has been provided, at which time it returns to logic "1" and the VCO becomes disabled.

The SENSE signal is provided from the output of the sense amplifier as a normally logic "1" signal which becomes a logic "0" pulse signal each time the sense amplifier senses a naturally occurring QRS signal. The SENSITIVITY signal is a three state digital signal which may be logic "1", logic "0" or floating and is provided directly from the memory included in digital circuit 40. The state of the SENSITIVITY signal indicates the sensitivity that the sense amplifier is to assume.

The BLANK signal provided from digital circuit 40 is a normally logic "1" signal which becomes logic "0" for approximately 100 msec following the provision of a stimulating pulse from pulse generator 16 or the sensing of a natural QRS complex. The BLANK signal is used to prevent the sense amplifier within analog circuit 42 from sensing any signals during the 100 msec time interval and to allow the components within the sensing amplifier to reset themselves after sensing a signal.

The RECHARGE signal is a normally logic "0" pulse signal which becomes logic "1" for approximately 7.8 msec after the stimulating pulse has been provided or a natural QRS complex sensed. The purpose of the RECHARGE signal is to open a switch and allow a capacitor in the voltage doubler portion of analog circuit 42 to become quickly recharged. The DOUBLE signal and the SINGLE signal provided from digital circuit 40 to analog circuit 42 respectively cause either a stimulation pulse, having a magnitude of twice the value of the voltage provided by battery 44 or a stimulation pulse having a magnitude equal to the value of the voltage provided by battery 44 to be provided between outputs 48 and 50. Further, the DOUBLE or SINGLE signals are pulses having a pulse width equal to the desired pulse width of the stimulating signal to be provided between outputs 48 and 50.

The RATE LIMIT signal provided from analog circuit 42 to digital circuit 40 is a normally logic "0" signal which becomes logic "1" after the provision of the stimulation pulse for 462 msec to set an upper rate limit of 130 pulses per minute for pulse generator 16. The BATTERY signal applied from analog circuit 42 to digital circuit 40 is a logic "1" signal as long as the voltage provided from battery 44 is above a certain minimum level of, for instance, 2.0 volts and is a logic "0" signal whenever the voltage from battery 44 falls below 2.0 volts.

The DATA signal from analog circuit 42 to digital circuit 40 is a pulse signal going from logic "0" to logic "1", similar to that shown in the lower graph of FIG. 2, that is, the signal is at a logic "1" level whenever a pulse burst is being provided by programmer 12 and at a logic "0" level between the time pulse bursts are provided. As mentioned above, each time pulse generator 16 is programmed, 33 pulses, defining 32 bits, are applied from the analog circuit 42 over the DATA line to digital circuit 40. These pulses are provided from the RF demodulator portion of analog circuit 42 in a known manner.

The parameter portion of the DATA signal defines one of eleven parameters to be modified and whether that modification is to be in a temporary or permanent manner, if that choice is available. The eleven parameters are inhibit, refractory, hysteresis operation, asynchronous/demand operation, pulse width, high rate, threshold check, normal rate, R-sync/demand operation, sensitivity and output voltage value. Of the above eleven parameters, the inhibit, high rate, and threshold check parameters can only be done in a temporary mode and hysteresis can only be done in the permanent mode. All of the others can either be permanent or temporary. As will be described hereafter in more detail, the temporary mode of programming causes pulse generator 16 to be programmed for as long as head 14 is positioned over pulse generator 16 to maintain the reed switch 46 closed or until another programming word is provided. Upon the opening of reed switch 46 or the transmission of another programming word, the original conditions programmed into pulse generator 16 will again control unless, of course, the new programming word modifies that condition.

Reference Table I set out below indicates the eleven different parameters which can be varied and for each the parameter code for either a temporary parameter change or for a permanent parameter change, and the different data values which can be selected and the code which should be included in the data portion of programming signal to accomplish that data change. It should be noted that all temporary and permanent parameter codes and data codes are in the octal number system to conveniently manifest an eight bit binary number with 3 digits. It also should be noted that numbers in the data value column are decimal numbers.

TABLE I

| PROGRAMMING PARAMETER CODES AND VALUE CODES | | | | |
| --- | --- | --- | --- | --- |
| PARAMETER | TEMP. CODE | PERM. CODE | DATA VALUE | DATA CODE |
| INHIBIT | 010 | — | Always | 377 |
| REFRACTORY | 030 | 020 | 220 msec | 000 |
| | | | 325 msec | 001 |
| | | | 400 msec | 002 |
| | | | Asynchronous | 003 |
| HYSTERESIS | — | 060 | No Hysteresis | 000 |
| | | | 40 BPM Lower Limit | 001 |
| | | | 50 BPM Lower Limit | 002 |
| | | | 60 BPM Lower Limit | 003 |
| ASYN./DEMAND | 110 | 100 | Demand Mode | 000 |
| | | | Asynchronous Mode | 001 |
| PULSE WIDTH | 130 | 120 | 50 Microsecond BOL | 000 |

TABLE I-continued
PROGRAMMING PARAMETER CODES AND VALUE CODES

| PARAMETER | TEMP. CODE | PERM. CODE | DATA VALUE | DATA CODE |
|---|---|---|---|---|
| | | | 100 Microsecond BOL | 001 |
| | | | 150 Microsecond BOL | 002 |
| | | | 200 Microsecond BOL | 003 |
| | | | 250 Microsecond BOL | 004 |
| | | | . | . |
| | | | 3150 Microsecond BOL | 076 |
| | | | 3200 Microsecond BOL | 077 |
| HIGH RATE | 170 | — | 150 nominal (149.4 actual) | 000 |
| | | | 155 (155.5) PPM | 376 |
| | | | 160 (158.7) PPM | 375 |
| | | | 165 (165.6) PPM | 373 |
| | | | 170 (169.3) PPM | 372 |
| | | | 175 (173.2) PPM | 371 |
| | | | 180 (181.4) PPM | 367 |
| | | | 185 (185.8) PPM | 367 |
| | | | 190 (190.5) PPM | 365 |
| | | | 195 (195.4) PPM | 364 |
| | | | 200 (200.5) PPM | 363 |
| | | | 205 (205.9) PPM | 362 |
| | | | 210 (211.6) PPM | 361 |
| | | | 215 (217.7) PPM | 360 |
| | | | 220 (217.7) PPM | 360 |
| | | | 225 (224.1) PPM | 357 |
| | | | 230 (230.9) PPM | 356 |
| | | | 235 (238.1) PPM | 355 |
| | | | 240 (238.1) PPM | 355 |
| | | | 245 (245.8) PPM | 354 |
| | | | 250 (254.0) PPM | 353 |
| | | | 260 (262.0) PPM | 352 |
| | | | 270 (272.1) PPM | 351 |
| | | | 280 (282.2) PPM | 350 |
| | | | 290 (293.0) PPM | 347 |
| | | | 300 (304.7) PPM | 346 |
| | | | 310 (304.7) PPM | 346 |
| | | | 320 (317.4) PPM | 345 |
| | | | 330 (331.2) PPM | 344 |
| | | | 340 (346.3) PPM | 343 |
| | | | 360 (362.8) PPM | 342 |
| | | | 380 (380.9) PPM | 341 |
| | | | 400 (400.9) PPM | 340 |
| THRESHOLD CHECK | 210 | — | 50 Microsecond BOL | 000 |
| | | | 100 Microsecond BOL | 001 |
| | | | 150 Microsecond BOL | 002 |
| | | | 200 Microsecond BOL | 003 |
| | | | 250 Microsecond BOL | 004 |
| | | | . | . |
| | | | 3150 Microsecond BOL | 076 |
| | | | 3200 Microsecond BOL | 077 |
| RATE | 230 | 220 | 30 (30.0) | 313 |
| | | | 31 (31.0) | 303 |
| | | | 32 (32.0) | 273 |
| | | | 33 (33.0) | 264 |
| | | | 34 (34.0) | 255 |
| | | | 35 (35.0) | 247 |
| | | | 36 (35.9) | 241 |
| | | | 37 (37.0) | 233 |
| | | | 38 (37.9) | 226 |
| | | | 39 (39.1) | 220 |
| | | | 40 (39.9) | 214 |
| | | | 41 (41.0) | 207 |
| | | | 42 (42.1) | 202 |
| | | | 43 (43.0) | 176 |
| | | | 44 (44.0) | 172 |
| | | | 45 (45.1) | 166 |
| | | | 46 (45.9) | 163 |
| | | | 47 (47.0) | 157 |
| | | | 48 (47.9) | 154 |
| | | | 49 (48.9) | 151 |
| | | | 50 (50.1) | 145 |
| | | | 51 (51.1) | 142 |
| | | | 52 (51.8) | 140 |
| | | | 53 (52.9) | 135 |
| | | | 54 (54.0) | 132 |
| | | | 55 (54.8) | 130 |

TABLE I-continued
PROGRAMMING PARAMETER CODES AND VALUE CODES

| PARAMETER | TEMP. CODE | PERM. CODE | DATA VALUE | DATA CODE |
|---|---|---|---|---|
| | | | 56 (56.0) | 125 |
| | | | 57 (56.9) | 123 |
| | | | 58 (58.2) | 120 |
| | | | 59 (59.1) | 116 |
| | | | 60 (60.0) | 114 |
| | | | 61 (61.0) | 112 |
| | | | 62 (62.0) | 110 |
| | | | 63 (63.0) | 106 |
| | | | 64 (64.0) | 104 |
| | | | 65 (65.1) | 102 |
| | | | 66 (66.3) | 100 |
| | | | 67 (66.8) | 077 |
| | | | 68 (68.0) | 075 |
| | | | 69 (69.3) | 073 |
| | | | 70 (69.9) | 072 |
| | | | 71 (71.2) | 070 |
| | | | 72 (71.9) | 067 |
| | | | 73 (73.3) | 065 |
| | | | 74 (74.0) | 064 |
| | | | 75 (74.7) | 063 |
| | | | 76 (76.2) | 061 |
| | | | 77 (77.0) | 060 |
| | | | 78 (77.8) | 057 |
| | | | 79 (79.4) | 055 |
| | | | 80 (80.2) | 054 |
| | | | 81 (81.1) | 053 |
| | | | 82 (81.9) | 052 |
| | | | 83 (82.8) | 051 |
| | | | 84 (83.7) | 050 |
| | | | 85 (84.7) | 047 |
| | | | 86 (85.6) | 046 |
| | | | 87 (86.6) | 045 |
| | | | 88 (87.6) | 044 |
| | | | 89 (88.6) | 043 |
| | | | 90 (89.7) | 042 |
| | | | 91 (90.7) | 041 |
| | | | 92 (91.8) | 040 |
| | | | 93 (92.9) | 037 |
| | | | 94 (94.1) | 036 |
| | | | 95 (95.3) | 035 |
| | | | 96 (96.5) | 034 |
| | | | 97 (96.5) | 034 |
| | | | 98 (97.7) | 033 |
| | | | 99 (99.0) | 032 |
| | | | 100 (100.3) | 031 |
| | | | 101 (101.6) | 030 |
| | | | 102 (101.6) | 030 |
| | | | 103 (103.0) | 027 |
| | | | 104 (104.4) | 026 |
| | | | 105 (104.4) | 026 |
| | | | 106 (105.8) | 025 |
| | | | 107 (107.3) | 024 |
| | | | 108 (107.3) | 024 |
| | | | 109 (108.9) | 023 |
| | | | 110 (110.4) | 022 |
| | | | 111 (110.4) | 022 |
| | | | 112 (112.1) | 021 |
| | | | 113 (113.7) | 020 |
| | | | 114 (113.7) | 020 |
| | | | 115 (115.5) | 017 |
| | | | 116 (115.5) | 017 |
| | | | 117 (117.2) | 016 |
| | | | 118 (117.2) | 016 |
| | | | 119 (119.1) | 015 |
| | | | 120 (121.0) | 014 |
| | | | 121 (121.0) | 014 |
| | | | 122 (122.9) | 013 |
| | | | 123 (122.9) | 013 |
| | | | 124 (124.9) | 012 |
| | | | 125 (124.9) | 012 |
| | | | 126 (127.0) | 011 |
| | | | 127 (127.0) | 011 |
| | | | 128 (127.0) | 011 |
| | | | 129 (129.2) | 010 |
| | | | 130 (129.2) | 010 |
| | | | 131 (131.4) | 007 |
| | | | 132 (131.4) | 007 |
| | | | 133 (133.7) | 006 |
| | | | 134 (133.7) | 006 |

TABLE I-continued
PROGRAMMING PARAMETER CODES AND VALUE CODES

| PARAMETER | TEMP. CODE | PERM. CODE | DATA VALUE | DATA CODE |
|---|---|---|---|---|
| | | | 135 (136.1) | 005 |
| | | | 136 (136.1) | 005 |
| | | | 137 (136.1) | 005 |
| | | | 138 (138.5) | 004 |
| | | | 139 (138.5) | 004 |
| | | | 140 (141.1) | 003 |
| | | | 141 (141.1) | 003 |
| | | | 142 (141.1) | 003 |
| | | | 143 (143.8) | 002 |
| | | | 144 (143.8) | 002 |
| | | | 145 (143.8) | 002 |
| | | | 146 (146.5) | 001 |
| | | | 147 (146.5) | 001 |
| | | | 148 (149.4) | 000 |
| | | | 149 (149.4) | 000 |
| | | | 150 (149.4) | 000 |
| R-SYNC | 270 | 260 | Nonsynchronous | 000 |
| | | | Synchronous | 001 |
| SENSITIVITY | 330 | 320 | Medium | 000 |
| | | | Low | 001 |
| | | | Medium | 002 |
| | | | High | 003 |
| OUTPUT | 370 | 360 | Single | 000 |
| | | | Double | 001 |

In Table I above the data value numbers given with respect to both high rate and rate include a non-parenthetical number and a parenthetical number. The parenthetical number represents the actual pulse per minute rate which will be provided and is limited by the frequency of the clock signal and the number of stages of shift registers. The non-parenthetical number is the closest nominal rate which would be selected by a physician in programming pulse generator 16 when it is implanted in a patient. For instance, if a physician desired to program pulse generator 16 to have a rate of 72 pulses per minute, he would depress the rate parameter key 22 and then the number 72 on the numeric keys 24 of programmer 12. He would then depress one of the permanent or temporary keys and indicate whether a permanent or temporary rate change is to occur. Assuming the rate change desired is permanent, programmer 12 would transmit a parameter code of "220" followed by a data value code of "067", an access code of "227" and a parity code of "247". Pulse generator 16 responds to this code by transmitting pulses at a rate of 71.9 pulses per minute. This is as close to the nominal desired value of 72 pulses per minute that the internal component and frequency values of pulse generator 16 are capable of transmitting stimulating pulses.

Figure 5A:
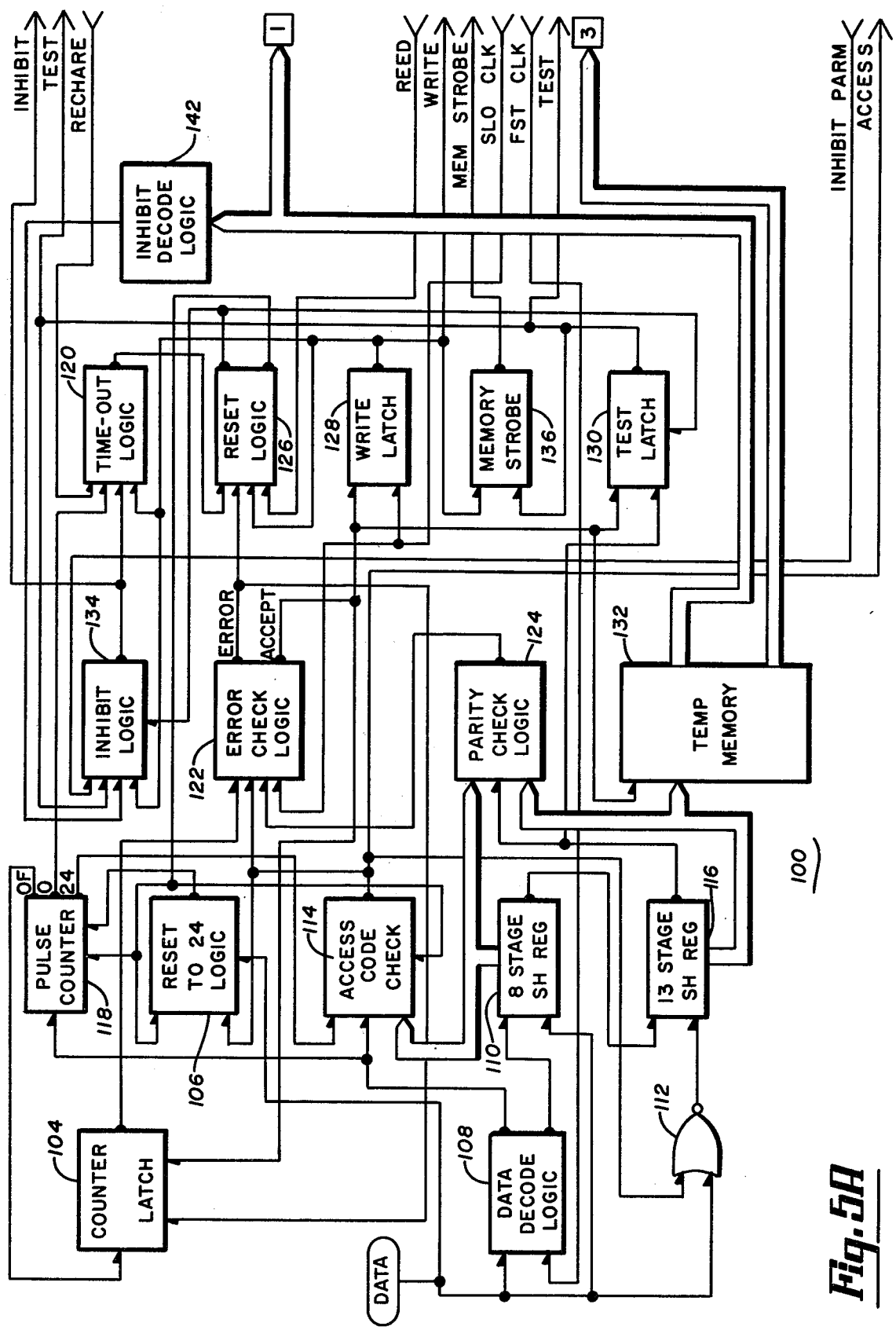
Figure 5B:
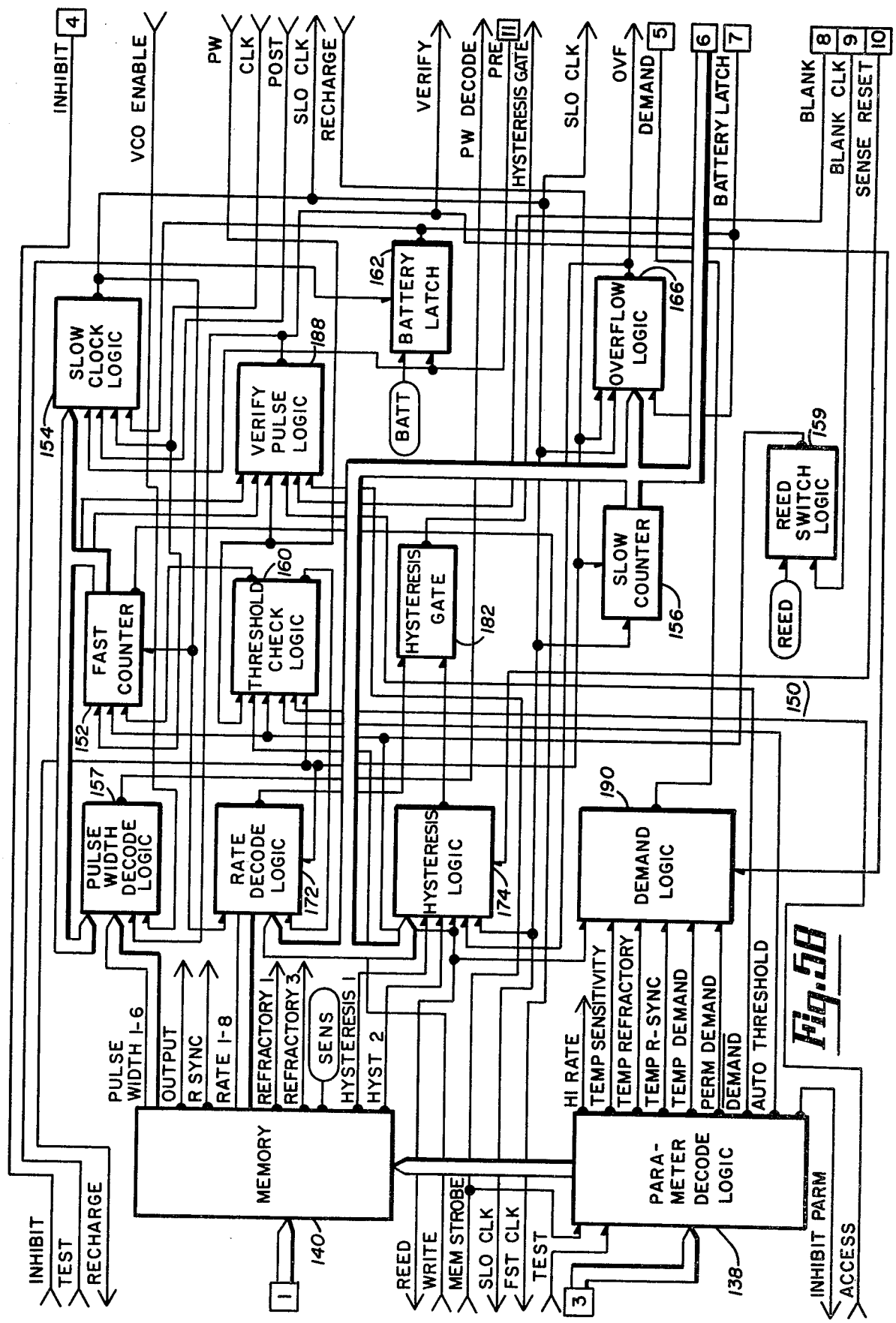
Figure 5C:
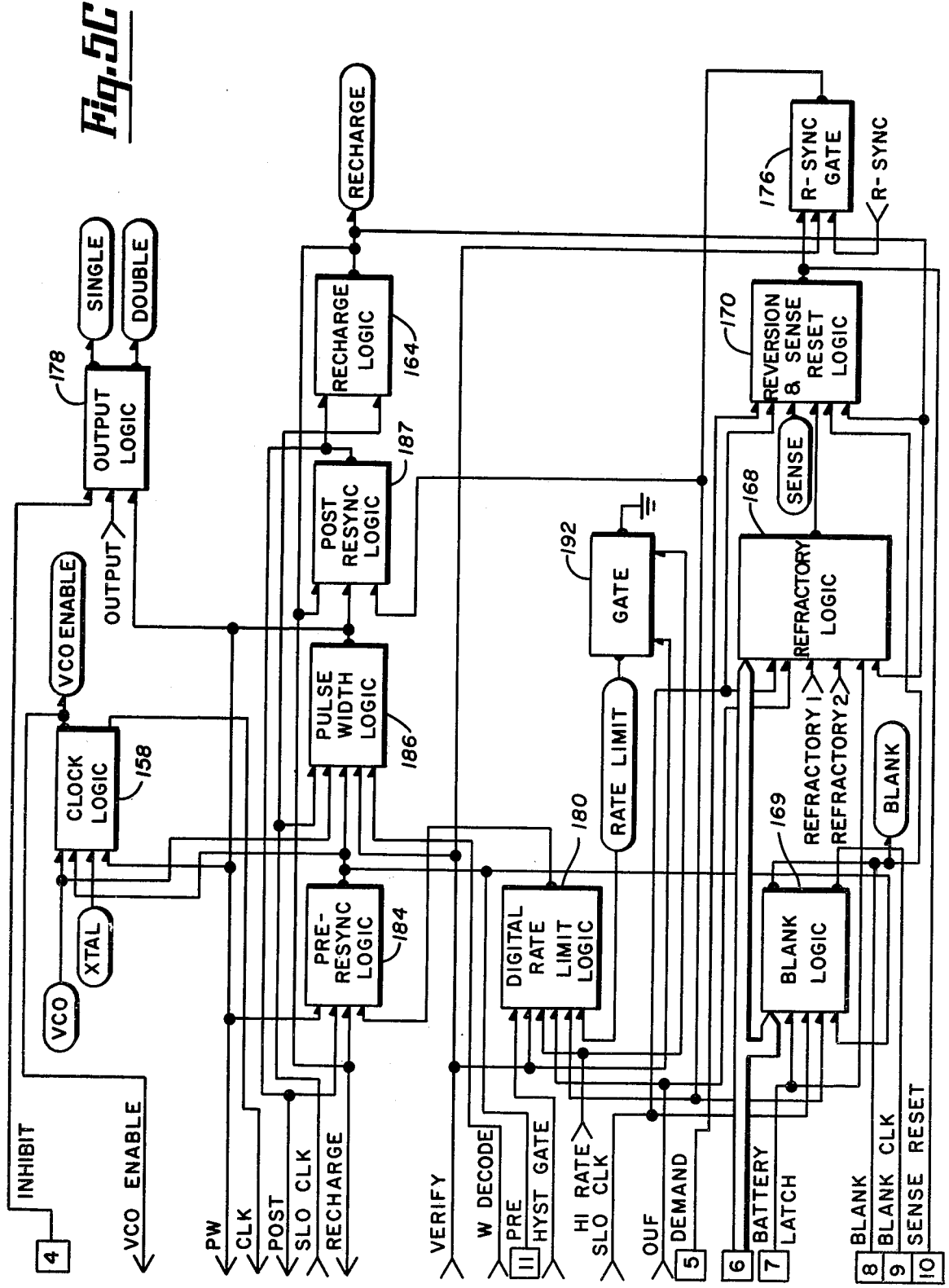

Referring now to FIG. 5, there is shown the manner of arranging FIGS. 5A, 5B and 5C to form an entire block diagram of digital circuit 40. In reviewing FIGS. 5A, 5B and 5C, it should be noted that any signals which are received from or applied to analog circuit 42 have been encircled. Further, all provisions of power supply voltage or ground coupled to each block have been deleted although it should be understood that these signals are necessary and should be coupled in the known and accepted manner of designing digital logic circuits. Also, for each of the blocks shown in FIGS. 5A, 5B and 5C, data signals are shown as being applied to the left side of the block, reset signals are applied to the bottom of the block, set signals are applied to the top of the block and the output signals are provided at the right side of the block. Lastly, wherever a plurality of lines are transmitted from or to a particular block circuit, such as a parallel output from a counter, shift register, or memory circuit, such plurality of lines are represented as wide heavy lines.

Referring now to FIG. 5A specifically, the program acceptance and processing logic 100 is shown. The DATA signal provided from analog circuit 42 is applied to reset to 24 logic 106, data decode logic 108, eight stage shift register 110 and through NOR gate 112, to thirteen stage shift register 116. As is well known in the art, a NOR gate is a circuit which provides a logic "1" signal whenever all of the signals applied to the input thereof are in a logic "0" state and provides a logic "0" signal when any one or more of the signals applied to the input thereof is in a logic "1" state. The leading edge of DATA signal resets reset to 24 logic 106 causing the output thereof to become logic "0". The trailing edge of each DATA signal pulse resets data decode logic 108 to allow a time measurement to be made between the trailing edge of one DATA signal pulse and the leading edge of the next DATA signal pulse.

In addition to the DATA signal, the fast clock signal, which is a 4,096 hz clock signal, synchronized to the system timing, is provided to data decode logic 108. Data decode logic 108 provides a data clock signal just after the trailing edge of each DATA pulse which is synchronized to the circuit timing from its upper output thereof and a digital data signal manifesting the datum value between the most recent two successive data pulses from its lower output. The data clock signal from the upper output of data decode logic 108 is coupled to the clock input to access code check logic 114 and to the clock input to pulse counter 118.

The data signal from the lower output of data decode logic 108 is coupled as the data input of eight stage shift register 110 and the DATA signal is applied to the clock input of eight stage shift register 110. Upon the occurrence of the leading edge of each DATA signal pulse, the binary value at the data input of eight stage shift register 110 is stored in the first stage thereof, and the value previously in the first stage is shifted into the second stage and so forth throughout all eight stages of shift register 110. The signal which appeared in the eighth stage of shift register 110 is applied at the output thereof to the data input of thirteen stage shift register 116. The clock input of thirteen stage shift register 116 is coupled to the output of NOR gate 112 which has the DATA signal and a normally logic "0" signal from the output of access code check logic 114 applied thereto. As long as gate 112 is enabled by the logic "0" signal from access code check logic 114, the data applied to the data input of shift register 116 is clocked thereto upon the occurrence of the leading edge of each DATA signal pulse.

The upper, or data clock, output from data decode logic 108 is applied to pulse counter 118 which increments its count beginning with a count of zero each time a pulse appears on the data clock output. Whenever the count in pulse counter 118 is nonzero, the signal at the center output thereof becomes logic "0" and is applied to enable timeout logic 120 in a manner which will be explained hereafter. After pulse counter 118 achieves a count of twentyfour, a logic "1" signal is applied from the lower output thereof to enable access code check logic 114.

Access code check logic 114 has applied thereto the parallel outputs from each of the eight stages from eight stage shift register 110 and includes decoding means which causes a logic "1" signal to be provided whenever the code stored by eight stage shift register 110 is the access code of octal 227. It should be noted that the lower output from pulse counter 118 remains as a logic "1" signal to enable access code check logic 114 from the time pulse counter 118 reaches a count of twenty-four until it overflows after reaching a count of thirty-two.

When access code check logic 114 detects the access code and provides a logic "1" signal, NOR gate 112 becomes disabled and no further DATA signals are applied therethrough to the clock input of thirteen stage shift register 116. Thus, the thirteen data values preceding the access code remain stored in thirteen stage shift register 116. As should be recalled from the discussion of the data word with respect to FIG. 3, the thirteen data values preceding the access code include eight bits defining the data, four bits defining the parameter to be modified, and one bit defining whether the modification is to be permanent or temporary. The initial three data bits in the parameter portion of the word are always zeros and during the shifting procedure, are shifted entirely through eight stage shift register 110 and thirteen stage shift register 116 to be lost.

The data provided from data decode logic 108 continues to be provided into eight stage shift register 110 following detection of the access code. However, the data stored in thirteen stage shift register 116 remains fixed because gate 112 is now closed by the provision of the logic "1" signal from access code check logic 114. Following the access code is the parity code which, eight bit times later, is stored in eight stage shift register 110.

The logic "1" signal provided from access code check logic 114, is provided to set reset to 24 logic 106 which, in turn, provides a signal to reset pulse counter 118 to a count of twenty-four. This is necessary because it is possible that a few extraneous pulses may have been provided just prior to the programming which would have caused the count of pulse counter 118 to be greater than twenty-four at the time the access code was detected by circuit 114.

After the eighth bit of the parity code is stored in eight stage shift register 110, the pulse counter 118 will have counted thirty-two data bits, and this causes a logic "0" to logic "1" change in the signal at the upper, or overflow (OF) output of pulse counter 118. The OF output from pulse counter 118 next is provided to set counter overflow latch 104, which then provides a logic "1" signal to enable error check logic 122. Error check logic 122 determines whether the received DATA programming signal has passed all of the necessary checks. These checks are both the access code check 114 signal becoming logic "1" and the parity check logic 124 signal becoming logic "1" at the time the counter overflow latch 104 signal becomes logic "1". Error check logic 122 is also responsive to a 128 hz SLO CLK signal provided from FIG. 5B to cause either an ACCEPT or an ERROR logic "1" pulse signal to be provided having a pulse width equal to the time between SLO CLK pulses.

Parity check logic 124 has applied thereto the output from the eight stages of shift register 110 and the outputs of the thirteen stages of shift register 116. Its function is to check the vertical parity of the thirteen parameter data test bits stored in thirteen stage shift register 116 against the parity code stored in eight stage shift register 110. Whenever the parity matches, a logic "1" signal is provided from parity check logic 124.

If at the time counter overflow latch 104 is set, the checks in error check logic 122 find that the programming signal is accepted, the ACCEPT signal is applied at the lower output thereof; otherwise, an ERROR signal is provided from the upper output of error check logic 122. Both the ERROR signal and the ACCEPT signal are provided to reset counter overflow latch 104. The ERROR signal is also provided to reset logic 126. The ACCEPT signal from error check logic 122 is provided to the data input of write latch 128, to the clock input of test latch 130 and to enable temporary memory 132 to receive the data and parameter signals from the first twelve stages of thirteen stage shift register 116.

Reset logic 126 is additionally responsive to the signal from timeout logic 120, to the signal from write latch 128 and to the REED signal which is logic "1" when reed switch 46 is closed. Reset logic 126 contains an upper and a lower output. The lower output is coupled to the reset input of pulse counter 118, to one input of reset to 24 logic 106 and to the reset input of access code check 114. The upper output from reset logic 126 is coupled to the reset input of the inhibit logic 134 and to the reset input of test latch 130. A signal appears at both outputs of reset logic 126 whenever a signal is provided from timeout logic 120, whenever the ERROR signal is provided or whenever the REED signal signifies that reed switch 46 is closed. A signal appears at the lower output only of reset logic 126 when a signal is provided from write latch 128.

Write latch 28 has applied to the data input thereof the ACCEPT signal from error check logic 122 and to the clock input thereof, the SLO CLK signal. Upon the occurrence of each SLO CLK pulse, write latch 128 is clocked so that the output manifests the data value of a signal applied to the data input thereof, which is the ACCEPT signal from error check logic 122. The output of write latch 128 is coupled to one input of reset logic 126, to one input of inhibit logic 134 and to one input of memory strobe 136.

The other input to memory strobe 136 is coupled from the output of test latch 130. Memory strobe 136 provides a signal to parameter decode logic 138 in FIG.

5B each time a signal is provided from write latch 128 and no signal is provided from test latch 130. The memory strobe 136 signal causes parameter decode circuit 138 to decode the parameter code applied thereto from temporary memory 132 and to provide a signal manifesting which permanent parameter change is to occur.

Test latch 130 is responsive to the test signal from the thirteenth stage of thirteen stage shift register 116 and to the ACCEPT signal from error check logic 122 and provides signal to parameter decode logic 138 in FIG. 5B to cause the parameter signals applied thereto from temporary memory 132 to be decoded and a signal provided indicating which temporary parameter change is to occur. In addition, the output from test latch 130 is applied to memory strobe 136 and to inhibit logic 134.

Temporary memory 132, upon the occurrence of the ACCEPT signal from error check logic 122, stores the four parameter and eight data bits stored in thirteen stage shift register 116. The parameter bits stored in temporary memory 132 are applied to the parameter decode logic 138, where they are decoded in conjunction with the signals from either the memory strobe 136 or the test latch 138 and a signal is provided from parameter decode logic 138 to memory 140 indicating which permanent parameter change or temporary parameter change is to occur. The possible parameter changes which can be decoded by parameter decode logic 138 and applied to memory 140 are those shown in Table I above. In addition, selected ones of the parameters, that is the High Rate parameter, the Temporary Sensitivity parameter, the Temporary Refractory parameter, the Temporary RSync parameter, the Auto Threshold parameter, the Permanent Demand parameter, the Temporary Demand parameter, the $\overline{\text{Demand}}$ parameter and the Inhibit parameter are provided as independent signals from parameter decode 138.

The eight data bits provided from temporary memory 132 are applied to memory 140 in FIG. 5B and to inhibit decode logic 142. In the event that a permanent parameter change is decoded, the data bits applied to memory 140 are stored in that portion of memory 140 enables by the decoded parameter signal. In the event that a temporary parameter change is decoded, the data signals applied from temporary memory 132 are gated through the appropriate stages of memory 140 without causing a permanent change to the previously existing data stored by memory 140.

Memory 140 includes 22 stages each of which provides either a logic "1" or a logic "0" data signal. Memory 140 is organized such that six stages are associated with pulse width data, eight stages are associated with rate data, one stage is associated with R-synchronous data, two stages are associated with each of refractory, hysteresis, and sensitivity data and one stage is associated with the output voltage magnitude data. The parameter signals determine which of the stages are to be enabled to store the new data applied from temporary memory 132 so as to be reprogrammed to provide different data signals.

The data from temporary memory 132 is also applied to inhibit decode logic 142, which provides a logic "0" signal only in the event that all of the data bits are logic "1". The output signal from inhibit decode logic 142 is provided as one input to inhibit logic 134. Inhibit logic 134, which is reset by the upper output from reset logic 126, and set in responds to the write signal and test signals provided from write latch 128 and test latch 130 and the inhibit parameter signal provided from parameter decode logic 138, and provides a signal to disable output logic 178 shown in FIG. 5C. In addition, inhibit logic 134 signal is provided to timeout logic 120.

Timeout logic 120, as previously mentioned, is responsive to pulse counter 118 having a nonzero count, to inhibit logic 134 being set and to latch 128 being set. In addition, timeout logic 120 is responsive to the recharge logic 164 signal provided from FIG. 5C which, as will be explained hereafter, is provided after each artificial stimulating pulse is to be provided by or a natural heartbeat is detected by pulse generator 16. Timeout logic 120 provides a timeout signal at its output after the second recharge logic 164 signal is applied thereto following either a write signal coincident with the setting of inhibit logic 134 following the time pulse counter 118 has a nonzero count. The timeout signal provided from the output of timeout logic 120 is applied to reset logic 126 to cause a reset signal from both of its outputs to be provided, which signals reset pulse counter 118, access code check logic 114, inhibit logic 134, and test latch 130. This, in turn, causes a general shut down of the programming circuitry shown in FIG. 5A.

The purpose of timeout logic 120 is to cause a resetting of the program acceptance and processing logic 100 shown in FIG. 5A after two cardiac stimulating pulses have been provided in the following two situations: (1) the inhibit feature is programmed, and (2) extraneous pulses cause pulse counter 118 to contain a nonzero count. When it is desired to inhibit more than two output pulses, it thus becomes necessary to provide a new inhibit programming signal prior to the time the two pulses have been inhibited in order to reset timeout logic 120. In practice, to program the inhibit feature, programmer 12 may be designed to provide continual inhibit programming signals as long as the inhibit function button 26 is maintained depressed.

Referring now to FIGS. 5B and 5C the pulse generating portion 150 of pulse generator 16 is shown. The timing sequence used to control the pulse width, the rate, the refractory time, the lower hysteresis rate, and the amplifier blanking time is determined by fast counter 152, slow clock logic 154 and the slow counter 156. Fast counter 152 counts the clock pulses provided thereto from clock logic 158 which provides at its lower output a clock signal equal to either the external crystal oscillator (XTAL) signal or the VCO signal, both of which are applied to clock logic 158. A second input to fast counter 152 is from the threshold check logic 160 that causes fast counter 152 to count at a faster rate during a specific portion of the threshold check time period. A third input to fast counter 152 is the reed switch logic 159 signal which allows the 4,096 hz FST CLK signal to be applied as the clock input to data decode logic 108 in FIG. 5A whenever reed switch 46 is closed.

Fast counter 152 is a nine stage binary counter connected in a known manner. The outputs from the lower seven stages of fast counter 152 are applied to pulse width control logic 157. The outputs from the second, third, fourth, fifth and ninth stages of fast counter 152 are applied to slow clock logic 154. In addition the output from battery latch 162, and the clock signal from clock logic 158 are applied as inputs to slow clock logic 154. Slow clock logic 154 responds to the output from fast counter 152 by providing a 128 hz SLO CLK signal as long as the voltage of battery 44 is above a certain minimum value. Whenever the voltage provided from battery 44 falls below that minimum value, the BATTERY signal applied from the Battery Status portion of analog circuit 42 causes battery latch 160 to become reset. This, in turn, causes the rate of the signal provided from slow clock logic 154 to be reduced by approximately ten percent, or to become approximately 113 hz.

The output from slow clock logic 154 is provided as the input to slow counter 156. Slow counter 156 is an eight stage binary counter connected in a known manner and can be set upon a logic "1" signal being applied to the set input thereof from recharge logic 164 to a count of two hundred and eight. Selected ones of the outputs of the eight stages of slow counter 156 are applied to overflow logic 166, refractory logic 168, blank logic 169, rate control logic 172 and hysteresis logic 174.

The output signals from the six stages of the pulse width portion of memory 140 are applied to pulse width decode logic 157 and the output signals from the eight stages of the rate portion of memory 140 are applied to rate decode logic 172. The output from the R-sync stage of memory 140 is applied to R-sync gate 176. The signals from the two refractory stages of memory 140 are applied to refractory logic 168. The signals from the two hysteresis stages of memory 140 are applied to hysteresis logic 174. The signal from the two sensitivity stages of memory 140 are combined and a single SENSITIVITY signal is applied to the sense amplifier on analog circuit 42, shown in FIG. 4. Lastly, the signal from the output stage of memory 140 is applied to output logic 178.

The general philosophy of programming the circuitry shown in FIGS. 5A, 5B and 5C is to change the values stored by memory 140 in order to cause a parameter to be changed. The programmed change then occurs as a result of individual circuits within FIGS. 5B and 5C responding to different sets of values applied thereto from memory 140. In addition to the above mentioned circuits, FIGS. 5B and 5C include reversion logic 170, digital rate limit logic 180, hysteresis gate 182, pre-resync logic 184, pulse width logic 186, postresync logic 187, verify pulse logic 188, demand logic 190 and gate 192.

The description for the remainder of the block diagram shown in FIGS. 5B and 5C will be in terms of general operation. The detailed connection and operation of each individual block will be given with respect to FIGS. 6A through 6N.

Immediately after a cardiac stimulating pulse is provided or natural cardiac activity is sensed, fast counter 152 is reset to a count of zero and slow counter 156 is set to a count of 208. The count of 208 is selected so that the overflow of slow counter 156 from a full count of 255 to a zero count will occur at a time which can be used to obtain a 400 msec timing signal. This 400 msec timing signal is used to determine an upper rate limit and as one of the programmable refractory times.

After being reset, fast counter 152 begins counting the clock pulses provided thereto from clock logic 158. At this point in time clock logic pulses originate from the external oscillator and are a frequency of 32,768 hz. Assuming the battery voltage is not low and battery latch 162 remains set, each time the ninth stage of fast counter 152 is set, the signal will be applied therefrom to slow clock logic 154. This will occur at a frequency of 128 hz. One clock pulse later, a SLO CLK pulse is provided for one clock signal pulse period. This SLO CLK pulse is applied to reset fast counter 152 to a count of zero and one clock signal pulse period later fast counter 152 begins counting again. Hence the frequency of the SLO CLK pulses is actually closer to 127 hz.

The pulses from the output of slow clock logic 154 are provided to the input of slow counter 156 which increments its count from the initial count of 208 each time a pulse is provided thereto from slow clock logic 154. During the time slow counter 156 is counting from its set value of 208 to its full value of 255, blank logic 169 and refractory logic 168 provide signals at the appropriate times, based on decoding selected counts from slow counter 156, to reversion logic 170 to allow the refractory and reversion functions to operate. As is well known in the art, the refractory period is a certain time after either an artificial pulse is provided or a natural heartbeat occurs during which no response is made to sensed electrical signals and the reversion function disables all response to sensed electrical signals in the event a continuous wave signal is being sensed.

At the time slow counter 156 achieves a full count and overflows back to a zero count, overflow logic 166 will respond and provides a signal to enable digital rate limit logic 180 to be able to provide a pulse at its output. As will be explained hereafter, it is the rate limit logic 188 pulse that begins the chain of events leading to the provision of a stimulating pulse by pulse generator 16.

Slow counter 156 then begins incrementing its count from zero until it reaches a count similar to the count contained in the eight stages of the rate portion of memory 140. Signals from the rate portion of memory 140 and from each stage of slow counter 156 are applied to rate decode logic 172, which generates a signal when the next SLO CLK pulse occurs following the time the count in slow counter 156 equals to code stored in memory 140. This assumes that no signal is applied from threshold check logic 160 to rate decode logic 172. The signal from rate decode logic 172 is applied through hysteresis gate 182 which is enabled if no hysteresis is programmed or if the preceding heart beat was artifically stimulated. However, if hysteresis is programmed and the last occurring heart beat was a natural beat, hysteresis logic 174 will be set to disable hysteresis gate 182 so that no signal can pass through hysteresis gate 182 until a time has passed equal to the hysteresis timeout period measured from the last natural beat.

The pulse at the output of hysteresis gate 182 is provided to digital rate limit logic 180 which, if enabled by the signal from overflow logic 166, provides a signal to set pre-resync logic 184. Logic 184 provides a signal to clock logic 158 to cause the VCO ENABLE signal to be provided, resulting in the VCO beginning to provide clock signals to clock logic 158, and to pulse width logic 186. The VCO ENABLE signal is utilized within clock logic 158 to cause the clock pulses provided therefrom to be the VCO pulses rather than the external oscillator pulses. The pre-resync logic 184 signal is also provided to slow clock logic 154 to cause an extra SLO CLK pulse to be provided to reset fast counter 152 to a count of zero. In addition the pre-resync logic 184 signal causes blank logic 169 to provide the BLANK signal for 100 msec and enables pulse width logic 186 to provide the leading edge of the logic "1" pulse width (PW) logic 186 signal upon the occurrence of the next VCO clock pulse. Thus, the primary purpose of pre-resync logic 184 is to cause the timing logic to be resynchronized to the change from external oscillator timing pulses to VCO timing pulses. It should be recalled that the VCO timing pulses occur at a nominal rate of 40,000 hz whereas the external clock timing pulses occur at a rate of 32,768 hz.

As fast counter 152 increments its count from zero in response to the VCO timing pulses applied thereto from clock logic 158, the output of the second through seventh stages thereof are compared against the signals stored in the pulse width portion of memory 140 by pulse width decode logic 157. At the time a comparison is made, which will be the count of fast counter 152 equivalent to the duration of the desired pulse, pulse width decode logic 157 provides an output signal to pulse width logic 186 to cause the then logic "1" signal provided thereby to return to logic "0" upon the occurrence of the next VCO clock pulse. Thus the PW signal at the output of pulse width logic 186 is a signal having a pulse width equal to programmed pulse width for the signal to be provided from pulse generator 16.

The signal from the output of pulse width logic 186 is provided to output logic 178 which provides a pulse signal having the same pulse width as the pulse width logic 186 signal over either the SINGLE or the DOUBLE output depending upon the value of the OUTPUT signal from memory 140. It should be recalled that the SINGLE and DOUBLE output signals from output logic 178 are coupled to analog circuit 42, shown in FIG. 4, and cause a voltage pulse of either battery 44 voltage or twice battery 44 voltage to be provided from pulse generator 16 over lead 18 to the heart.

The pulse width logic 186 signal is also provided to clock logic 158 to maintain the VCO ENABLE signal provided. When the pulse width logic 186 signal returns to logic "0", the VCO ENABLE signal is removed and the crystal oscillator XTAL clock signal is again provided from the clock output of clock logic 158. In addition, the pulse width logic 186 signal, is provided to post-resync logic 187 to cause a post-resync logic 167 signal to be provided at the time the pulse width logic 186 signal returns to logic "0". The post-resync logic 187 signal causes slow clock logic 154 to provide an extra pulse upon the occurrence of the next XTAL clock signal to reset fast counter 152 so as to be resynchronized to the XTAL clock pulses then being provided. The post-resync logic 187 signal is also applied to recharge logic 164, which upon the occurrence of that next slow clock logic 154 signal becomes set and provides a logic "1" recharge logic 164 signal to the voltage doubler portion of analog circuit 42 to allow the doubling capacitor therein to be recharged. The recharge logic 164 signal is also provided to reset post-resync logic 187, so that upon the next slow clock logic 154 signal, recharge logic 164 becomes reset and no longer provides a logic "1" signal. The output from recharge logic 164 is also provided to reset slow counter 156, to a count of 208, to enable refractory logic 168 and reversion logic 170, and to reset rate decode logic 172 and overflow logic 166 and the above process is repeated.

In addition to the above mentioned circuit portions in FIG. 5B, verify pulse logic 188 and demand logic 190 are provided. Verify pulse logic 188 is utilized to cause an additional pulse to be provided at the end of the 100 msec BLANK time in the event memory strobe logic 136 signal from FIG. 5A is provided. This second pulse is provided in order to give an indication to the operator of programmer 12 that the program has been accepted. The verify logic 188 extra pulse may be of a low pulse width so as to be nonstimulating and further timed to occur at a non-critical point in the electrocardiac signal process. It is also possible to merely extend the interval between successive stimulating pulses by 100 msec rather than provide an extra pulse so that an indication of program acceptance to the operator.

Demand logic 190 operates to override the normal effects of the closure of reed switch 46 which is to inhibit any response to the SENSE signal provided from the sense amplifier in analog circuit 42. However, the inhibition effect of the reed switch is overridden in the event that there is temporary programming of either amplifier sensitivity, R-synchronous mode or refractory time or in the event that the demand mode is programmed on either a temporary or a permanent basis, despite the closure of the reed switch.

One other element included in FIG. 5C is gate 192 which is closed in response to the HI RATE parameter signal from parameter decode 138 in FIG. 5A or in response to a signal from verify pulse logic 188. When gate 192 is closed it grounds the RATE LIMIT output pad, thereby disabling the effects of the analog rate limit circuitry in analog circuit 42 and digital rate limit logic 180. It is necessary to remove the rate limit protection when it is desired to program the rate to a high value or upon the occurrence of the verify pulse.

At this point a more detailed description of each of the blocks shown in FIGS. 5B and 5C will be given with the above overview of the operations being kept in mind. Pulse width decode logic 157 responds to the output of the first seven stages of fast counter 152 and the signals from the six outputs of the pulse width portion of memory 140. In addition pulse width decode logic 157 responds to the provision of the signal from the verify pulse logic 188 and the VCO ENABLE signal from clock logic 158. Pulse width decode logic 157 provides a pulse signal having a leading edge which causes the desired trailing edge of the pacemaker stimulating pulse to occur. This pulse signal is provided either in response to the signal from the verify pulse logic 188 or in response to a comparison between the count of counter 152 and the digital code stored in the pulse width portion of memory 140. The output from pulse width decode logic 157 is applied as one input to pulse width logic 186.

Threshold check logic 160 responds to the pulse width logic 186 signal, the write latch 128 signal from FIG. 5A, the Autothreshold signal from the parameter decode 138, the reed switch logic 159 signal, the access code check logic 114 signal from FIG. 5A and the recharge logic 164 signal. Threshold check logic 160 provides two output signals, the upper one of which is provided to fast counter 152 to cause the first two stages of fast counter 152 to become a divide by three rather than divide by four network. The upper output signal from threshold check logic is a pulse signal occurring in time coincidence with the third pulse width logic 186 signal following either the closure of the reed switch or the provision of the write latch 128 signal and the Autothreshold signal.

The lower output signal from threshold check logic 160 is a signal commencing immediately after the first stimulating pulse provided following either the closure of reed switch 46, manifested by a signal from reed switch logic 159 or the provision of the write latch 128 signal together with the provision of the Autothreshold parameter signal and lasts until after the provision of four additional pulse width logic 186 signals. This lower signal from threshold check logic 160 is provided to one input of rate decode logic 172.

The threshold check sequence is a series of four pulses occurring at a rate of 100 beats per minute with the first three pulses in the sequence being of normal programmed pulse width and the fourth pulse having a pulse width of 75% of the programmed width. In the situation where the Autothreshold signal is provided, the data portion of the Autothreshold programming word will designate the desired temporary pulse width for the initial three pulses in the sequence and the fourth pulse in the sequence will be 75% of that designated pulse width. The Autothreshold feature is useful to physicians for checking the threshold safety margin of the stimulating pulse provided by pulse generator 16 to determine at what pulse width capture is lost. Then the physician can set a pulse width in a permanent mode to insure an adequate safety margin.

Rate decode logic 172 responds to the slow clock logic 154 signal, the code in the rate portion of memory 140, the count of slow counter 156, the lower output from threshold check logic 160 and the recharge logic 164 signal. Rate decode logic 172 includes a latch which is reset by the recharge logic 164 signal occurring after each pulse width logic 186 signal or a detected natural heartbeat. When the latch is set, it provides a signal through hysteresis gate 182, and digital rate limit circuit 180 to begin the sequence leading to the provision of the pulse width logic 186 signal. The latch within rate decode logic 172 is set by the slow clock logic 154 signal following the matching of the slow counter 156 with the coded rate signals applied thereto from memory 140 if no signal from threshold check logic 160 is applied or at a rate of 100 beats per minute, or the programmed rate if greater than 100 beats per minute, if the signal from threshold check logic 160 is applied. In the event hysteresis gate 182 is not enabled by hysteresis logic 174, the latch remains set, thereby applying a continuous signal to hysteresis gate 182, until it becomes enabled and the recharge logic 164 signal is provided after the provision of the stimulating pulse. Thus, a signal is provided to hysteresis gate 182 until it is enabled by hysteresis logic 174 to cause a stimulating pulse to be provided.

Hysteresis logic 174 responds to selected counts of slow counter 156, the slow clock logic 154 signal, the two hysteresis signals from the outputs of the hysteresis portion of memory 140, the reed switch logic 159 signal, the overflow logic 166 signal and the sense reset signal from reversion and sense reset logic 170, and provides a hysteresis gate enable signal. Hysteresis logic 174 includes a latch circuit which is reset each time a signal is provided from reversion and sense reset logic 170 indicating the sensing of natural cardiac activity and which is set whenever the hysteresis timeout period expires. The hysteresis timeout period is determined by the code of the Hysteresis 1 and Hysteresis 2 signals from memory 140 enabling selected decoding gates responsive to the selected counts of slow counter 156 and overflow logic 160. In addition, the Hysteresis 1 and Hysteresis 2 signals can indicate no hysteresis function, in which case the hysteresis logic latch is held in a set condition. Finally, the hysteresis logic latch is held in a set condition whenever reed switch 46 is closed. The output signal from hysteresis logic 174 is the latch output which maintains hysteresis gate 182 enabled whenever it is in a set condition.

Demand logic 190 responds to the closure of reed switch 46 and the provision of the reed switch logic 159 signal by providing an output signal to prevent reversion and sense reset logic 170 from responding to the SENSE signal from the sense amplifier included in analog circuit 42. However, if it is desired to temporarily program the sensitivity of the sense amplifier, or temporarily program pulse generator 16 to operate in the R-synchronous mode or temporarily program a refractory time change, the physician could not observe any response due to the inhibition of the response to the SENSE signal. Hence the temporary sensitivity, the temporary refractory and the temporary R-sync from parameter decode logic 138 are provided to demand logic 190 to override the effects of the closure of reed switch 46. Further, whenever the physician desires to either temporarily or permanently program pulse generator 16 to operate in the demand mode while reed switch 46 is closed, the amplifier response inhibition due to the closure of reed switch 46 is overridden. Also, whenever the verify pulse is provided, a signal from verify pulse logic 188 is provided to override the inhibition of the sense amplifier due to the closure of reed switch 16.

Fast counter 152 responds to the clock pulses provided from the lower output of clock logic 158, which during the period between the provision of stimulating pulses are provided from the external oscillator in analog circuit 42 and during provision of the stimulating pulse are provided from the VCO in analog circuit 42, and fast counter 152 is reset in response to each slow clock logic 154 signal. In addition fast counter 152 is responsive to the upper output signal from threshold check logic 160 which converts the first two stages of the nine stage fast counter 152 into a divide by three rather than a divide by four network. When the first two stages are converted to a divide by three network, fast counter 152 will achieve a given count in a period of time 75% of the time necessary when the first two stages are a divide by four network. This feature is used to allow the threshold check pulse to be provided having a width 75% of the normal programmed pulse width.

One output from fast counter 152 is the fast clock signal which is taken from the third stage of fast counter 152 and provided whenever the signal from reed switch logic 159 manifests that the reed switch is closed. The outputs from the second, third, fourth, fifth and ninth stages of fast counter 152 are provided to slow clock logic 154 and the outputs from the first seven stages are provided to pulse width decode logic 157 where the second through seventh stage outputs are compared with the programmed pulse width data in memory 140 to cause the provision of a signal terminating the pulse provided by pulse width logic 186 at the proper time.

Verify pulse logic 188 responds to the memory strobe 136 signal, the outputs from the third and fifth stages of fast counter 152, the BLANK signal provided from blank logic 169, the pulse width logic 186 signal, and the $\overline{\text{Demand}}$ signal from parameter decode logic 138. Verify pulse logic 188 operates to cause a verify pulse to be provided upon the occurrence of each memory strobe pulse signal provided from memory strobe logic 136 in FIG. 5A unless the demand parameter is being programmed, and the $\overline{\text{Demand}}$ signal is logic "0". The verify pulse is provided after the time the BLANK signal from blank logic 169 returns to its normal logic "1" value and has a pulse width determined by the timing signals from fast counter 152. The output from verify pulse logic 188 is provided to digital rate limit logic 180 to cause the leading edge of a stimulating pulse and to gate 192 to override the rate limit inhibition. The verify pulse logic 188 signal is also applied to inhibit pulse width decode logic 157 and to pulse width logic 186 to determine the trailing edge of the verify pulse. Lastly, the verify pulse logic 188 signal is provided to R-Sync gate 176 to cause both the normal and verify pulses to be synchronized with detected R waves to prevent any double stimulating pulse to be provided in the so-called venerable zone around the T wave.

Hysteresis gate 182 passes the signal applied thereto from rate decode logic 172 to digital rate limit logic 180 unless it is disabled by a signal from hysteresis logic 174.

Slow counter 156 is an eight stage binary counter which has the count stored thereby incremented by one each time the slow clock logic 154 signal is applied to the first stage thereof. The outputs from selected stages of slow counter 156 are applied to various other circuit portions to obtain proper timing. Specifically the outputs from selected stages of slow counter 156 are applied to overflow logic 166, refractory logic 168, blank logic 169, rate decode logic 172 and hysteresis logic 174. After each stimulating pulse is generated by pulse generator 16 in response to the pulse width logic 186 signal, slow counter 156 is set to a count of 208 by the recharge logic 164 signal. Thereafter slow counter 156 counts upwards each time a slow clock logic 154 signal is applied thereto until it reaches a full value of 255. During this time, the 100 msec BLANK pulse time from blank logic 169 and the programmed refractory periods controlled by refractory logic 168 are determined in response to the count of slow counter 156. After slow counter 156 counts to a full value, it overflows and has a count of zero therein, thereby setting overflow logic 160. At this point it begins counting upward again each time a slow clock logic 154 pulse is provided. As slow counter 156 continues counting upward, the outputs from its stages are applied to hysteresis logic 174 and to rate decode logic 172 and compared against programmed values or decoded by enabled gates. After a rate time-out period is determined, thereby causing a stimulating pulse to be provided, slow counter 156 is again set to a count of 208.

Reed switch logic 159 responds to the REED input line indicative of whether reed switch 46 is open (logic "0") or closed (logic "1") and to a clocking signal from blank logic 169 which occurs whenever a stimulating pulse is provided or natural cardiac activity is sensed. The output from reed switch logic 159 is a signal indicating the state of the reed switch 46.

Slow clock logic 154 responds to the set signals from the second, third, fourth, fifth and ninth stages of fast counter 152, to the post-resync signal from post-resync logic 187, to the pre-resync signal from pre-resync logic 184, to the clock signal from clock logic 158 and to the battery latch signal from battery latch 162 and provides the 127 hz slow clock logic 154 signal. As long as battery latch 162 is set indicating normal battery voltage, a slow clock logic 154 pulse is provided one clock logic 158 pulse time after the ninth stage of fast counter 152 is set. However, if battery latch 162 becomes reset, manifesting a low battery voltage, it is desirable to reduce the rate of the pulses provided by the pulse generator 16 by approximately 10 percent. In the low battery voltage condition a slow clock logic 154 pulse is provided when the second, third, fourth, fifth and ninth stages of fast counter 152 are set. In this condition, the rate of the slow clock logic 154 pulses occur at a rate approximately 10 percent slower than would be the condition had battery latch 162 been set. In addition, a slow clock logic 154 pulse is provided each time the pre-resync and post-resync signals occur in order to reset fast counter 152 to begin counting the VCO clock pulses from clock logic 158.

Battery latch 162 has the output of pre-resync logic 184 applied to the clock input thereof and the BATTERY signal from the battery status monitor within analog circuit 42 applied to the data input thereof. In addition, the test signal from test latch 130 in FIG. 5A is applied to the set input of battery latch 162 to to set it each time a temporary programming effort occurs in order to determine if the previously sensed low voltage condition was accidental or real. With normal voltages, the BATTERY signal is logic "1" and battery latch 162 is maintained set. It should be noted that the pre-resync signal used to clock battery latch 162 occurs just prior to the provision of each stimulating pulse, so that instantaneous battery drain as a result of the provision of the stimulating pulse does not effect the BATTERY signal.

The output from battery latch 162 is applied to slow clock logic 154 to cause the slow clock logic 154 pulses to be at an approximately 10 percent slower rate. In addition, the output from battery latch 162 is provided to refractory logic 168 and blank logic 169 and overflow logic 166 to enable alternate gates to decode different counts of slow counter 156 in order to maintain the times decoded constant, despite the 10 percent slower slow clock logic 154 pulse rate.

Overflow logic 166 is responsive to the slow clock logic 154 signal, the signal from battery latch 162, the recharge logic 164 signal and signals from output stages of slow counter 156. As long as battery latch 162 is set, overflow logic 166 responds to the final stage of slow counter 156 going from a set to a reset condition after slow counter 156 has been set to a count of 208 by the recharge logic 164 signal. However, if battery latch 162 is set, overflow logic 166 provides an output when all stages, except the third stage of slow counter 156, are set, so that the output from overflow logic 166 occurs 400 msec after slow counter 156 was set regardless of the rate of the slow clock logic 154 pulses. Overflow logic 166 includes a latch which is reset by the recharge logic 164 signal and which is set by the slow clock logic 154 signal following the time the last stage of slow counter 156 becomes reset. The output from overflow logic 166 is provided to enable digital rate limit logic 180 and as the 400 msec refractory time signal to refractory logic 168.

Referring now to FIG. 5C, clock logic 158 is responsive to the VCO signal from the voltage controlled oscillator on analog circuit 42 and the XTAL signal from the crystal oscillator on analog circuit 42. In addition, clock logic 158 is responsive to the pre-resync logic 184 signal and the pulse width logic 186 signal. Clock logic 158 provides a clock signal from its lower output and a VCO ENABLE signal from its upper output. The VCO ENABLE signal is provided during the time following the provision of the pre-resync logic 184 signal and including the time that the pulse width logic 186 signal is provided. The clock signals provided from the lower output of clock 158 are the XTAL pulses during the time the VCO ENABLE signal is not provided and the VCO signal pulses during the time the VCO ENABLE signal is provided.

The provision of the cardiac stimulating pulse is controlled by digital rate limit logic 180, pre-resync logic 184 and pulse width logic 186, and the resyncing and resetting of various elements within FIGS. 5B and 5C is controlled by post-resync logic 187 and recharge logic 164.

Digital rate limit logic 180 responds to the hysteresis gate 182 signal, the verified pulse logic 188 signal, the High Rate parameter signal from parameter decode 138, the overflow logic 166 signal, the R-sync gate 176 signal and the RATE LIMIT signal from analog circuit 42 and provides a signal at its output which ultimately causes the cardiac stimulating pulse to be provided. Under normal operation, each time a signal is provided to digital rate limit logic 180 from hysteresis gate 182, a signal is provided from the output of digital rate limit logic 180. However, in the event that the signals provided from hysteresis gate 182 occur at a rate exceeding either the 150 beat per minute digital rate upper imit or the 130 beat per minute analog upper rate limit, as determined by the overflow signal from overflow logic 166 or the RATE LIMIT signal from analog circuit 42, digital rate limit logic 180 causes a postponement of the provision of a signal in response to the hysteresis gate signal until such time as the upper rate limit time period has expired.

In certain situations, however, it is desirable to override the upper rate limit functions contained in digital rate limit logic 180 and analog circuit 42 and to allow signals to be provided therefrom at a rate exceeding the upper rate limit. Specifically, these situations include the provision of the verified pulse which occurs approximately 100 msec after a normal pulse, or at a rate of 600 pulses per minute, or in the situation where a high rate parameter is being programmed, in which case signals can be provided up to a rate as high as 400 pulses per minute. If either of these situations occur, the high rate parameter signal or the verify signal will override digital rate limit logic 180. In addition, these two signals are applied to gate 192, which causes the RATE LIMIT signal to be forced to ground or a logic "0" value, and thus override the analog rate limit feature contained in analog circuit 42.

If the R-synchronous mode is programmed, a signal is also applied to digital rate limit logic 180 from R-sync gate 176 each time natural cardiac activity is sensed. This in turn causes a signal to be provided at the output of digital rate limit logic 180, resulting in a cardiac stimulating pulse beat provided by pulse generator 16.

Pre-resync logic 184 responds to the output signal from digital rate limit logic 180 and provides a signal which causes clock logic 158 to begin providing VCO pulses at its lower output. In addition, the pre-resync logic 184 signal causes clock logic 158 to provide the VCO ENABLE signal to enable the VCO to begin providing pulses to clock logic 158. Pre-resync logic 184 is additionally responsive to the pulse width logic 186 signal, the post-resync logic 187 signal and the recharge logic 164 signal. When any one of these last three mentioned signals are provided, pre-resync logic 184 is reset and can only be set by the provision of a signal from digital rate limit logic 180. It should be recalled that the pre-resync logic 184 signal is provided to slow clock logic 154 in FIG. 5B to cause an additional slow clock signal to be provided. The purpose of this additional slow clock pulse is to reset fast counter 152 so that it may accurately count the then-to-be provided VCO pulses from a known initial count of zero.

Pulse width logic 186 controls the width of the output pulse to be provided by pulse generator 16 in response to the slow clock logic 154 signal, the VCO signal from analog circuit 42, the pre-resync logic 184 signal, the verify pulse logic 188 signal and the pulse width control logic 187 signal. The leading edge of the pulse provided by pulse width logic 186 occurs in response to the setting of pre-resync logic 184 by the digital rate limit logic 180 signal. The trailing edge of the pulse provided by pulse width logic 186 is determined in response to a signal from pulse width decode logic 157 or verify pulse logic 188.

Post-resync logic 187 responds to the recharge logic 164 signal, the trailing edge of the pulse width logic 186 signal and the signal from R-sync gate 176 and provides a signal at the time of the trailing edge of the pulse width logic 186 signal to slow clock logic 154 to cause an additional slow clock pulse to be provided. This pulse is necessary to resync the timing in the system to the provision of the crystal oscillator pulses from clock logic 158 as a result of the end of the pulse width logic 186 signal. Post-resync logic 187 is thereafter reset by the provision of the recharge logic 164 signal. In the event that the demand mode is programmed, rather than the R-synchronous mode, post-resync logic 187 responds to the signal from R-sync gate 176 by causing an output pulse to be provided. The purpose of this pulse is to cause a resetting of the various timing functions within FIGS. 5B and 5C whenever a natural cardiac signal is detected.

Recharge logic 164 responds to the post-resync logic 187 signal and to slow clock logic 154 signal and provides at its output a single pulse recharge signal having a duration equal to the time between slow clock pulses. The recharge signal is the primary signal used in resetting the various timing functions within the circuits contained in FIGS. 5B and 5C.

Blank logic 169, refractory logic 168, reversion and sense reset logic 170 and R-sync gate 176 interact together to operate during the period after a cardiac stimulating pulse is provided and prior to the provision of the next cardiac stimulating pulse in controlling the events which occur as a result of sensing natural cardiac activity.

Blank logic 169 responds to selected outputs from slow counter 156, the battery latch 162 signal, the slow clock logic 154 signal, the output from R-sync gate 176, and the pre-resync logic 184 signal and provides the BLANK signal from its upper output and a blank clock signal from its lower output. The blank clock signal from the lower output of blank logic 169 is a pulse occurring at the time of the provision of the pre-resync logic 184 signal or the provision of a signal from R-sync gate 186, resulting from sensing natural cardiac activity and initiates the leading edge of the BLANK signal. The trailing edge of the blank signal occurs 100 msec after the leading edge, regardless of whether battery latch 162 is set or reset. As previously mentioned, the BLANK signal is provided to analog circuit 42 to cause the QRS sensing amplifier to be disabled during the 100 msec that it is provided.

Refractory logic 168 responds to the count of slow counter 156, the slow clock logic 154 signal, the overflow logic 166 signal, the Refractory 1 and Refractory 2 signals from memory 140, battery latch 162 signal and the recharge logic 164 signal and provides a signal at a certain time after the provision of the cardiac stimulating pulse. This certain time is determined by the code of the Refractory 1 and Refractory 2 signals from memory 140, which enable coding gates within refractory logic 168. The refractory times which can be selected are no refractory time, 325 msec, 400 msec or infinity. The 400 msec refractory time is set by the output from overflow logic 166 and the 325 msec refractory time is determined by decoding gates within refractory logic 168, which decode the count of slow counter 156. These gates are enabled in accordance with whether battery latch 162 is set to maintain the 325 msec refractory time constant regardless of the rate of the slow clock logic 154 pulses. The refractory period is measured from the time that the recharge logic 164 signal is provided to reset refractory logic 168. In the situation where no refractory time is set, the refractory period is measured by the 210 msec counter in reversion and sense reset logic 170.

Reversion and sense reset logic 170 responds to the demand logic 190 signal, slow clock logic 154 signal, the SENSE signal from analog circuit 42, the refractory logic 168 signal, the BLANK signal from blank logic 169 and the recharge logic 164 signal, and provides a sense reset signal at its output each time a SENSE signal is provided after the refractory time, unless the reversion function overrides. The reversion function is controlled by a counter which counts in response to the slow clock logic 154 signals until it reaches a time of approximately 210 msec following either the provision of the recharge signal or the occurrence of a SENSE signal. If a sense signal occurs after the BLANK time and prior to the time the reversion counter counts to 210 msec, the reversion counter is reset to a zero count. No sense reset signal can be provided until after the reversion counter reaches the 210 msec time. Thus, any interference signal having a frequency greater than about five hz will cause reversion and sense reset logic 170 to be nonresponsive to all SENSE signals, that is, to revert to the asynchronous mode.

Reversion and sense reset logic 170 also responds to the refractory logic 168 signal by inhibiting the provision of the sense reset signal in response to a SENSE signal occurring prior to the expiration of the refractory time. Thus, the sense reset signal is provided at the output of reversion and sense reset logic 170 to indicate the natural cardiac activity sensing only after both the reversion counter time and the refractory time have passed. Further, it should be noted that if the refractory time is set at infinity, there will be no response to the SENSE signal and the pulse generator operates in the asynchronous mode.

The reversion and sense reset logic signal is provided as one input to the three input R-sync gate 176. The R-sync signal from memory 140 is applied to the second input of R-sync gate 176 and acts as an enable signal and a signal from verify pulse logic 188 is applied to the third input. If the demand mode is programmed, the signal from R-sync gate 176 is provided to post-resync logic 187 and to blank logic 169 to cause a resetting of the timing functions within FIGS. 5B and 5C. If the R-sync mode is programmed, the output from R-sync gate 176 is provided to digital rate limit logic 180 to cause a cardiac stimulating pulse to be provided in synchronism with the detected natural cardiac activity. Also, whenever the verify pulse is provided, the R-sync mode is programmed for both the verify pulse and the normal pulse preceding the verify pulse.

Referring now to FIGS. 6A through 6N, a more detailed description of each of the blocks shown in FIGS. 5A, 5B and 5C will be given. FIGS. 6A through 6N are organized in such a manner that all of the logic elements associated with a particular block shown in FIGS. 5A, 5B or 5C are in the same location and surrounded by a darker line having a number corresponding to the block number in FIGS. 5A, 5B and 5C. The component parts of each block include latches, NAND gates, NOR gates, inverters, EXCLUSIVE OR gates and EXCLUSIVE NOR gates. Each latch, or flip-flop, as such are also commonly referred to, such as the one shown schematically as element 106A in lower left hand corner of FIG. 6A, is designated as a rectangle having longer vertical sides. Inputs to each latch are from the left side with the upper input being a data input and the lower input being a clock input. The outputs of the latch are taken from the right side with the upper output being the conventional "Q" output, and the lower line representing the conventional "$\bar{Q}$" output. For selected latches, a set and a reset input are provided with the reset input being applied to the bottom of the rectangle and the set input being applied to the top of the rectangle. In operation, any logic "1" signal applied to the reset input causes the Q output to assume a logic "0" state and the $\bar{Q}$ output to assume a logic "1" state. Conversely, any logic "1" signal applied to the set input causes the Q output to assume a logic "1" state, and the $\bar{Q}$ output to assume a logic "0" state. Whenever a signal which changes from logic "0" to logic "1" is applied to the clock input, the Q output assumes a logic value equal to the logic value of the signal applied to the data input and the $\bar{Q}$ output assumes the opposite logic value.

A NAND gate is shown schematically as element 106B in the lower left-hand corner of FIG. 6A and includes two or more inputs and one output. The output of a NAND gate is normally a logic "1" signal unless the signals applied to each of the inputs thereof are logic "1", in which case the output of the NAND gate is a logic "0" signal.

An inverter is shown schematically as element 106C in the lower left-hand corner of FIG. 6A and has one input and one output with the output providing a signal having a logic value opposite to that of the signal applied to the input.

A NOR gate is shown schematically as element 114A in the lower center portion of FIG. 6A and has two or more inputs and one output. The signal at the output of a NOR gate is normally logic "0" unless the signals applied to each of the inputs are all logic "0" in which case the signal at the output is a logic "1".

An EXCLUSIVE OR gate is shown schematically as element 124A in FIG. 6C and has at least two inputs and one output. The output signal is a logic "1" if signals with different logic values are applied to the inputs thereof, and a logic "0" if the signals applied to the inputs all have the same logic value.

Figure 6B:
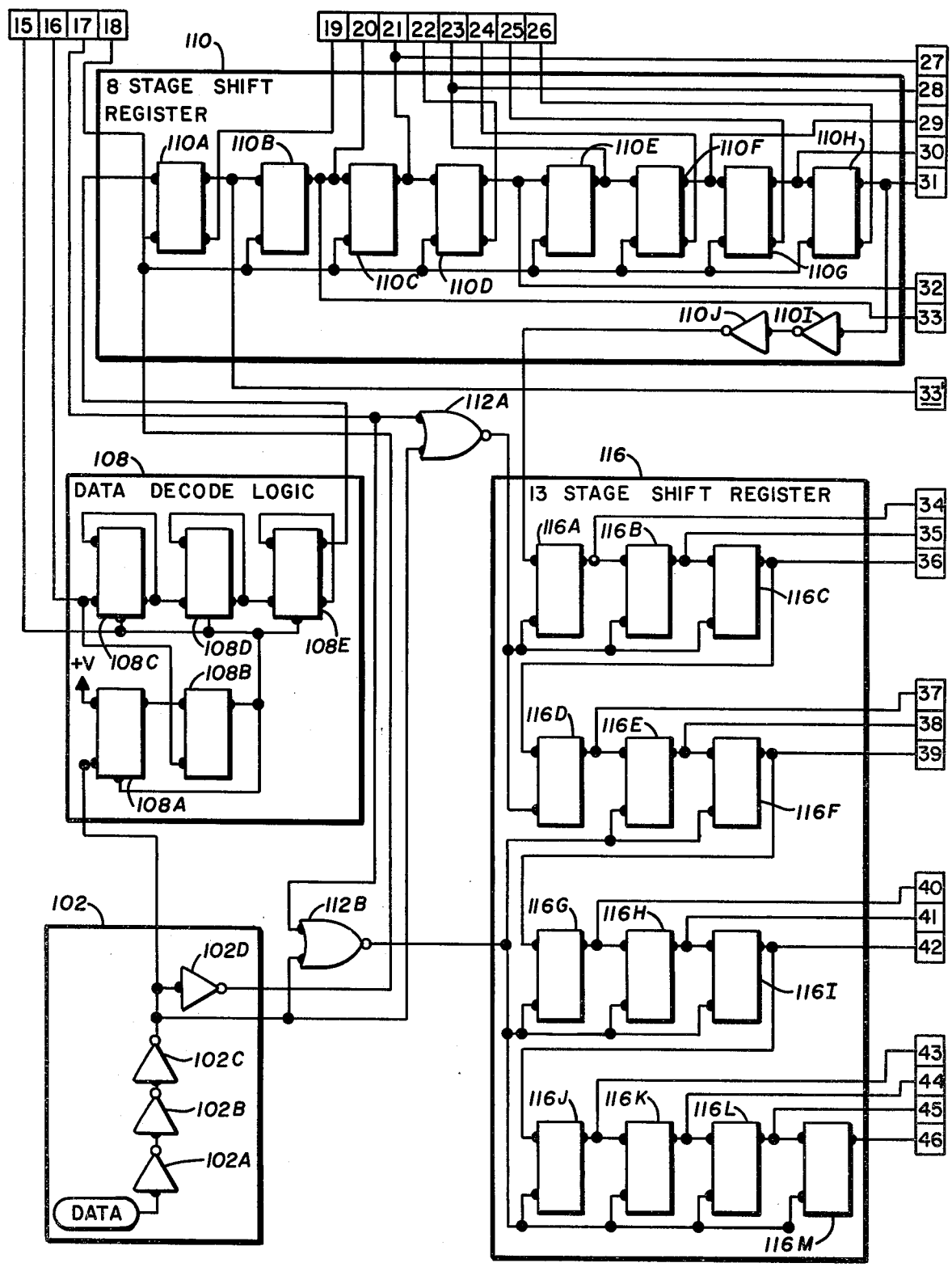
Figure 60:
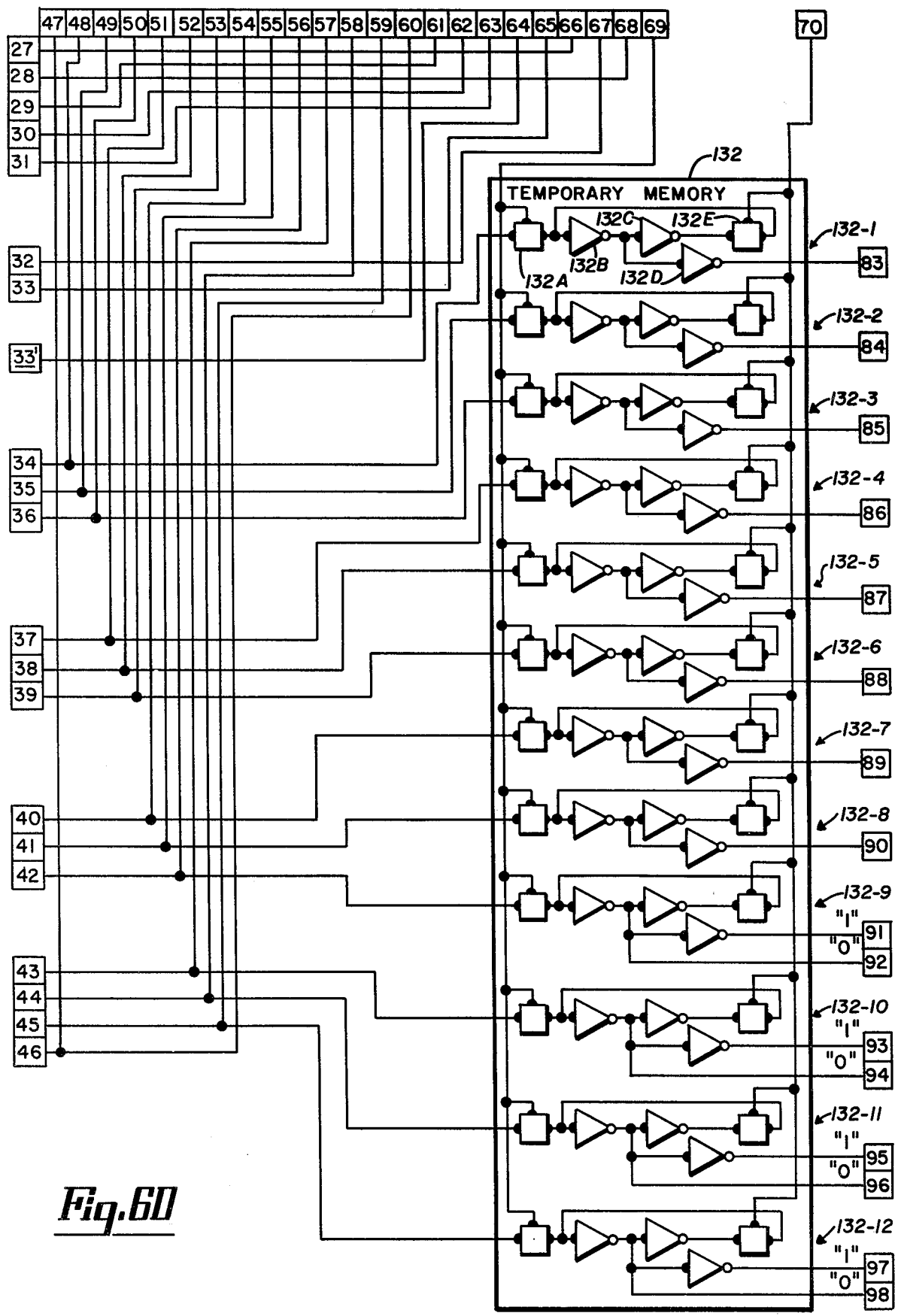
Figure 6F:
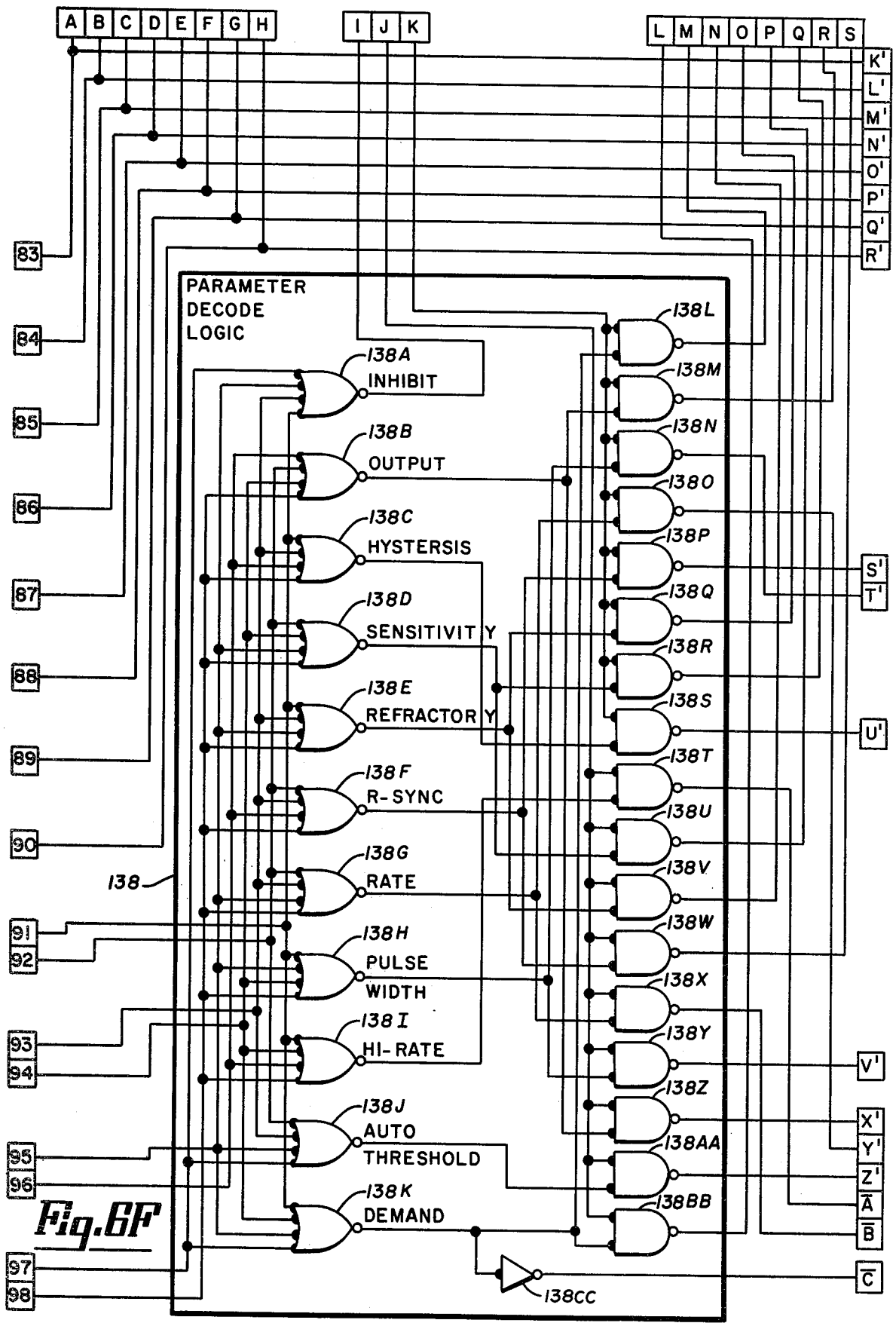
Figure 6G:
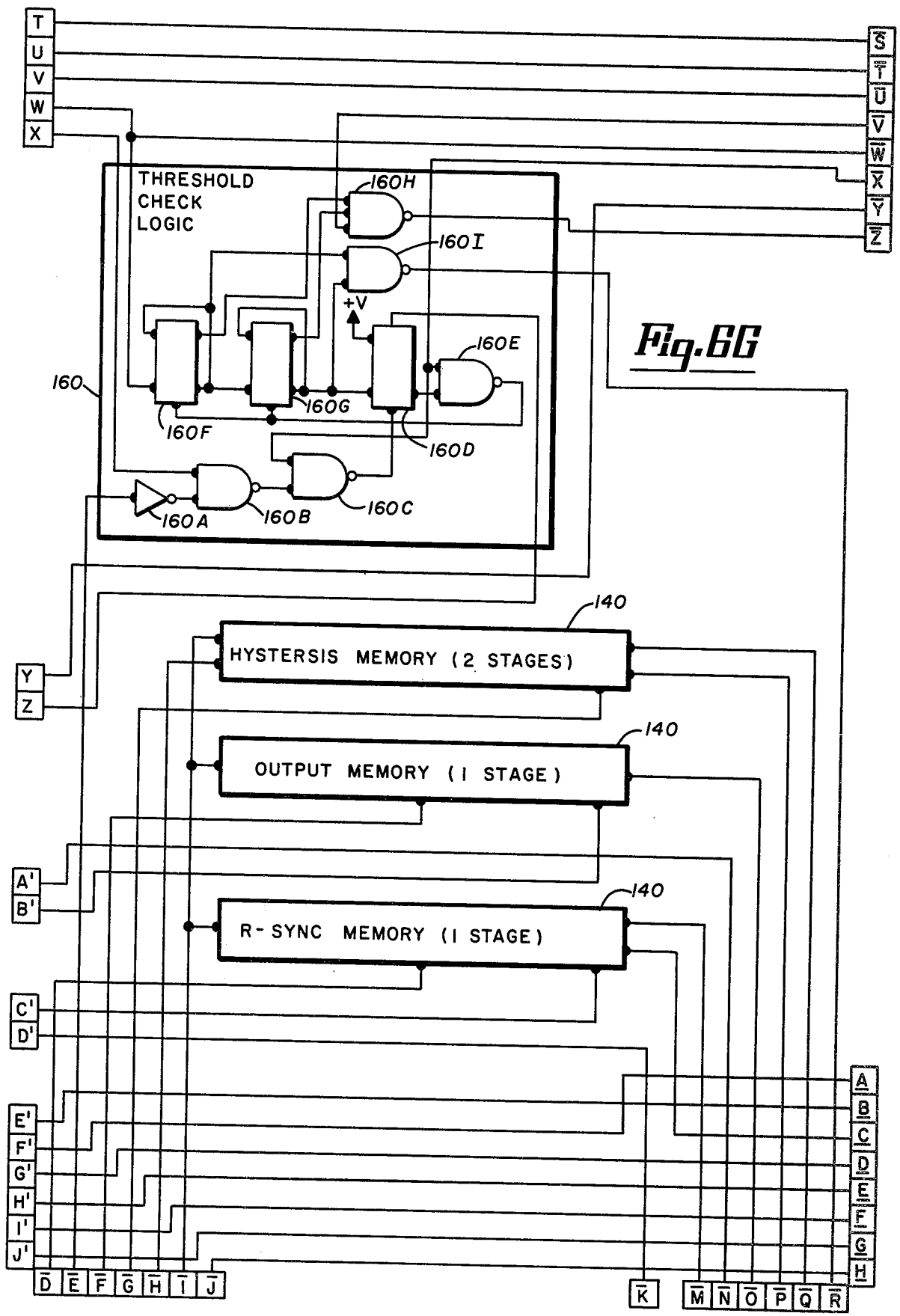
Figure 6H:
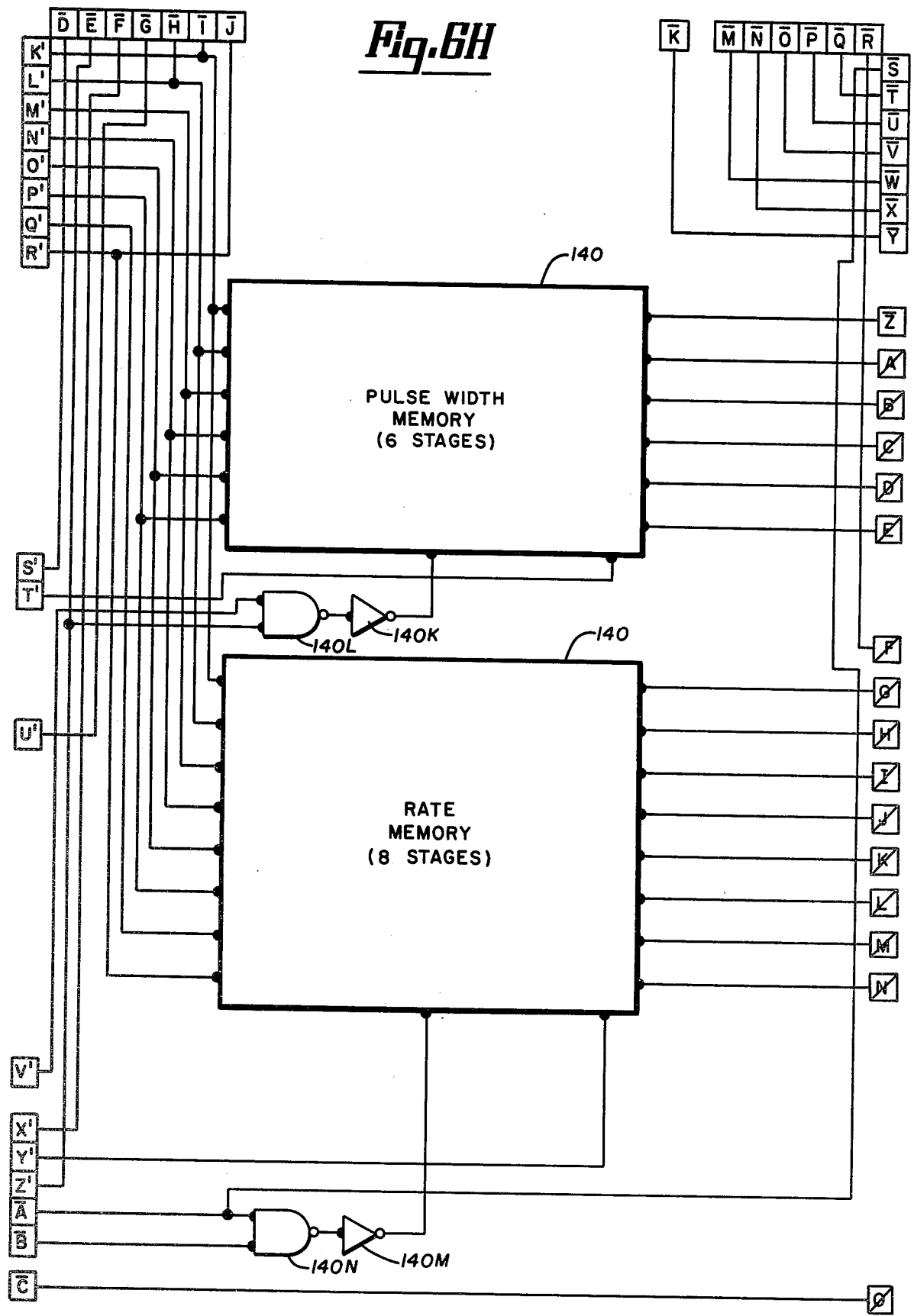
Figure 6I:
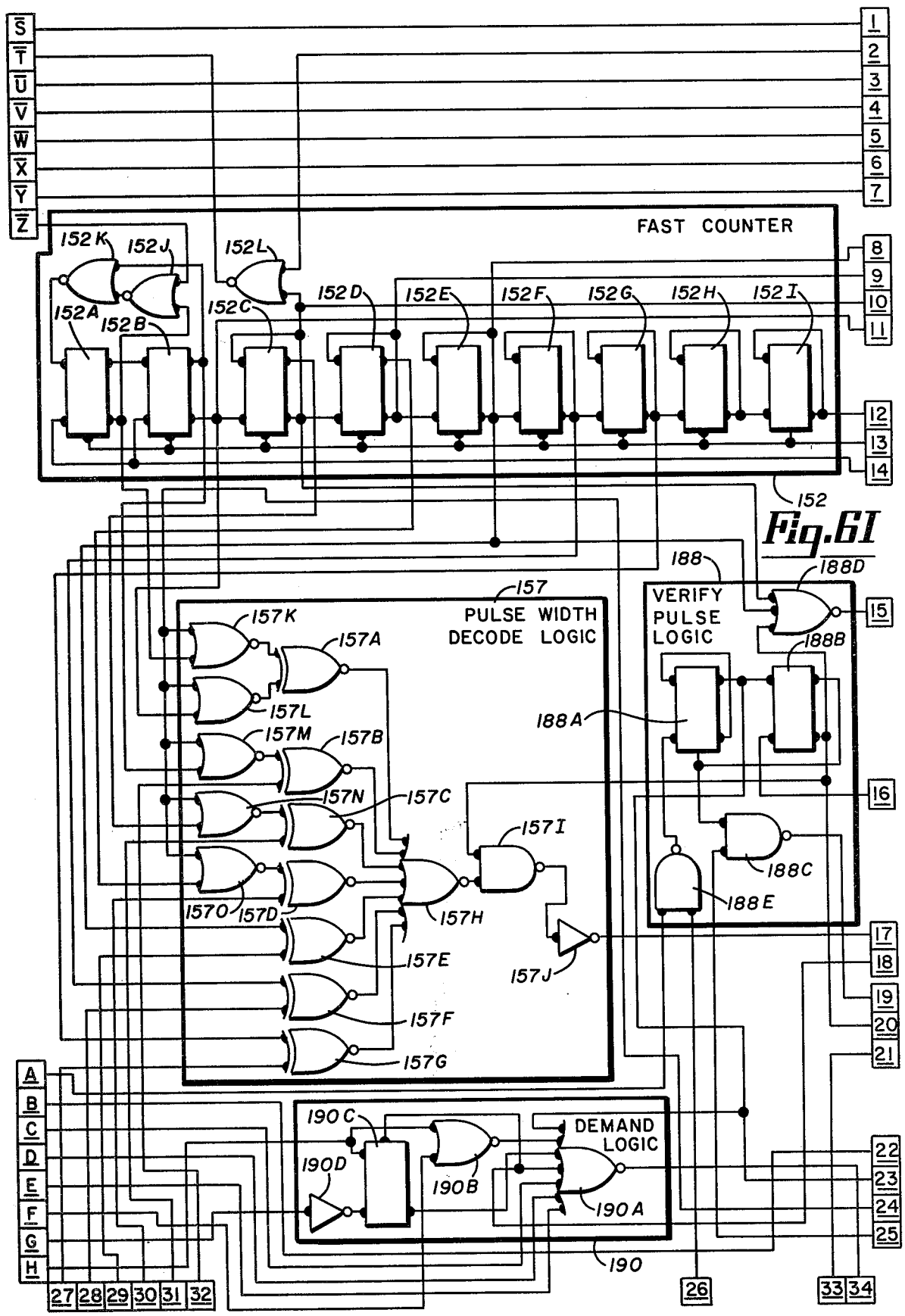

An EXCLUSIVE NOR gate is shown schematically as element 157A in FIG. 6I and has at least two inputs and an output. The output signal is a logic "0" if signals with different logic values are applied to the inputs thereof, and a logic "1" if signals having the same logic value are applied to the inputs thereof.

Referring now to FIGS. 6A through 6N assembled as shown in FIG. 6, a detailed description of pulse generator 16 will now be given. In FIG. 6B, the DATA signal from analog circuit 42 is provided through serially coupled inverters 102A, 102B, 102C and 102D, so that the signal at the output of inverter 102C is of opposite polarity to the DATA signal, that is normally logic "1"

signal with logic "0" pulses, and the signal at the output of inverter 102D is the same polarity as the DATA signal, that is a normally logic "0" signal with logic "1" pulses.

The output from inverter 102C is applied to one input of NOR gates 112A and 112B. The output from inverter 102D is applied to the clock inputs of each of the eight latches 110A through 110H inclusive forming eight stage shift register 110. In addition, the output of inverter 102D is coupled to the reset input of latch 106A in reset to 24 logic 106.

The output from inverter 102C is also applied to the clock input of latch 108A in data decode logic 108. The data input to latch 108A is coupled to +V voltage from battery 44, shown in FIG. 4. The Q output from latch 108A is coupled to the data input of latch 108B. The clock input of latch 108B is the fast clock signal applied from the output of NOR gate 152L in fast counter 152, shown in FIG. 6I. As previously noted, the fast clock signal is a clock signal having a frequency of 4,096 hz. The Q output from latch 108B is applied to the reset input of latch 108A. In operation, latches 108A and 108B cause a pulse signal, synchronized with the fast clock signal, to be provided at the Q output of latch 108B, at a time coincident with the leading edge of the first fast clock pulse following the trailing edge of each DATA pulse. More specifically, the output from inverter 102C is a series of DATA signal pulses having a rising edge at the trailing edge of each pulse. Thus, the trailing edge of each DATA signal pulse causes latch 108A to become set which then enables latch 108B to become set upon the occurrence of the leading edge of the next fast clock pulse. When latch 108B is set, the logic "1" Q output signal therefrom resets latch 108A removing the logic "1" signal from the data input of latch 108B. Thus, the leading edge of the next fast pulse causes latch 108B to become reset and the Q output signal becomes logic "0". Thus, the signal at the Q output of latch 108B corresponds to the data clock signal at the upper output of data decode logic 108 shown in FIG. 5A.

Data code circuit 108 also includes the three latches 108C, 108D, and 108E forming a three stage binary counter. Each of latches 108C, 108D and 108E has the $\overline{Q}$ output thereof coupled to the data input thereof. The clock input of latch 108C is coupled to the fast clock signal from NOR gate 152L in the fast counter 152 shown in FIG. 6I. The $\overline{Q}$ output from latch 108C is coupled to the clock input of latch 108D and the $\overline{Q}$ output from latch 108D is coupled to the clock input of latch 108E. The output from the data decode circuit 108 is taken from the Q output of latch 108E. Further, the reset inputs of each of latches 108C, 108D and 108E are coupled to the Q output from latch 108B, so that immediately after the occurrence of each DATA signal pulse, each of latches 108C, 108D and 108E are reset. Latches 108C, 108D and 108E then commence counting of the fast clock signals and after four such fast clock signals are applied to the input of latch 108C, the Q output of latch 108E becomes logic "1", unless of course latches 108C, 108D and 108E have been reset in the interim by a pulse from latch 108B. Thus, if two successive DATA signal pulses are separated by a time less than the time required for latches 108C, 108D and 108E to count four fast clock signal pulses, data decode logic 108 will decode a logic "0" signal as the output of latch 108E at the time the leading edge of the next DATA signal pulse occurs. On the other hand, if a longer time period exists between successive DATA signal pulses, the Q output of latch 108E will be logic "1" and thus data decode circuit 108 will manifest a logic "1" bit as the data bit. Thus, the Q output of latch 108E corresponds to the decoded data value from the lower output of data decode logic 108 in FIG. 5A.

The data at the Q output of latch 108E from data decode logic 108 is applied to the data input of latch 110A in eight stage shift register 110. Eight stage shift register 110 includes latches 110A, 110B, 110C, 110D, 110E, 110F, 110G and 110H and inverters 110I and 110J. The clock inputs of each of latches 110A through 110H are coupled to the output of inverter 102D. The data input of each of stages 110B through 110H is coupled to the Q output of each of the preceding stages 110A through 110G. The Q output of latch 110H is coupled through serially connected inverters 110I and 110J to the data input of thirteen stage shift register 116 and specifically the data input of latch 116A, therein.

Eight stage shift register 110 operates such that the logic value of the signal applied to the data input of latch 110A is shifted through the eight stages, one at a time, each time the leading edge of the DATA signal pulses are provided from inverter 102D. It should be noted that the first data pulse provided will result in a meaningless data bit being shifted into eight stage shift register 110. However, as will be explained hereafter, this bit as well as the first three real data bits will be shifted entirely through eight stage shift register 110 and entirely through thirteen stage shift register 116 and will not be stored nor utilized as part of the programming code.

Thirteen stage shift register 116 includes thirteen latch circuits, 116A through 116M. Stages 116A through 116D each has its clock input coupled to the output of NOR gate 112A and stages 116E through 116M each has its clock input coupled to the output of NOR gate 112B. NOR gates 112A and 112B each have one input coupled to the output of inverter 102C and a second input coupled to the output of access code check logic 114 and, specifically, the Q output of latch 114D therein. The Q output of each of the stages 116A through 116L is coupled to the data input of the next succeeding stage 116B through 116M of thirteen stage shift register 116.

As long as NOR gates 112A and 112B are enabled by a logic "0" signal being applied thereto from access code check logic 114, the data that is applied from the eighth stage 110H of eight stage shift register 110 will be shifted through thirteen stage shift register 116. Thus, at the time the access code has been fully transmitted after twenty-four bits of the thirty-two bit programming signal, the access code will be in the eight stages of shift register 110 and the thirteen most significant data bits of the remaining sixteen data bits will be in thirteen stage shift register 116, the three least significant data bits having been shifted out of thirteen stage shift register 116. Specifically, in thirteen stage shift register 116 stages 116A through 116H will contain the data portion of the programming code, stages 116I through 116L will contain the parameter portion of the programming code, and stage 116M will contain a data bit indicating whether a permanent or temporary programming change is to occur.

Referring now to FIG. 6A and specifically access code check logic 114, the $\overline{Q}$ outputs from stages 110A, 110D, 110F, 110G and 110H and the Q outputs from stages 110B, 110C and 110E are each coupled as inputs to NOR gate 114A. Whenever the state of eight stage shift register is octal "227", each of the inputs to NOR gate 114A will be a logic "0" and the output thereof will be a logic "1". It should be noted that octal "227" is the access code and eight stage shift register 110 will assume the state of the access code after twenty-four data values, defined by the leading edge of the twenty-fifth DATA signal pulse, have been applied thereto. When each of the signals applied to NOR gate 114A are logic "0", the output thereof will be logic "1". The output of NOR gate 114A is coupled as one input to the NAND gate 114B. The other input of NAND gate 114B is coupled to an output from pulse counter 118 which is a logic "0" until after the count in pulse counter 118 equals or exceeds twenty-four, or in other words, until after the access code has been applied to eight stage shift register 110. Thus, the output of NAND gate 114B which is a logic "1" prior to detecting the access code, is applied as one input to NAND gate 114C, the other input of which is the $\overline{Q}$ signal from latch 114D, which prior to detecting the access code is a logic "1". The output of NAND gate 114C, which will be a logic "0" prior to detecting the access code, is applied to the data input of latch 114D. The clock input to latch 114D is coupled to the data clock signal from the Q output of latch 108B in data decode logic 108 so that a pulse is applied to the clock input of latch 114D just after the trailing edge of each DATA signal pulse occurs. After the access code has been stored in eight stage shift register 110, both inputs to NAND gate 114B will be logic "1" and the output thereof becomes logic "0". Hence the output from NAND gate 114C, and the data input to latch 114D become logic "1". This occurs at the leading edge of the DATA signal pulse defining the last bit of the access code. At the trailing edge of that same DATA signal pulse a logic "1" pulse signal is applied to the clock input of latch 114D, causing latch 114D to become set, since as the output of NAND gate 114C is then logic "1". This causes the Q output thereof to become logic "1" and the $\overline{Q}$ output to become logic "0", which in turn maintains the output of NAND gate 114C at a logic "1" and thereby maintain latch 114D set as additional DATA signal pulses are applied. The Q output from latch 114D is also applied to disable NOR gates 112A and 112B in FIG. 6B from passing any further clock pulses to thirteen stage shift register 116, thereby maintaining the parameter and data values stored therein at the time the access code is detected.

Pulse counter 118 counts each applied DATA signal pulse. Pulse counter 118 includes latches 118A, 118B, 118C, 118D and 118E arranged as a conventional binary counter; that is, with the $\overline{Q}$ input of each latch being coupled to the data input of that latch and to the clock input of the next succeeding latch. The signal to the clock input to latch 118A, the first stage of the pulse counter, is applied from the output of latch 108B and is the data clock pulse which occurs in synchronism with the fast clock signal just after the trailing edge of each DATA signal pulse. Pulse counter 118 also includes a NOR gate 118F having two inputs respectively coupled to the $\overline{Q}$ outputs of latches 118D and 118E. Connected in this manner, the output of NOR gate 118F is a logic "0" until the count in pulse counter 118 reaches twenty-four, that is, until both latches 118D and 118E are set. At this point the output of NOR gate 118F becomes logic "1", thereby enabling NAND gate 114B in access code check logic 114 to pass any outputs from the access code check gate 114A. It should be noted that NOR gate 118F continues providing a logic "1" signal as the count of pulses counter 118 exceeds a count of twenty-four.

Pulse counter 118 also includes NOR gate 118G having five inputs respectively coupled to the Q outputs of each of latches 118A through 118E. The output of NOR gate 118G is normally logic "1" and becomes logic "0" whenever count of pulse counter 118 is at a nonzero count. This signal is applied to timeout logic 120 shown in FIG. 6C to cause pulse counter 118 to be automatically reset after two stimulating pulses have been provided by pulse generator 16 if the applied programming signal has not been accepted by that time. Such a situation could occur when an extraneous signal is detected by the demodulator and applied as a DATA pulse.

As previously mentioned, access code check logic 114 normally causes a signal to be provided from the Q output of latch 114D after the twenty-fourth data bit has been applied to pulse generator 16. It should also be recalled that the twenty-fourth data bit will be defined by the leading edge of the twenty-fifth DATA signal pulse. However, it is possible that in positioning head 14 over pulse generator 16 extraneous noise may be generated that could be construed by the RF demodulator circuitry included in circuit 42 as pulse bursts and, hence, additional pulses could be included in the DATA signal applied to pulse generator 16 and counted by pulse counter 118. In any event, when the access code is found, it signifies that twenty-four bits have been applied and it is desirable to reset pulse counter 118 to a count of twenty-four.

Reset to twenty-four logic 106 is provided to reset pulse counter 118 to a count of twenty-four and includes latch 106A, NAND gate 106B and inverter 106C. Latch 106A has the source of positive voltage +V coupled to its data input and the output from latch 114D coupled to its clock input. The $\overline{Q}$ output from latch 106A is coupled to one input of NAND gate 106B, the other input being the output of inverter 106C. A normally logic "0" signal is applied to inverter 106C from reset logic 126 and hence the output of inverter 106C is a logic "1" signal maintaining NAND gate 106B enabled. In addition, latch 106A has a reset input coupled to the output of inverter 102D so that latch 106A is reset each time a DATA signal pulse is applied to pulse generator 16.

When access code check logic 114 senses the access code and the Q output of latch 114D becomes logic "1", latch 106A is clocked to a set state. The then logic "0" $\overline{Q}$ signal from latch 106A causes the output of NAND gate 106B to become logic "1". The output of NAND gate 106B is applied to the reset inputs of latches 118A, 118B and 118C in pulse counter 118 and the Q output of latch 106A is applied to the set input of latch 118D. Thus, when latch 106A is set and the output of NAND gate 106B becoming logic "1", latches 118A, 118B and 118C become reset and latch 118D becomes set and pulse counter 118 is forced set to a count of twenty-four.

After the access code is decoded by access code check logic 114 and NOR gates 112A and 112B are disabled from passing further clock pulses to thirteen stage shift register 116, the remaining portion of the DATA signal manifests the eight bit parity code. This code is then stored in eight stage shift register 110 and the access code previously stored therein is shifted out and lost. During this period pulse counter 118 continues to be incremented during the transmission of the eight parity bits. After the eight parity bits have been transmitted, pulse counter 118 overflows back to a count of zero. At the time this happens, the $\overline{Q}$ output from latch 118E will go from a logic "0" value to a logic "1" value, thereby causing a logic "0" to appear at the output of NOR gate 118F. This logic "0" is applied through NAND gates 114B and 114C to the data input of latch 114D as a logic "0" signal. Thus, if any further DATA signal pulses are transmitted, a logic "0" will be clocked into latch 114D causing the Q output thereof to become logic "0". However, under normal circumstances, this should not occur.

The $\overline{Q}$ output from latch 118E in pulse counter 118 is applied to counter overflow latch 104 and specifically to the clock input of latch 104A therein. The data input to latch 104A is coupled to battery 44 voltage of $+V$ volts. When pulse counter 118 overflows to a count of zero after the parity code is transmitted, thereby causing the $\overline{Q}$ signal from latch 118E to change from logic "0" to logic "1", latch 104A becomes set, and the $\overline{Q}$ output thereof becomes logic "0". The $\overline{Q}$ signal from latch 104A is provided to enable gates within error check logic 122 to check the parity of the transmitted DATA signal.

Referring now to FIG. 6C and specifically parity check logic 124, there is included thirteen two input EXCLUSIVE OR gates 124A through 124M and a single eight input NOR gate 124N. Parity check logic 124 is responsive to the Q outputs from each stage of eight stage shift register 110 and to the Q outputs of each stage of thirteen stage shift register 116. Specifically, EXCLUSIVE OR gate 124A is responsive to Q output signals from latches 116F and 110F, EXCLUSIVE OR gate 124B is responsive to Q output signals from latches 116G and 110G, EXCLUSIVE OR gate 124C is responsive to Q output signals from latches 116H and 110H, EXCLUSIVE OR gate 124D is responsive to Q output signals from latches 116A and 116I, EXCLUSIVE OR gate 124E is responsive to Q output signals from latches 116B and 116J, EXCLUSIVE OR gate 124F is responsive to the Q output signals from latches 116C and 116K, EXCLUSIVE OR gate 124G is responsive to the Q output signals from latches 116D and 116L and EXCLUSIVE OR gate 124H is responsive to the Q output signals from latches 116E and 116M. In addition, EXCLUSIVE OR gate 124I is responsive to the output signals from EXCLUSIVE OR gate 124D and to the Q output of latch 110A, EXCLUSIVE OR gate 124J is responsive to the output signals from EXCLUSIVE OR gate 124E and to the Q output from latch 110B, EXCLUSIVE OR gate 124K is responsive to the output signals from EXCLUSIVE OR gate 124F and the Q output from latch 110C, EXCLUSIVE OR gate 124L is responsive to the output signals from EXCLUSIVE OR gate 124G and the Q output from latch 110D and EXCLUSIVE OR gate 124M is responsive to the output signals from EXCLUSIVE OR gate 124H and the Q output from latch 110E. The output signals from each of EXCLUSIVE OR gates 124A, 124B, 124C, 124I, 124J, 124K, 124L and 124M are applied as the inputs to NOR gate 124N, the output of which is applied as one input to NAND gate 122A in error check logic 122, shown in FIG. 6A. The parity code applied to and stored in eight stage shift register 110 is calculated to be such that the output of NOR gate 124N will be logic "1" when the data stored in thirteen stage shift register 116 is compared against the parity code by EXCLUSIVE OR gates 124A through 124M.

Referring again to FIG. 6A and specifically to error check logic 122, there is included NAND gate 122A, inverter 122B, NOR gates 122C and 122D and latches 122E and 122F. The other input to NAND gate 122A in error check logic 122 is coupled to the Q output of latch 114D, which should be logic "1", assuming the access code was detected. If the parity also checks, the output of NAND gate 122A is logic "0" which, when applied through inverter 122B, becomes logic "1". The output of inverter 122B is applied to one input of NOR gate 122C and the output of NAND gate 122A is applied to one input to NOR gate 122D. The other input of NOR gates 122C and 122D is coupled to the $\overline{Q}$ output of latch 104A in counter overflow latch 104, which as previously explained should be a logic "0" signal if the proper number of DATA signal pulses have been counted by pulse counter 118. Thus, if the access code is detected by access code check logic 114, the parity is proper, as determined by parity check logic 124, and pulse counter 118 has counted at least thirty-two pulses thereby setting counter overflow latch 104A, then the output from NOR gate 122D will be a logic "1". In the event that any one or more of these checks fail, the output from NOR gate 122C will be a logic "1", which indicates that an error has occurred.

The output from NOR gate 122C is applied to the data input of latch 122E and the output from NOR gate 122D is applied to the data input of latch 122F. The clock inputs of both latches 122E and 122F are coupled to the slow clock logic 154 signal from FIG. 6K. Only one of latches 122E or 122F will be set depending on which one of NOR gates 122C or 122D applies a logic "1" signal to the data input thereof. If all checks are met, latch 122F will be set, thereby causing the Q output to become logic "1" and the $\overline{Q}$ output to become logic "0". These two outputs are the accept signal and manifest to the remainder of the circuitry shown in FIGS. 6A through 6N that DATA signal has been accepted. On the other hand, if one or more of the checks fail, latch 122E will become set and the $\overline{Q}$ output signal therefrom will become logic "0". This signal is the error signal from error check logic 122 and will indicate that an error occurred in the transmission or reception of the DATA signal.

The Q outputs from each of latches 122E and 122F are applied as inputs to NAND gate 104B in counter overflow latch 104, and the output of NAND gate 104B is applied to the reset of latch 104A. As long as both latches 122E and 122F remain reset, the output from NAND gate 104B is a logic "0". However, as soon as one of the two latches 122E or 122F are set, the output from NAND gate 104B becomes logic "1", thereby resetting counter overflow latch 104A. This, in turn, causes the outputs of both NOR gate 122C and 122D to become logic "0" and the next slow clock logic 154 signal pulse resets the set one of latches 122E and 122F. Thus, the error or accept signal from latches 122E and 122F, respectively, is a pulse signal having a duration of one slow clock cycle.

In the event error check logic 122 determines that an error occurred in the transmission or detection of the DATA signal, it is desirable to reset much of the logic shown in FIGS. 6A and 6B. This is accomplished by providing the $\overline{Q}$ output from latch 122E to one input NAND gate 126A in reset logic 126. The other two inputs to NAND gate 126A are coupled to the outputs from reed switch logic 159 shown in FIG. 6M and timeout logic 120 shown in FIG. 6D. Whenever reed switch 46 is closed, the reed switch logic 159 signal applied to NAND gate 126A will be a logic "1" and normally the signal from timeout logic 120 will be a logic "1". Hence, the output from NAND gate 126A is a logic "0" signal which is inverted by inverter 126B and applied as one input to NAND gate 126C. The other input to NAND gate 126C is a normally logic "1" signal from write latch 128, which becomes logic "0" for one slow clock signal time period after write latch 128 is set.

The output of NAND gate 126C will become logic "1" whenever any one or more of the reed switch signal, timeout logic 120 signal, the error signal from latch 122E or write latch signal becomes logic "0". In addition, a logic "1" signal will be provided from the output of NAND gate 126A whenever any one of the reed switch, timeout logic 140 or error signals from latch 122E become logic "0". The output from NAND gate 126C is applied to reset latches 118D and 118E in pulse counter 118, to reset the access code latch 114D and through inverter 106C and NAND gate 106B to reset latches 118A, 118B and 118C in pulse counter 118.

In the event that error check logic 122 finds that all of the checks are met, latch 122F will be set. The Q output from latch 122F is applied to the data input of write latch 128A and to the clock input of test latch 130A. The slow clock signal is applied to the clock input of write latch 128A and the Q output from latch 116M in thirteen stage shift register 116 is applied to the data input of test latch 130A. The output from NAND gate 126A in reset logic 126 is applied to the reset input of test latch 130A and resets it each time the reed switch is open or timeout logic 120 provides a signal to NAND gate 126A or an error is found and latch 122E is set.

Write latch 128A is set upon the occurrence of the first slow clock pulse following the setting of latch 122F (manifesting an acceptance of the DATA signal). When write latch 128A is set, the $\overline{Q}$ output becomes logic "0" and is applied through NAND gate 126C in reset logic 126 to cause a resetting of pulse counter 118 and latch 114D. The Q output from write latch 128A, which becomes logic "1", is applied to the inhibit logic 134 shown in FIG. 6C.

Test latch 130A is clocked upon the occurrence of the logic "1" signal from latch 122F and becomes set if the data value stored in latch 116M of thirteen stage shift register 116 is a logic "1", manifesting that a temporary programming condition is to occur. The Q output from test latch 130A is applied as one input to memory strobe NOR gate 136A. The other input to NOR gate 136A is the $\overline{Q}$ output from write latch 128A. The output of NOR gate 136A will be a logic "1" only if write latch 128A is set and test latch 130A is not set, that is, only when a DATA signal has been accepted and the decoding of the test bit indicates that a permanent programming change is to occur. The output of memory strobe gate 136A is applied to parameter decode logic 138 in FIG. 6F to cause a permanent parameter signal to be provided therefrom. In addition, the Q output from test latch 130A is also applied to parameter decode logic 138 and when the Q output from test latch 130A is a logic "1", parameter decode 138 will provide a temporary parameter signal. The particular parameter signal provided will be determined by the data stored in latches 116I, 116J, 116K and 116L of thirteen stage shift register 116.

Referring now to FIG. 6D, temporary memory 132 is shown and includes twelve stages, 132-1 through 132-12 inclusive, each of which are identical. For convenience, only first stage 132-1 will be described. It is understood that all other stages and the components thereof are identical to and operate in the same manner as first stage 132-1. The first stage 132-1 of temporary memory 132 includes transmission gate 132A, inverters 132B, 132C and 132D, and a transmission gate 132E. A transmission gate, as used herein, is a gate which may be enabled by a logic "1" signal applied to the enable input thereof to cause the signal applied to the data input thereof to be provided at the output thereof. Schematically, a transmission gate is shown as a square with the input side receiving the data input, the output side providing the output and either the top or bottom side receiving the enable input.

Transmission gate 132A has applied to its data input, the signal from the Q output from latch 116A in thirteen stage shift register 116. Each of the remaining transmission gates corresponding to gate 132A is responsive to one of the Q outputs from a corresponding latch 116B through 116L. It should be noted that the Q output signal from latch 116M from thirteen stage shift register 116 is not applied to temporary memory 132. The output from transmission gate 132A is applied to the input of inverter 132B, the output of which is applied to the inputs of inverters 132C and 132D. The output of inverter 132C is applied to the input of transmission gate 132E, the output of which is applied back to the junction between the output of transmission gate 132A and the input of inverter 132B. Transmission gate 132A is enabled by a logic "1" accept signal from the Q output of latch 122F and transmission gate 132E is enabled by a logic "1" signal from the $\overline{Q}$ output of latch 122F. The output from stage 132-1 of temporary memory 132 is taken from the output of inverter 132D. In stages 132-2 through 132-12, outputs are taken from each stage from the inverter corresponding to inverter 132D. In addition, in the last four stages 132-9 through 132-12 of temporary memory 132, a second output is taken from the output of the inverter corresponding to inverter 132B.

Each stage of temporary 132 operates as follows. Inverters 132B, 132C and normally enabled transmission gate 132D form a memory circuit in that the signal applied to inverter 132B is twice inverted and applied at the output of transmission gate 132E where it is fedback to maintain the same signal at the input of inverter 132B. This situation continues as long as transmission gate 132E is enabled by the latch 122F being reset. When latch 122F becomes set as a result of the acceptance of the DATA signal, the Q output thereof is logic "1" for the time between slow clock pulses and transmission gate 132A is enabled and transmission gate 132E is disabled. During this one pulse time, the signal provided at the Q output of latch 116A in thirteen stage shift register 116 is applied through transmission gate 132A, inverted by inverter 132B and again inverted by inverter 132C. After the slow clock signal pulse period, when latch 122F becomes again reset, transmission gate 132A again becomes disabled and transmission gate 132E again becomes enabled and thereby feeds back the signal at the output of inverter 132C to the input of 132B and is stored in the memory circuit formed by inverters 132B, 132C and transmission gate 132E. In this manner the data that is stored in thirteen stage shift register 116 is transmitted to temporary memory 132 each time a new programming signal is accepted and latch 122F is set. Since the transmission gates corresponding to transmission gates 132A and 132E are enabled and disabled by the same signals from latch 122F, the storage by temporary memory 132 of the twelve data bits in thirteen stage register 116 occurs simultaneously. Further, since the output of each stage of temporary memory 132 is taken between inverters 132B and 132C, it is necessary to reinvert the signal by inverter 132D to make the signal provided from inverter 132D the same at the signal provided through transmission gate 132A. In the case of the last four stages 132-9 through 132-12 of temporary memory 132 which store the data bits relating to the parameter code, an additional output is taken directly from the junction of inverters 132B and 132C. In the last four stages 132-9 through 132-12, the signal from the inverter gate corresonding to inverter gate 132D is labled as the "1" output and the signal from the junction corresponding to the junction between inverters 132B and 132C is labeled as the "0" output.

Referring now to inhibit logic 134 timeout logic 120 and inhibit data code 142 in FIG. 6C, inhibit data decode 142 includes eight input NAND gate 142A having an input coupled to each of the first eight stages of temporary memory 132. These stages store the data portion of the data word transmitted to pulse generator 116. Whenever the data portion of the code is all logic "1"s or octal "377", the output from NAND gate 142A is logic "0". Otherwise it is a logic "1".

Inhibit logic 134 includes NAND gate 134A, NOR gate 134B and latch 134C. One input to NAND gate 134A is provided from the inhibit parameter signal out of parameter decode circuit 138 shown in FIG. 6F and the second input to NAND gate 134A is provided from the Q output of test latch 130A. The output from NAND gate 134A is provided as one input to NOR gate 134B, the other input of which is provided from the output of inhibit data decode NAND gate 142A. The output of NOR gate 134B is coupled to the data input of latch 134C. The clock input to latch 134C is provided from the Q output of write latch 128A. The reset input of latch 134C is coupled to the output of NAND gate 126A in reset logic 126 and latch 134C is reset each time reed switch is closed, a signal is provided from timeout logic 120, or an error is sensed in the received DATA signal and latch 122E is set.

Timeout logic 120 includes NAND gates 120A, 120B and 120C, each of which have two inputs and an output and latches 120D and 120E. The $\overline{Q}$ output from latch 134C is applied as one input of NAND gate 120A, and the output of NOR gate 118G from pulse counter 118 is applied to the other input of NAND gate 120A. The Q output from latch 134C is applied to one input of NAND gate 120B, and the accept signal from the Q output of latch 128A is applied to the other input of NAND gate 120B. The outputs from NAND gates 120A and 120B are coupled as the two inputs to NAND gate 120C, the output of which is coupled to the reset inputs of each of latch 120D and 120E. Latches 120D and 120E are coupled as a two stage counter, that is the $\overline{Q}$ output of each is coupled to the data input thereof, and the $\overline{Q}$ output of latch 120D is additionally coupled as the clock input of latch 120E. The clock input of latch 120D is coupled to the recharge logic 164 signal which is a logic "1" pulse signal each time a recharge pulse is provided from digital circuit 40 to analog circuit 42. The $\overline{Q}$ output from latch 120E is additionally applied as the timeout signal to NAND gate 126A to cause a reset signal to be provided whenever latches 120D and 120E are not reset prior to the occurrence of two pulse width logic 186 signals.

In normal operation inhibit logic latch 134C is reset and pulse counter 118 contains a count of zero and thus the output of NOR gate 118G is logic "0". Hence, the timeout logic counter consisting of latches 120D and 120E is maintained reset by a logic "1" signal appearing at the output of NAND gate 120C. However, in two instances it is possible to remove logic "1" from the reset inputs of latches 120D and 120E. These instances are first, that inhibit logic 134 has properly decoded an inhibit programming signal and second, that pulse counter 118 is not reset.

Referring to the inhibit programming situation, it should be recalled from Table I above that the inhibit feature can only be programmed in the temporary mode and must be accompanied with a data portion of the programming word of octal "377", or all logic "1" bits. The "377" data portion of the programming word is decoded by inhibit data decode logic 142 shown in FIG. 6E and a logic "0" bit is provided from NAND gate 142A to one input of NOR gate 134B. The inhibit parameter which is decoded by the parameter decode 138 is provided as a logic "1" to NAND gate 134B. Since the inhibit feature must be in the temporary mode, test latch 130A will be set and the Q output therefrom provided to NAND gate 134A will be a logic "1". Also, the inhibit parameter signal from parameter decode logic 138 becomes logic "1" whenever the inhibit feature is programmed. Thus, the output of NAND gate 134A to be a logic "0", which together with logic "0" provided from gate 142A causes the output of NOR gate 134B to be logic "1". When the write latch 128A is set by the next occurring slow clock pulse, it will set latch 134C to manifest the then applied logic "1" signal at the data input thereof, thereby causing the Q output to become logic "1" and the $\overline{Q}$ output to become logic "0". The logic "0" $\overline{Q}$ output from latch 134C is applied to output circuit 178 shown in FIG. 6K to inhibit the provision of output signals being provided to analog circuit 42, which causes the cardiac stimulation pulses provided by pulse generator 16.

When the $\overline{Q}$ output of latch 134C becomes logic "0", the output from NAND gate 120A becomes a logic "1". When the Q output of latch 134C becomes logic "1" and write latch 128A is reset by the next slow clock logic 154 pulse, the output of NAND gate 120B becomes logic "1". Thus the output of NAND gate 120C becomes logic "0", removing the reset condition from latches 120D and 120E and allowing the timeout counter to count two recharge logic 164 pulse signals. After the second recharge logic 164 signal is counted, the $\overline{Q}$ output of latch 120E becomes logic "0", which, when applied to NAND gate 126A causes a reset signal to be provided from reset logic 126. Among other things, the output from NAND gate 126A causes latch 134C to be reset which, in turn, removes the inhibition to output circuit 178 and causes the output of NAND gate 120C to become logic "1" thereby providing the reset signal to latches 120D and 120E.

However, if a second inhibit programming signal is provided by programmer 12 prior to the time latch 120E in timeout logic 120 is set by the second pulse width logic 186 pulse write latch 128A is set, thereby causing a logic "1" signal to be applied to NAND gate 120B, which in turn causes a logic "0" signal to be applied to NAND gate 120C. This results in a logic "1" signal at the output of NAND gate 120C which resets latches 120D and 120E so that a new two pulse period is initiated and the inhibition remains. Otherwise the inhibition would be ended automatically upon the setting of latch 120E. To facilitate the continual application of inhibit programming signals, there is provided on programmer 12, function key 26 which must be held depressed whenever the inhibit parameter is programmed. The holding of this function key will cause continuous transmission of the inhibit programming signals to pulse generator 16 thereby preventing the counter in timeout logic 120 from timing out and causing a reset signal to be applied. To remove the inhibited condition a new programming signal should be sent or function key 26 should be released, thereby allowing the counter in timeout logic 120 to time out.

The second situation in which the reset signal is removed from latches 120D and 120E occurs whenever pulse counter 118 contains a non-zero count. This normally occurs during the reception of the DATA programming signal, which lasts for a period much shorter than the timeout period of two recharge logic 164 pulses. However, it is possible that muscle artifact or some electrical noise may result in the detection by the RF demodulator of a programming pulse and the provision of a DATA signal pulse. If this occurs, pulse counter 118 is incremented to a non-zero count. This results in NOR gate 118G providing a logic "0" signal to NAND gate 120A and ultimately the output of NAND gate 120C becoming logic "0", so as to remove the reset from latches 120D and 120E. After two recharge logic 164 pulses, latch 120E is set, thereby causing a reset signal from gate 126C to reset pulse counter 118 to a count of zero.

Referring now to FIG. 6F, parameter decode logic 138 includes 11 NOR gates 138A, 138B, 138C, 138D, 138E, 138F, 138G, 138H, 138I, 138J, and 138K. Each of NOR gates 138A through 138K are coupled to one of the two outputs from each of the last four stages of temporary memory 132 and are used to decode the particular one of the eleven parameters that can be programmed for pulse generator 16. Normally, the outputs of each NOR gate 138A through 138K is logic "0". However, whenever all of the signals applied to one of the NOR gates 138A through 138K are logic "0", the output becomes logic "1", signifying that the parameter with which that one NOR gate is associated is being modified.

The "1" outputs from each of stages 132-9 through 132-12 are applied to NOR gate 138A which decodes the inhibits parameter whenever all "0" bits are stored in stages 132-9 through 132-12 of temporary memory 132. The "0" outputs from each of stages 132-9 through 132-12 are applied to NOR gate 138B which decodes the output parameter whenever all "1" bits are stored in each of stages 132-9 through 132-12. The "1" outputs from stages 132-9 and 132-10 and the "0" output from stages 132-11 and 132-12 are applied to NOR gate 138C which decodes the hysteresis parameter. The "0" outputs from stages 132-9, 132-10, 132-12 and the "1" output from stage 132-11 are applied to NOR gate 138D which decodes the sensitivity parameter. The "1" output from stages 132-9, 132-10, 132-11 and the "0" output from stage 132-12 are all applied to NOR gate 138E which decodes the refractory parameter. The "0" outputs from 132-9 and 132-11 and 132-12 and the "1" output from stage 132-10 are applied to NOR gate 138F which decodes the R-sync parameter. The "0" outputs from stages 132-9 and 132-12 and "1" output from stages 132-10 and 132-11 are applied to NOR gate 138G which decodes the rate parameter. The "1" output from stages 132-9 and 132-11 and the "0" outputs from stages 132-10 and 132-12 are applied NOR gate 138H which decodes the pulse width parameter. The "1" output from stage 132-9 and the "0" outputs from 132-10, 132-11 and 132-12 are applied to NOR gate 138I which decodes the high rate parameter. The "0" output from stage 132-9 and the "1" output from stages 132-10, 132-11 and 132-12 are applied to NOR gate 138J which decodes the automatic threshold parameter. Finally the "1" output from stages 132-9, 132-11, and 132-12 and the "0" output from stage 132-10 are applied to NOR gate 132K which decodes the demand parameter.

Parameter decode logic 138 also includes seventeen two input NAND gates, 138L, 138M, 138N, 138O, 138P, 138Q, 138R, 138S, 138T, 138U, 138V, 138W, 138X, 138Y, 138Z, 138AA and 138BB. One of the inputs of each of NAND gates 138L through 138S are coupled to the output of memory strobe gate 136A and one of the inputs of each of NAND gates 138T through 138BB is coupled to the Q output of test latch 130. It should be recalled that whenever a pulse appears at the output of memory strobe gate 136A, the programming signal applied to pulse generator 16 is manifesting a permanent programming change is to occur. On the other hand whenever test latch 130A is set, the programming signal applied to pulse generator 16 is manifesting a temporary program change. Hence, a signal will appear at the output of one of NAND gates 138L through 138S, only when a permanent programming change is to occur and a signal will appear at the output of one of NAND gates 138T through 138BB only whenever a temporary programming change is to occur except when that temporary change is the inhibit parameter, in which case the output from inhibit decoding gate 138A is provided directly to inhibit logic 134 as previously explained.

The output parameter signal from NOR gate 138B is provided to the other input of NAND gates 138M and 138Z; the hysteresis parameter signal from NOR gate 138C is provided to NAND gate 138S; the sensitivity parameter signal from NOR gate 138D is provided to NAND gates 138R and 138U; the refractory parameter signal from NOR gate 138E is provided to NAND gates 138Q and 138V; the R-sync parameter signal from NOR gate 138F is provided to NAND gates 138P and 138W; the rate parameter signal from NOR gate 138G is provided to NAND gates 138O and 138X; the pulse width parameter signal from NOR gate 138H is provided to NAND gates 138N and 138Y; the high rate parameter signal from NOR gate 138I is provided to NAND gate 138T; the auto threshold parameter signal from NOR gate 138J is provided to NAND gate 138AA and the demand parameter signal from NOR gate 138K is provided to NAND gates 138L and 138BB. In addition, the demand parameter signal from NOR gate 138K is applied through an inverter 138CC to become the $\overline{\text{DEMAND}}$ parameter signal.

Referring now to FIGS. 6E, 6G and 6H, permanent memory 140 is shown. For convenience permanent memory 140 has been broken into blocks indicating the particular function of that portion of that memory. In the case of the sensitivity memory and refractory memory, both of which are two stages and shown in FIG. 6E, a detailed showing of each of the elements is given.

The two stage hysteresis portion of memory 140, the one stage output portion of memory 140 and the one stage R-sync portion of memory 140, are shown in FIG. 6G in a block format with input and output lines to the block, it being understood that these memories portions are identical to those shown in FIG. 6E with the exception of hysteresis memory 140 does not include certain components as will be explained hereafter. In addition the six stages of the pulse width portion of memory 140 and the eight stages of the rate portion of memory 140 are shown in FIG. 6H in block format and each have identical component stages to that shown in FIG. 6E.

Reference is now made specifically to two stage refractory portion of memory 140 shown in FIG. 6E. For brevity only one stage will be described, it being understood that the second stage is identical in both construction and operation to the first stage except as stated otherwise with regard to each specific item. The first stage of refractory memory 140 includes a memory loop consisting of inverters 140A and 140B and transmission gate 140C. The output of inverter 140A is coupled as the input of inverter 140B and output of inverter 140B is coupled to the input of transmission gate 140C, the output of which is coupled back to the input of inverter 140A. Transmission gate 140C is normally enabled by a logic "1" signal being applied thereto from gate 138Q in parameter decode logic 138 which normally provides a logic "1" signal as long as a permanent refractory programming change is not programmed. In the event such a permanent refractory change is programmed the output from gate 138Q becomes logic "0". In such a case transmission gate 140C is closed by the logic "0" signal from gate 138Q, which signal is inverted by inverter 140E and applied to enabled transmission gate 140D. The output from stage 132-1 of temporary memory 132 is applied to the input of transmission gate 140D and for the one pulse time duration that transmission gate 140D is enabled, a new bit from stage 132-1 is applied to and stored in the first stage of the refractory portion of memory 140.

The output from the first stage of the refractory portion of memory 140 is taken from the output of inverter 140A and applied through a second inverter 140H and normally enabled transmission gate 140G to an output from that stage. In the case of the refractory portion of memory 140, the output is the Refractory 1 signal which is applied to refractory logic 168 in FIG. 6N. In the case of the remainder of the memory portion, the output is applied to different portions of the circuit shown in the remainder of FIG. 6.

Transmission gate 140G is enabled by a logic "1" signal applied to the enable input thereof from the output of NAND gate 138V in parameter decode logic 138, which provides a logic "1" signal unless a temporary sensitivity programming change is to occur, in which case the output from gate 138V is logic "0" for as long as the temporary programming change is present.

In the event that a temporary programming situation is to occur the logic "0" signal from gate 138V disables transmission gate 140G and after being inverted by inverter 140I enables transmission gate 140F. The output from stage 132-1 from temporary memory also is applied to the input of transmission gate 140F, which, when enabled, provides a signal to the output stage of the refractory portion of memory 140.

The second stage of the refractory portion of memory 140 is identical to the first stage except that the input to the transmission gate corresponding to gates 140D and 140F is applied from the second stage 132-2 of temporary memory 132 and the output signal is the Refractory 2 signal. The output of inverter 140I is also applied as an output of the refractory portion of memory 140 and is the Temporary Refractory signal applied to demand logic 190.

The sensitivity portion of memory 140 is also shown in FIG. 6E and is identical to the refractory portion except that the parameter signals provided thereto from parameter decode 138 are provided from gates 138R for the permanent parameter change and from gate 138U for the temporary parameter change. In addition, the sensitivity portion of memory 140 includes an additional transmission gate 140J having its data input connected to the first stage at the junction of the transmission gates corresponding to gates 140F and 140G and its enable input connected to the output of the second stage of the sensitivity portion of memory 140. The output of transmission gate 140J is to output of the sensitivity portion of memory 140. The purpose of transmission gate 140J is to cause the output from the first stage to float when there is a logic "1" output from the second stage.

Referring now to FIG. 6G, the two stages of the hysteresis portion of memory 140 are identical to the refractory portion except that there are no corresponding elements to transmission gates 140F and 140G or inverters 140H and 140I. The reason for this is that the hysteresis portion of memory 140 is not programmable in the temporary mode; hence, there need not be any temporary programming components such as transmission gates 140F and 140G and inverter 140H or inverter 140I. Further, there is no input from a temporary parameter gate such as gate 138U, nor is there an output corresponding to the Temporary Refractory output.

The output portion and the R-sync portion of memory 140 are each one stage and substantially identical to the one stage described for the refractory memory portion 140 except that there is no signal provided from the output portion which corresponds to the Temporary Refractory signal. The inputs to the output portion and the R-sync portion of memory 140 are from stage 132-1 of temporary memory 132 and each is responsive to both a permanent and a temporary parameter signal from parameter decode logic 138.

Referring now to FIG. 6H and specifically to the pulse width portion and the rate portion of memory 140, the pulse width portion of memory 140 includes six stages, each of which is identical to the one stage described with respect to the refractory portion of memory 140 in FIG. 6E. The inputs to each of the six stages come respectively from the first through sixth stages 132-1 through 132-6 of temporary memory 132 and the permanent parameter signal is provided from gate 138N of parameter decode logic 138N.

The temporary parameter selection signal for the pulse width portion of memory 140 is provided from the output of inverter 140K, which inverts the output of a two input NAND gate 140L. The two inputs to NAND gate 140L are provided from the outputs of NAND gates 138Y and 138AA which respectively provide a signal in response to a temporary pulse width parameter program signal and a signal in response to an auto threshold parameter signal. It should be noted that there is no signal provided from the pulse width portion of memory 140 corresponding to the Temporary Refractory signal provided from the refractory portion of memory 140.

The rate portion of memory 140 consists of eight stages, each identical to the described first stage of refractory memory 140 and each of which is responsive to a respective one of the first eight stages 132-1 through 132-8 of temporary memory 132. The permanent parameter decode line is coupled to the output of NAND gate 138O in parameter decode logic 138, and the temporary parameter signal is applied from the output of an inverter 140M, which inverts the output applied from two input NAND gate 140N. The two inputs applied to NAND gate 140D are provided from the output of NAND gates 138T and 138X in parameter decode logic 138, which respectively provides a signal in response to the high rate parameter being programmed, and the rate being programmed in the temporary mode. Further, there is no signal provided from the rate portion of memory 140 corresponding to the Temporary Refractory signal provided from refractory portion of memory 140.

Referring again to FIG. 6G, threshold check logic 160 will be described. Threshold check logic 160 includes an inverter 160A, having the autothreshold parameter signal applied thereto from NAND gate 138AA in parameter decode logic 138 and providing a normally logic "0" output signal to one input of two input NAND gate 160B. The other input of NAND gate 160B is coupled to the normally logic "0" write latch 128 signal from FIG. 6A. The normally logic "1" output signal of NAND gate 160B is coupled to one input of a second NAND gate 160C, the other input of which is coupled to the Q output of the reed switch latch 159A signal provided from reed switch logic 159 in FIG. 6M. The reed switch latch 159A signal is logic "1" whenever reed switch 46 is closed. The output of NAND gate 160C is coupled to the reset input of a latch 160D, causing the $\overline{Q}$ output thereof to become logic "1". The $\overline{Q}$ output from latch 160D and logic "1" reed switch latch 159A signal are coupled to the two inputs of NAND gate 160E, the output of which is coupled to the reset inputs of latches 160E and 160G. Latch 160F has the Q signal from latch 164A in recharge logic 164 coupled to the clock input thereof and its own $\overline{Q}$ signal coupled to the data input thereof. The $\overline{Q}$ signal from latch 160F is also coupled to the clock input of latch 160G, which has its own $\overline{Q}$ signal coupled to its data input. The $\overline{Q}$ signal from latch 160G is coupled to the clock input of latch 160D. In addition, the set input to latch 160D is coupled to the Q output of the access code check logic latch 114D in FIG. 6A.

The Q outputs from latches 160F and 160G and the $\overline{Q}$ output from latch 186D in pulse width logic 186 are coupled to the three inputs of NAND gate 160H, the output of which is coupled to fast counter 152 to cause one pulse to be provided having a pulse width of 75% of the programmed pulse width. Finally, the $\overline{Q}$ outputs of latches 160F and 160G are coupled to the two inputs of NAND gate 160I, the output of which is coupled to rate decode logic 172 to cause three pulses to be provided at a rate of 100 pulses per minute.

In operation, threshold check logic 160 operates in only two situations, namely, first the closure of reed switch 46 and second, in response to the programming of the autothreshold function. Prior to the time reed switch 46 and when the reed switch logic latch 159A signal is logic "0", the output from both NAND gates 160C and 160E is logic "1" and this maintains latches 160D, 160F and 160G reset. When reed switch 46 is closed and the reed switch logic latch signal becomes logic "1", the outputs from both NAND gates 160C and 160E become logic "0", thereby removing the reset signal from latches 160D, 160F and 160G. Upon the occurrence of the rising edge of the next signal from the Q output of recharge logic latch 164A, latch 160A becomes set, thereby causing the output of NAND gate 160I to become logic "0", and enable pulses to be provided at the greater of 100 pulses per second, or the programmed rate. After two further recharge logic latch 164A pulses, both latches 160F and 160G are set, thereby enabling NAND gate 160H to provide a logic "0" pulse during the next pulse width logic signal applied thereto from the Q output of pulse width logic latch 186D. This signal increases the rate at which fast counter 152 counts so as to allow for the 75% pulse width pulse. The next recharge logic latch 164A signal causes latches 160F and 160G to become reset and latch 160D to become set. The then logic "0" $\overline{Q}$ signal from latch 160D causes a logic "1" signal at the output of NAND gate 160E, which maintains latches 160F and 160G in a reset condition with latches 160F and 160G reset, NAND gate 160I provides a logic "1" signal, and pulses at the programmed rate are provided. This situation continues as long as latch 160D remains set.

Latch 160D can only be reset if either reed switch 46 is opened or if the autothreshold function is programmed. When the autothreshold function is programmed, the write latch 128A signal becomes logic "1" and the autothreshold parameter signal from NAND gate 138AA becomes logic "0" at the same time. With the autothreshold parameter signal being inverted by inverter 160A, the output NAND gate 160B becomes logic "0" and the output of NAND gate 160C becomes logic "1" and resets latch 160D, causing a logic "0" at the output of NAND gate 160E. Thereafter threshold check logic 160 operates as described in the preceding paragraph. If for some reason, a new programming signal is received prior to the completion of the threshold check function, the access code check signal from latch 114D sets latch 160E, thereby terminating the threshold check.

Referring now to FIG. 6I, fast counter 152 is shown and consists of nine latches, 152A, 152B, 152C, 152D, 152E, 152F, 152G, 152H and 152I. In addition, fast counter 152 includes three two input NOR gates, 152J, 152K and 152L. The clock inputs to latches 152A and 152B are coupled to the clock signal at the output of clock logic 158. The clock input to the remaining latches 152C through 152I is coupled to the $\overline{Q}$ output from the preceding stage, 152B through 152H respectively. The data inputs of each of stages 152C through 152I are coupled to the $\overline{Q}$ output of that stage. The data input to latch 152A is coupled from the output of NOR gate 152K and the data input to latch 152B is coupled from the Q output of latch 152A. The reset inputs of each of the latches 152A through 152I are coupled together and to the slow clock logic 154 signal.

NOR gate 152J has one input coupled to the $\overline{Q}$ output of latch 152A and a second input coupled from the output of gate 160H in threshold check logic 160. The output of NOR gate 152J is coupled to one input of NOR gate 152K, the other input of which is the Q output from latch 152B. NOR gate 152L has one input coupled to the $\overline{Q}$ output from latch 152C and the second input coupled to the output of inverter 159B in reed switch logic 159. The output of NOR gate 152L is coupled to the clock inputs of latches 108B and 108C in data decode logic 108.

In operation, fast counter 152 is a normal divide by 256 divider circuit that provides a single pulse at the $\overline{Q}$ output of latch 152I for every 256 clock pulses applied to the clock input of latch 152A, as long as the output signal from NAND gate 160H in threshold check logic 160 is logic "1". In other words, latches 152A and 152B, and NOR gates 152J and 152K operate as a divided by four counting system. However, when the output from NAND gate 160H becomes logic "0", latches 152A, 152B in conjunction with NOR gates 152J and 152K operate as a divided by three network. At this time, fast counter 152 operates as a divided by 192 counter, rather than a divided by 256 counter. The output of fast counter 152 is the $\overline{Q}$ output from latch 152I, which becomes logic "0" after the divisor number of pulses are applied to the clock input of latch 152A.

Figure 6J:
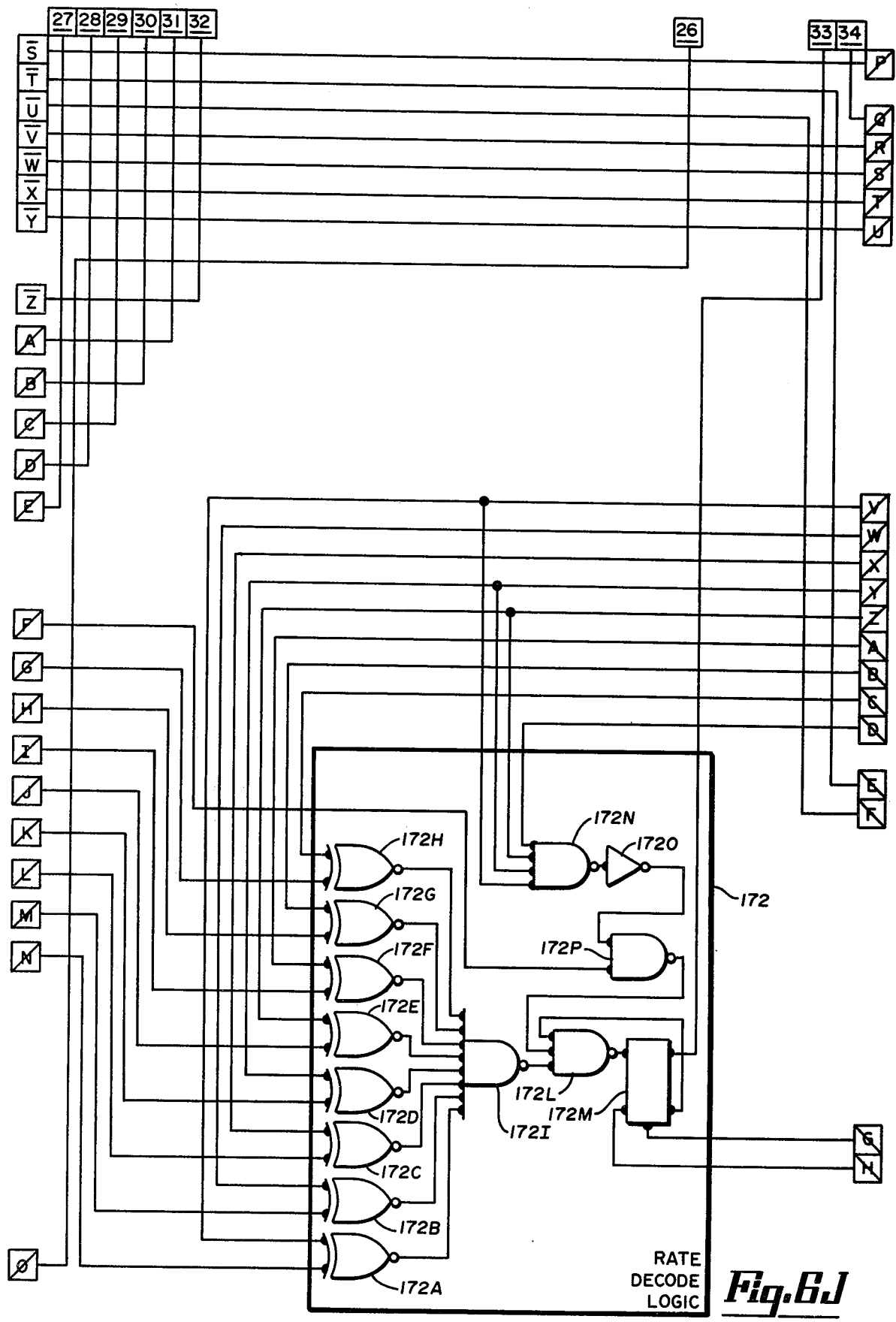
Figure 6K:
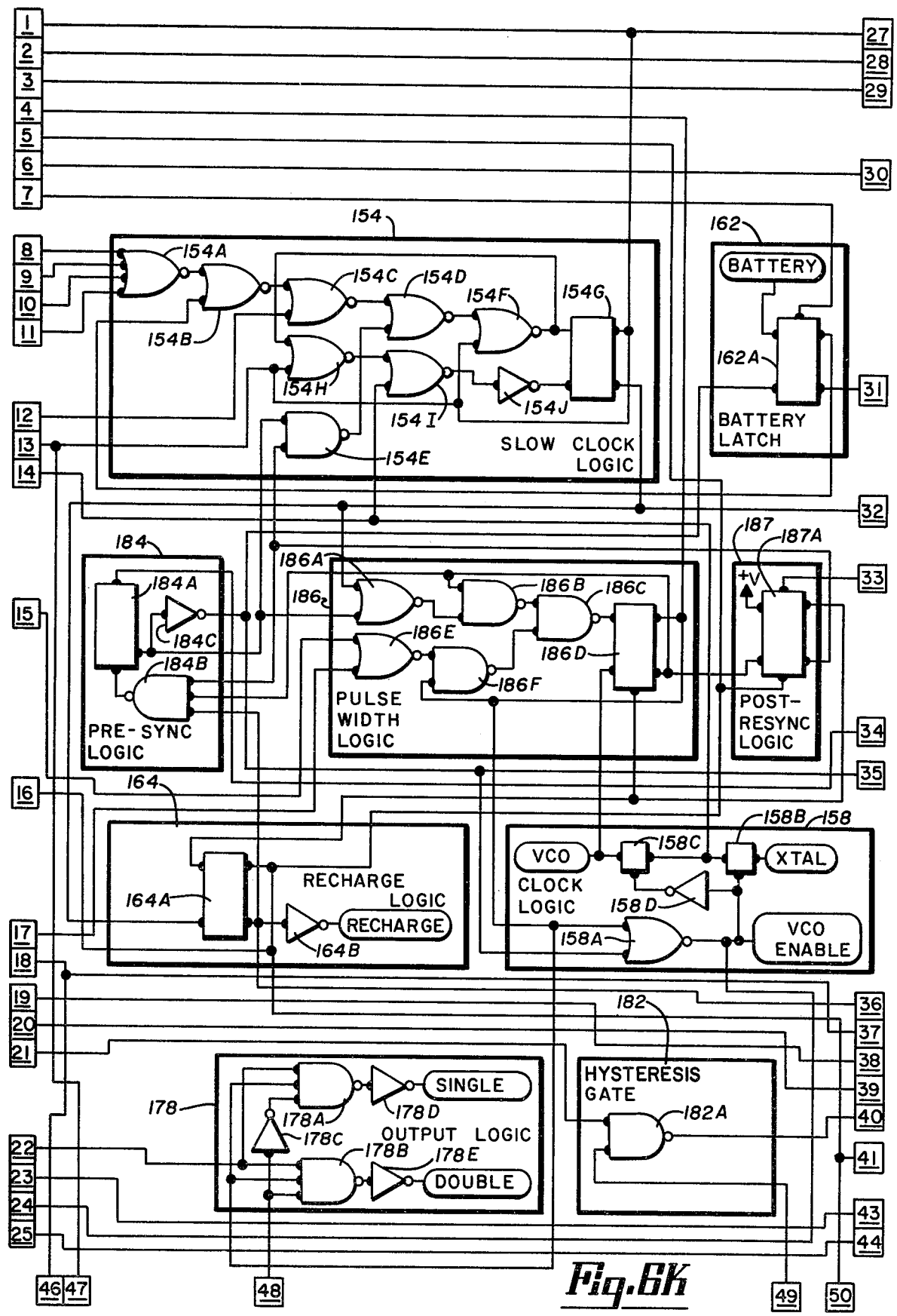

Referring now to slow clock logic 154 in FIG. 6K the $\overline{Q}$ outputs from latches 152B, 152C, 152D and 152E are applied as the four inputs to NOR gate 154A. The output of NOR gate 154A is coupled as one input to NOR gate 154B, with the other input thereof being coupled to the Q output of battery latch 162A. The output from NOR gate 154B is applied as one input to NOR gate 154C and the $\overline{Q}$ output from latch 154I is applied as the second input to NOR gate 154C.

As long as battery latch 162A remains set indicating that battery 44 is providing a voltage above a certain level, it is desirable that slow clock logic 154 provide a pulse each time latch 152I in fast counter 152 becomes set. This normally will occur at a rate of approximately 127 hz except that when NAND gate 160H in threshold check logic 160 is providing a logic "0", the slow clock signal will be at a rate of approximately 113 hz. However, when battery latch 162A becomes reset as a result of the voltage provided by battery 44 falling below a given value, it is desirable to decrease the slow clock signal rate by approximately 10%. Thus, if Q output from battery latch 162A is logic "1", as is the case with normal voltage, the output of NOR gate 154B will always be logic "0" and NOR gate 154C will provide a logic "1" output each time latch 152I is set and the Q output thereof becomes logic "0". However, if the battery voltage drops below a desired level, battery latch 162A will no longer be set and a logic "0" signal will be applied to NOR gate 154B from battery latch 162A. In this instance, the output of NOR gate 154B will be a logic "1" until the output of NOR gate 154A becomes logic "0", which occurs when latches 152B, 152C, 152D and 152E are all set. At this time, if latch 154I is set the output of NOR gate 154A becomes logic "1", causing the output of NOR gate of 154B to become logic "0" and enabling a logic "1" output signal to be provided at the output of NOR gate 154C. By selecting the $\overline{Q}$ outputs of latches 152B, 152C, 152D and 152E as the inputs to enable NOR gate 154A, the chain of pulses provided at the output of NOR gate 154C will be at a rate approximately 10% slower than are the pulses provided when battery latch 162A is set.

The output from NOR gate 154C is applied to one input of NOR gate 154D, the other input of which is coupled to the normally logic "0" signal from the output of NAND gate 154E. The output from NOR gate 154D is applied as one input to NOR gate 154F, the output of which is applied to the data input of latch 154G. The other input to NOR gate 154F is coupled to the Q output of latch 154G.

Slow clock logic 154 also includes NOR gates 154H and 154I and inverter 154J coupled in the clock circuit to latch 154G. The two inputs to NOR gate 154H are from the output of NOR gate 154F and the Q output of latch 154G. The two inputs to NOR gate 154I are from the output of NOR gate 154H and the clock signal from clock logic 158 and the output from NOR gate 154I is applied through inverter to the clock input of latch 154G. The Q output from latch 154G is applied to the reset input of each of the latches 152A through 152I in fast counter 152 to reset them so that the count of fast counter 152 is zero after each slow clock pulse is provided. The reason that the rate of slow clock logic 154 pulses is 127 hz is that two additional clock logic 158 pulse period times are required, one to cause the resetting of fast counter 152 and one to allow for the setting of latch 154G. Thus the rate of slow clock logic 154 pulses is 32,768 hz divided by (256+2) or 127 hz.

The two inputs to NAND gate 154E are provided from the $\overline{Q}$ output of pre-resync latch 184A and the $\overline{Q}$ output of post-resync logic latch 187A. As will be explained in detail hereafter, these two latches are used to resync the system timing when the VCO is enabled and later disabled during the pulse width time measurement. The timing resync is accomplished by resetting fast counter 152 both before and after the pulse width logic 186 pulse signal is provided, or in other words, whenever either pre-resync latch 184A or post-resync latch 187A are set. This is accomplished by the output of NAND gate 154E becoming a logic "0", thereby causing the output from NAND gate 154D to become logic "1" whenever either the pre-resync latch 184A or the post-resync latch 187A are set. Thus, the output from NOR gate 154D becomes logic "0" and allows latch 154G to then be set. Thus, two additional slow clock logic 154 pulses are provided to resync the timing when VCO pulses are applied.

Figure 6L:
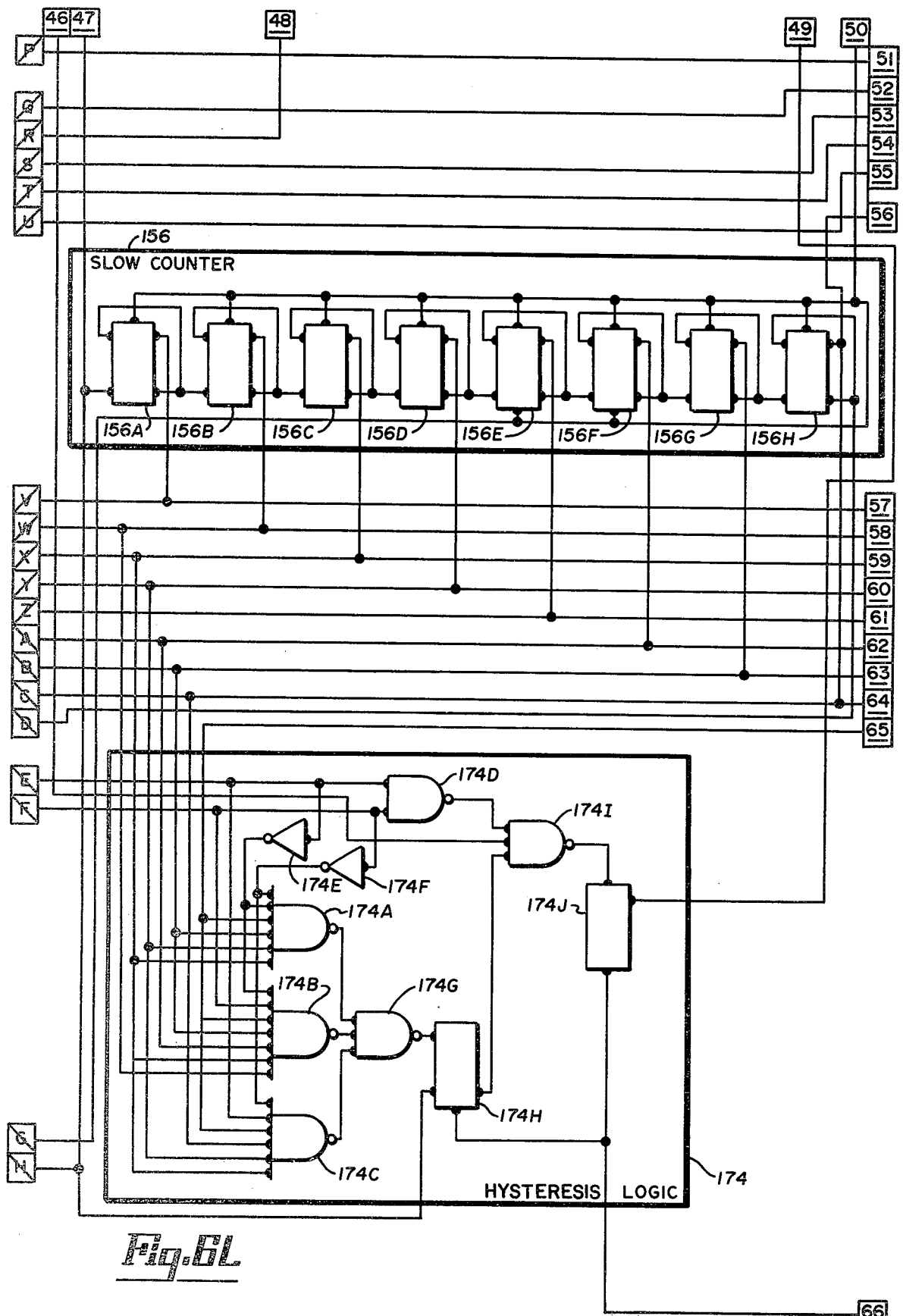

Referring now to FIG. 6L, slow counter 156 includes eight latches, 156A, 156B, 156C, 156D, 156E, 156F, 156G and 156H. The slow clock logic signal from latch 154G in FIG. 6K is applied to the clock input of latch 156A. The $\overline{Q}$ output from each of latches 156A through 156G is applied to the clock input of the next succeeding latches 156B through 156H, respectively, and the data input of each latch 156A through 156H is coupled to the $\overline{Q}$ output of that latch. The set inputs of latches 156A, 156B, 156C, 156D, 156G and 156H, and the reset inputs of latches 156E and 156F are coupled together and to the Q output from latch 164A in recharge logic 164. Thus, slow counter 156 is reset to a count of 208 each time the signal is provided to the set and reset inputs thereof from recharge logic 164. It should be noted that at a count of 208, it requires just under 400 msec for slow counter 156 to count the 127 hz slow clock logic 154 signal until slow counter 156 achieves a full count and overflows back to a zero count. As previously noted, this 400 msec time period is utilized for two purposes: (1) as a 400 msec refractory time, and (2) as a time during which no pulse width logic 186 pulses can be provided from the digital circuitry shown in FIGS. 6A through 6N, or in other words, as a rate limit time.

Referring now to FIG. J, the Q outputs from each of the latches 156A through 156H and slow counter 156 are applied respectively to one input of each of the EXCLUSIVE NOR gates 172A, 172B, 172C, 172D, 172E, 172F, 172G and 172H, respectively, in rate control logic 172. The other input to each of the EXCLUSIVE NOR gates 172A through 172H is applied from one of the stages of the rate memory portion of memory 140. The output of each of EXCLUSIVE NOR gates 172A through 172H is applied to an input of eight input NAND gate 172I, the output of which is applied to one input to three input NAND gate 172L. The other two inputs to NAND gate 172L are normally logic "1". The output from NAND gate 172L is applied to the data input of latch 172M and the slow clock logic 154 signal provided from the output of latch 154G is applied to the clock input of latch 172M. The Q output from latch 164D in recharge logic 164, which is provided to the set and reset inputs of the latches in slow counter 156, is also provided to the reset input to latch 172M. The Q output from latch 172M is provided as a second input to NAND gate 172L.

The Q output from each of latches 156A, 156D, 156E, and the $\overline{Q}$ output from latch 156H in slow counter 156 are all applied as inputs to NAND gate 172N. The output of NAND gate 172N is applied through inverter 172O to one input of NAND gate 172P. The other input to NAND gate 172P is provided from the output of NAND gate 160I in threshold check logic 160, and is normally a logic "0" signal, except during the period of time the threshold check function is occurring. The normal logic "1" output from NAND gate 172P is provided as the third input to NAND gate 172L.

Rate control logic 172 operates as follows. As the slow counter 156 count is incremented with each slow clock logic 154 pulse, the count thereof is compared with the code programmed into the rate portion of memory 140 by EXCLUSIVE NOR gates 172A through 172H. When the comparison is found, the output of each of the EXCLUSIVE NOR gates 172A through 172H is logic "1", causing the output of NAND gate 172I to become logic "0". When the comparison causes the output of NAND gate 172L to become logic "1" and on the next slow clock logic 154 pulse signal, latch 172M is set causing the $\overline{Q}$ output to become logic "0", and the Q output to become logic "1". The logic "0" $\overline{Q}$ output maintains the output of NAND gate 172L at a logic "1" state so that with each succeeding slow clock logic 154 pulse, latch 172N is maintained in a set condition.

In the event that a threshold check series of pulses is to be provided as a result of either the closure of reed switch 46 or the provision of the auto threshold parameter signal from NAND gate 138AA in parameter decode logic 138, the pulse width logic 186 pulse immediately following either the closure of reed switch 46 or the provision of the auto threshold parameter signal will occur at a normal rate and will set latch 160F. The next pulse width logic 186 pulse will cause latch 160G to be set. This in turn causes the output of NAND gate 160I to become logic "1" which enables NAND gate 172P to pass the signals from NAND gate 172N as inverted by inverter 172O. It should be noted that the output from NAND gate 172N will become logic "1" approximately 600 msec after slow counter 156 is reset, which corresponds to a rate of 100 bpm. The output from NAND gate 172P is then provided to NAND gate 172L to cause latch 172M to be set on the immediately following slow clock logic 154 pulse. This continues as long as NAND gate 160I provides the logic "1" signal, which is for a period during which two additional pulses at the 100 bpm rate are provided through gate 172P and 172L.

The Q output from latch 172M in rate control logic 172 is applied to one input of hysteresis gate 182A, shown in FIG. 6K. The other input of hysteresis gate 182A is normally a logic "1" signal provided from hysteresis logic 174, as shown in FIG. 6L. However, both signals apply to hysteresis gate 182A are logic "1", a logic "0" appears at the output thereof and is provided to one input of NAND gate 180A in digital rate limit logic 180, shown in FIG. 6M.

Referring now to FIG. 6L, hysteresis logic 174 may be programmed to have any one of three different lower hysteresis rates of 40, 50 or 60 bpm, or to be disabled. The particular programmed lower hysteresis rate or the disabled condition is controlled by the two outputs from the hysteresis portion of memory 140, shown in FIG. 6G. The three hysteresis rates are controlled by NAND gates 174A, 174B and 174C. The hysteresis disabled condition is controlled by NAND gate 174D. The upper output from the hysteresis portion of memory 140 is applied as one input to NAND gates 174C and 174D and the lower output from the hysteresis portion of memory 140 is provided to NAND gates 174B and 174D. In addition, the upper output from the hysteresis portion of memory 140 is applied through inverter 174E to inputs of NAND gates 174A and 174B, and the lower output from the hysteresis portion of memory 140 is applied through inverter 174F to NAND gates 174A and 174C. In addition, the 400 msec signal from the Q output from latch 166C in overflow logic 166 is applied to each of NAND gates 174A, 174B and 174C. Further, the Q outputs from latches 156C, 156D and 156G are spplied to the remaining inputs of NAND gate 174A, the Q outputs from latches 156B, 156C, 156F and 156G are applied to the remaining inputs of NAND gate 174B and the Q outputs from latches 156C, 156D and 156H are applied to the remaining inputs of NAND gate 174C.

The outputs from each of NAND gates 174A, 174B and 174C are applied as the three inputs to NAND gate 174G, the output of which is applied to the data input of latch 174H. The clock input to latch 174H is the slow clock logic 154 signal provided from the Q output of latch 154G in FIG. 6K.

Normally the output signals from NAND gates 174A, 174B and 174C are logic "1", thereby rendering the output from NAND gate 174F as a logic "0" signal. Hence, latch 174H is continually maintained in a reset condition by the slow clock logic 154 pulse signals applied to the clock input thereof. However, when one of the NAND gates 174A, 174B or 174C is selected by the outputs from the hysteresis portion of memory 140, a logic "0" signal will appear at the output thereof at the time slow counter 156 has counted to a count such that the inputs of that particular gate are all logic "1". At that time, a logic "0" signal will appear at the output of that selected one of the NAND gates 174A, 174B or 174C, which will cause the output of NAND gate 174G to become logic "1". This in turn will cause latch 174H to be set by the next slow clock signal.

The $\overline{Q}$ signal from latch 174H is applied as one input to NAND gate 174I and the output from NAND gate 174D is applied as a second input to NAND gate 174I. Further, the $\overline{Q}$ output from reed switch latch 159A in FIG. 6J is applied as a third input to NAND gate 174I. Each of the three signals applied to NAND gate 174I is normally a logic "1" and hence the output from NAND gate 174H is normally a logic "0" signal, which is applied to the set input of latch 174J. The reset input to latch 174J is coupled to the $\overline{Q}$ output from latch 170A, in reversion and sense reset logic 170. The Q output from latch 174J is coupled to the second input of hysteresis gate 182A in FIG. 6K and as long as latch 174J is set, hysteresis gate 182A is enabled to pass the signals from rate decode logic 172.

Latch 170A is normally maintained in a set condition and can only become reset in response to an acceptable SENSE signal from analog circuit 42. Thus, the signal applied to the reset input of latch 174J is normally logic "0" and becomes logic "1" in response to the sensing of a naturally occurring QRS signal by the sense amplifier. When such a natural QRS signal is sensed and latch 174J becomes reset, the Q output thereof becomes logic "0", thereby disabling hysteresis gate 182A. Hysteresis gate 182A will now remain disabled until such time as latch 174J is set by a logic "1" signal from NAND gate 174I, which occurs as a result of logic "0" signal from the output from one of NAND gates 174A, 174B or 174C, causing latch 174H to be set and provide a logic "0" signal to NAND gate 174I. Of course, if another natural QRS signal were sensed in the meantime, slow counter 156 would be reset and never reach a count sufficient for NAND gates 174A, 174B or 174C to provide a logic "0" signal.

On the other hand, if latch 174J does become set and hysteresis gate 182 is enabled to pass signals provided thereto from rate control logic 172, pulse width logic 186 will provide signals at the rate determined by the programmed code of pulse generator 16. As long as stimulating pulses are provided, latch 174J will remain set. It should be noted that latch 174J will remain set when both signals applied to NAND gate 174D are logic "1" or when reed switch 46 is closed and latch 159A in reed switch logic is set.

Assuming latch 174J is set and hysteresis gate 182A is enabled, the signals decoded in rate decode logic 172 will be applied through and inverted by NAND gate 182A, so that a logic "0" signal is applied as one input to NAND gate 180A in digital rate limit logic 180, each time slow counter 156 has counted to the value set into the rate portion of memory 140 and a comparison is made by EXCLUSIVE NOR gates 172A through 172H in rate decode logic 172.

Before describing digital rate limit logic 180, an understanding must be had of overflow logic 166 and gate 192 shown in FIG. 6M and of verify logic 188 in FIG. 6I. Referring first to gate logic 192 in FIG. 6M, there is included transmission gate 192A and NAND gate 192B having an output coupled to the control input of transmission gate 192A. The input to transmission gate is coupled to a ground or logic "0" signal and the output is coupled to the analog rate limit signal input pad. This pad is the input pad to which the rate limit signal from analog circuit 42 is provided. It should be recalled that the analog rate limit signal provided from analog circuit 42 is a logic "1" signal from the time a cardiac stimulating pulse is provided until a defined rate limit time thereafter, which may be on the order of 462 msec to give a rate limit frequency of 130 bpm. In certain circumstances, it is desirable to be able to cause pulses to be provided at a rate greater than the analog rate limit of 130 bpm. These circumstances include the provision of the verify pulse at a time of 100 msec following a normal stimulating or synchronized pulse to indicate that a permanently programmed change has been entered into memory 140. Another situation in which it is desirable to provide pulses at a rate exceeding the analog rate limit is during the programming of a high rate parameter in the temporary mode. Such a high rate programming may be used in situations where the pacemaker is utilized as an atrial pacemaker where it is desirable to drive the atrium at a high rate.

Gate 192 is provided to accomodate the two situations of verify pulse and high rate programming in which it is desired that the analog rate limit be overridden. In order to accomplish this, two normally logic "1" signals are applied as the inputs to NAND gate 192B, one from NAND gate 138T in parameter decode logic 138 and the other from verify pulse logic 188. The verify pulse logic 188 signal will become a logic "0" after the provision of the normal pulse of the verify pulse grouping and will remain at logic "0" until after the provision of the verify pulse. The normally logic "1" output from high rate parameter NAND gate 138T in parameter decode logic 138 becomes logic "0" whenever the high rate parameter has been decoded and will remain as such until such time that the programmed high rate situation is over. Thus, in normal circumstances the output of NAND gate 192B will be a logic "0" and transmission gate 192A will not be conductive. However, if either the verify pulse or the high rate parameter situations are occurring, the output of the NAND gate 192B will become logic "1" and transmission gate 192A will be closed to force the rate limit signal to logic "0" irrespective of the value of the signal applied from analog circuit 42.

Referring now to overflow logic 166 shown in FIG. 6M, there is included eight input NAND gate 166A, having an output coupled to a three input NAND gate 166B. NAND gate 166B has its output coupled to the data input of latch 166C. The clock input of latch 166C is coupled to the slow clock logic 154 signal provided from the Q output of latch 154G. The reset input of latch 166C is coupled to the Q output of latch 164A in recharge logic 164. Thus, latch 166C is reset after each cardiac stimulating pulse is provided or natural beat is sensed. The $\overline{Q}$ output from latch 166C is coupled as a second input to NAND gate 166B. The third input to NAND gate 166B is provided from the Q output of latch 156H in slow counter 156. The Q output from each of latches 156A, 156B and 156D through 156H of slow counter 156 are applied as seven of the eight inputs to NAND gate 166A. The eight input to NAND gate 166A is provided from the $\overline{Q}$ output of battery latch 162, which is normally a logic "0" signal. This maintains the output of NAND gate 166A at a normally logic "1" value regardless of the count contained by slow counter 156. However, when battery latch 162A becomes reset as a result of the battery voltage falling below a minimum value, the $\overline{Q}$ output thereof becomes logic "1" and the output of NAND gate 166A becomes a logic "0" when slow counter 156 contains a count of 151, that is, when all of the latches thereof, except latch 156C, are set.

NAND gate 166A is provided because when battery latch 162A becomes reset as a result of the battery voltage dropping, the rate of the slow clock signal is decreased by approximately 10%. Hence, it is necessary to compensate for this decrease in overflow logic 166A to maintain the setting of latch 166D at a constant time of approximately 400 msec after the provision of the stimulating pulse.

Overflow logic 166 operates as follows. First, assuming that battery 44 is providing an adequate voltage, gate 166A will provide a logic "1" output signal as a result of the logic "0" signal provided thereto from the $\overline{Q}$ output of battery latch 162A. At the time slow counter 156 is set to a count of 208 one slow clock cycle after the provision of the stimulating pulse, all of the signals applied to NAND gate 166B will be logic "1". Slow counter 156 increments its count after being set to the count of 208, and forty nine slow clock logic 154 pulses later, each of the latches will be reset and slow counter 156 will recycle to a zero count. At this point, the signal provided from the Q output of latch 156H will go from logic "1" to a logic "0". At the time the Q output from latch 156H becomes logic "0", the output from NAND gate 166B becomes logic "1" and on the next slow clock logic 154 pulse signal applied to the clock input of latch 166C, latch 166C becomes set as a result of the logic "1" now applied to the data input from NAND gate 166B. Thus, approximately 400 msec after the provision of the stimulating pulse, or the detection of a natural beat, overflow latch 166C is set.

If battery latch 162A had been reset, the output of NAND gate 166A would have become logic "0" at the time slow counter 156 was at a count of 251. The logic "0" from NAND gate 166A would be applied through NAND gate 166B to cause the output thereof to become logic "1" and the slow clock signal would then cause latch 166C to become set. In either case, once latch 160C is set, the Q output thereof becomes logic "0" and is applied back to one input of NAND gate 166B to maintain the output thereof at a logic "1". Hence, as subsequent slow clock pulses are applied to the clock input of latch 166C, it will continue to be held in the set condition.

Referring now to verify pulse logic 188 in FIG. 6I, there is included two latches, 188A and 188B, NAND gates 188C and 188E and NOR gate 188D. The memory strobe signal from memory strobe gate 136A shown in FIG. 6A and the $\overline{\text{DEMAND}}$ signal from inverter 138CC in parameter decode logic 138 are applied as the two inputs to NAND gate 138E, the output of which is applied to the clock input of latch 188A, the Q output of latch 188A is applied back to its data input and the Q output from latch 188A is applied to the data input of latch 188B. The Q output from latch 164A in recharge logic 164 is applied to the clock input of latch 188B. The Q output from latch 188B is applied to the reset input of latch 188A and also as one input to NAND gate 188C. The other input to NAND gate 188C is coupled to the signal from the Q output of latch 169A in blank logic 169, which signal is a normally logic "1" signal and becomes logic "0" upon the provision of the stimulating pulse and remains at logic "0" for approximately 100 msec thereafter.

The $\overline{\text{Q}}$ output from latch 188B is provided as one input to NOR gate 188D. The other inputs to NOR gate 188D are taken from the $\overline{\text{Q}}$ output of latches 152C and 152E in fast counter 152.

Verify pulse logic 188 operates in response to the provision of the memory strobe signal from memory strobe gate 136A in FIG. 6A except when the DEMAND parameter is permanently programmed. It should be recalled that a logic "1" pulse is provided from memory strobe gate 136A only in the event that a permanent programming signal has been accepted and is being writted in the permanent memory. The memory stobe signal is applied through NAND gate 188E, which is enabled by the normally logic "1" signal from the output of inverter 138CC in parameter decode logic 138, to the clock input of latch 188A to set latch 188A, causing the Q output of latch 188A to provide a logic "1" signal. The logic "1" signal from the Q output of latch 188A is applied to OR gate 176C in R-sync gate logic and to gate 190A in Demand logic to cause the next pulse to be delivered in an R-sync mode of operation. This is to insure that, in the event natural cardiac activity is occurring, the verify pulse will not be applied during the critical portion of the heartwave. The next occurring recharge logic 164 signal from the Q output of latch 164A thus causes latch 188B to become set. The $\overline{\text{Q}}$ output from latch 188B, which at this point is a logic "0" signal, enables NOR gate 188D to provide pulses each time latches 152C and 152E of fast counter 152 are in a set condition. It should be noted that since latch 188B is clocked by the Q output from latch 164A, in recharge logic 164, it is not set until after the provision of the stimulating pulse. When latch 188B is set, the logic "1" Q output thereof resets latch 188A and enables NAND gate 188C to provide a logic "0" pulse at its output for the blank time, or for approximately 100 msec after the provision of the normal stimulating pulse. The resetting of 188A also removes the R-sync mode of operation.

Referring now to digital rate limit logic 180, shown in FIG. 6M, there is included NAND gate 180A, inverter 180B, NAND gate 180C, NAND gate 180D, inverter 180E, and NAND gates 180F and 180G. The inputs to NAND gate 180A are provided from the output of hysteresis NAND gate 182A and from the output of NAND gate 188C in verify pulse logic 188. The output of NAND gate 180A is coupled to one input of NAND gate 180F.

The inputs to NAND gate 180C are provided from the Q output of latch 166C in overflow logic 166, and through inverter 180B from the rate limit input pad. The output from NAND gate 180C is provided as one input to NAND gate 180D. The other input to NAND gate 180D is provided from the output of inverter 180E, to which is provided the output of NAND gate 192B in gate circuit 192. The output of NAND gate 180D is provided to the other input of NAND gate 180F. The output from NAND gate 180F is provided as one of the two inputs to NAND gate 180G. The other input to NAND gate 180G is provided from the output of NAND gate 176A in R-Sync gate 176. The output of NAND gate 176A is normally a logic "1" signal and becomes a logic "0" signal in response to the sensing of a natural heartbeat signal after the refractory time, if pulse generator is programmed to operate in the R-Sync mode.

Under normal conditions, just after a stimulating pulse is provided by pulse generator 16, the analog rate limit circuit in analog circuit 42 will cause a logic "1" signal to be provided to the rate limit pad for a time of approximately 462 msec and, in addition, latch 166C will be reset, and the Q output thereof will be logic "0". Thus, both of the signals applied to NAND gate 180C will be logic "0" and output from NAND gate 180C will be a logic "1". As time passes, the analog rate limit signal will become logic "0", and latch 166C will become set, causing the two input signals to NAND gate 180C to become logic "1". Hence, the output of NAND gate 180C will become a logic "0" and cause the output of NAND gate 180D to become a logic "1". This enables NAND gate 180F to pass a logic "1" signal provided from NAND gate 180A to NAND gate 180G.

Under normal operation, the two inputs to NAND gate 180A will be logic "1" causing the output thereof to be a logic "0". At some point, the hysteresis gate output signal provided from NAND gate 182A to one input of NAND gate 180 becomes logic "0", indicating that a stimulating pulse is to be provided. Similarly, if the verify pulse is to be provided, the output from NAND gate 188C provided to the other input of NAND gate 180A becomes logic "0". When either of these signals become logic "0", the output of NAND gate 180A becomes logic "1", and both inputs to NAND gate 180F are logic "1", causing the output thereof to become logic "0". This, in turn, causes a logic "1" signal to be provided from the output of NAND gate 180H, which initiates the stimulating pulse in a manner to be explained hereafter.

In the event that a logic "0" pulse is provided to NAND gate 180A prior to the expiration of either of the digital or analog rate limit times, and assuming that the output from NAND gate 192B is logic "0", the output from NAND gate 180D will be logic "0". Hence, the logic "1" output pulse from NAND gate 180A will not be passed by NAND gate 180F. However, once the two rate limit times pass and the output from NAND gate 180D becomes logic "1", NAND gate 180F becomes enabled by the NAND gate 180D and any logic "1" signal applied thereto from NAND gate 180A will result in a logic "0" signal being provided from NAND gate 180F to NAND gate 180G, which in turn results in a logic "1" signal being provided from NAND gate 180G.

It should be recalled that the signal applied from hysteresis gate 182A to NAND gate 180A originates at the Q output of latch 172M in rate decode logic 172 and is continuously applied until the recharge logic 164 signal occurs after the provision of a stimulating pulse or the sensing of a natural heartbeat. Thus, even though NAND gate 180F may be disabled at the time a signal is applied from NAND gate 180A, the signal will continue to be applied until the rate limit times expire. In this manner, an upper rate is stabilized at the 130 bpm analog rate limit value, as opposed to many prior systems which merely ingnore any signal which occurs prior to the expiration of the rate limit period.

In those situations where it is desirable to provide pulses at a rate exceeding the upper rate limit value, such as in the situation with a high rate parameter being programmed, or where it is necessary to provide a verify pulse, the output from NAND gate 192B becomes logic "1", and inverter 180E causes a logic "0" signal to be applied to the other input of NAND gate 180D. This forces the output of NAND gate 180D to be logic "1" and NAND gate 180F is enabled so that the pulses provided to NAND gate 180A are applied through NAND gate 180F as in the normal manner of operation.

The output from NAND gate 180G in digital rate limiy logic 180 is applied to the set input of pre-resync latch 184A in FIG. 6K to initiate the provision of the cardiac stimulating pulse control signal from pulse width logic 186. Pre-resync latch 184A is utilized to initiate a change in the source of the clock pulses from clock logic 158 to those from the VCO rather than those from the external oscillator and to resynchronize the system timing to the new clock signal. It should be recalled that the VCO provides pulses at a rate of 40,000 hz as opposed to the external oscillator which provides pulses at a rate of 32,768 hz. Further, the rate of the VCO clock signal decreases in proportion to the decrease in voltage provided by battery 44. Thus, it is necessary to both restart and resync the pulse width control logic and the fast counter to the change in pulses caused by the setting of latch 184A.

Pre-resync latch 184A, as previously mentioned, has the output of NAND gate 180G applied to the set input thereof. Latch 184A is of a type in which a logic "1" signal applied to the reset input overrides the effects of a logic "1" signal applied to the set input. The reset input of pre-resync latch 184A is coupled to the output of NAND gate 184B which has three inputs respectively coupled to the Q output of latch 186D in pulse width logic 186, the Q output of post-resync latch 187A, and the Q output of recharge logic latch 164A. Thus, pre-resync latch 184A is reset upon the leading edge of the pulse width control signal provided from pulse width logic 186, and maintained reset until after the recharge signal.

The $\overline{Q}$ output from latch 184A is provided through inverter 184C to the clock input of battery latch 162A to cause a check of the battery voltage. The data input of battery latch 162 is coupled to the BATTERY signal which is logic "1" as long as the voltage from battery 44 is above the minimum level. The battery check accomplished by clocking battery latch 162A to the value of the BATTERY signal just prior to the provision of a stimulating pulse from pulse generator 16 in order to ignore any instantaneous drain on the battery due to the pulse. The set input to battery latch 162A is coupled to the Q output of test latch flip-flop 130A to allow the battery latch 162A to be set each time a temporary program change occurs.

The output from inverter 184C in pre-resync logic 184 is also coupled to one input of NOR gate 158A in clock logic 158. The other input of NOR gate 158A is coupled to the Q output from pulse width logic latch 186D. The output from NOR gate 158A is the VCO ENABLE signal, which is provided to analog circuit 42 to enable the VCO therein to provide pulses. Normally, this signal is a logic "1" as a result of the two normally logic "0" signals applied to NOR gate 158A. However, when pre-resync latch 184A is set and as long as pulse width logic latch 186D remains set, the VCO ENABLE signal remains a logic "0", thereby allowing for the provision of VCO pulses. The output from NOR gate 158A is also applied to the control input of transmission gate 158B, which has applied thereto the XTAL external oscillator clock signal, and also through inverter 158D to the control input of transmission gate 158C, which has applied thereto the VCO clock signal. The outputs of transmission gates 158B and 158C are coupled together and provide the clock logic 158 clock signal. As long as the output of NOR gate 158A is logic "1", transmission gate 158B is enabled and the XTAL signal is the clock logic 158 clock signal. However, if the output from NOR gate 158A becomes logic "0", transmission gate 158C is enabled and the clock logic 158 clock signal becomes the VCO signal.

The $\overline{Q}$ output signal from pre-resync latch 184A is applied to one input of NOR gate 186A in pulse width logic 186. Pulse width logic 186 also includes NAND gate 186B, NAND gate 186C, latch 186D, NOR gate 186E and NAND gate 186F. Each of the gates 186A, 186B, 186C, 186E and 186F have two inputs and an output. The second input to NOR gate 186A is provided from the $\overline{Q}$ output of latch 154C in slow clock logic 154. The output of NOR gate 186A is provided as one input to NAND gate 186B, the other input of which is coupled to the $\overline{Q}$ output of latch 186D. The output of NAND gate 186B is provided as one input to NAND gate 186C. NOR gate 186E has applied thereto the output from NOR gate 188D in verify pulse logic 188 and the output from inverter 157J in pulse width decode logic 157. The output of NOR gate 186E is applied to one input of NAND gate 186F and the other input to NAND gate 186F is provided from the Q output of latch 186D. The output of NAND gate 186F is provided as the other input to NAND gate 186C and the output of NAND gate 186C is coupled to the data input of latch 186D. The clock input to latch 186D is coupled to the VCO clock signal provided from analog circuit 42.

Pulse width decode logic 157 includes EXCLUSIVE NOR gates 157A, 157B, 157C, 157D, 157E, 157F, and 157G, each having two inputs and an output. The outputs of each of EXCLUSIVE OR gates 157A through 157G are each coupled to NOR gate 157H, the output of which is coupled to one input of NAND gate 157I. The other input to NAND gate 157I is coupled to the Q output of latch 188B in verify pulse circuit 188. The output of NAND gate 157I is coupled through inverter 157J to NOR gate 186E in pulse width logic 186.

One input of each of EXCLUSIVE NOR gates 157B through 157G is coupled to a corresponding one of the six stages of the pulse width portion of memory 140. The Q output of latch 152G of fast counter 152 is coupled to the other input to EXCLUSIVE NOR gate 157G; the Q output of latch 152F is coupled to the other input of EXCLUSIVE NOR gate 157F; and the $\overline{Q}$ output of latch 152E is coupled to the other input of EXCLUSIVE NOR gate 157E. The other inputs of EXCLUSIVE NOR gates 157B, 157C and 157D are respectively coupled to the output of OR gates 157M, 157N and 157O and both inputs to EXCLUSIVE NOR gate 157A are coupled to respective OR gates 157K and 157L. One input to each of OR gates 157K through 157O is coupled to the VCO ENABLE signal from clock logic 158. The Q outputs from latches 152B, 152C and 152D are respectively coupled to the other inputs of OR gates 157M, 157N and 157O, and the $\overline{Q}$ outputs of latches 152A and 152B are coupled to the other inputs of OR gates 157K and 157L.

NOR gates 157K through 157O are each enabled by the VCO ENABLE signal becoming logic "0" to allow EXCLUSIVE OR gates 157B through 157G to compare the count of the second through seventh stages (latch 152B through 152G) of fast counter 152 with the code in the pulse width portion of memory 140. When a comparison occurs, and when the outputs of each of EXCLUSIVE OR gates 157A through 157G is logic "0", the output of NOR gate 157H becomes logic "1". As long as NAND gate 157I is not disabled by verify pulse logic latch 188B being set, the logic "1" signal from NOR gate 157H pass through NAND gate 157I and inverter 157J to NOR gate 186E in pulse width logic 186.

In operation, pulse width logic latch 186D is set in response to the setting of pre-resync latch 184A to define the leading edge of the stimulating pulse. After the programmed pulse width time has passed, latch 186D is reset and, hence, the output of latch 186D is a pulse which controls the time and duration of the cardiac stimulating pulse to be provided by pulse generator 16. When pre-resync latch 184A and slow clock logic latch 154G are both set, both inputs to NOR gate 186A will be logic "0" and a logic "1" will be applied at the output thereof. This logic "1" signal is applied to NAND gate 186B which, together with the logic "1" from the $\overline{Q}$ output of latch 186D, provides a logic "0" to NAND gate 186C, thereby causing the output thereof to become logic "1". Upon the occurrence of the next VCO signal applied to the clock input of latch 186D, latch 186D becomes set causing the Q output thereof to become logic "1" and the $\overline{Q}$ output to become logic "0".

The output from NOR gate 188D in verify pulse logic 188 and the output from inverter 157J in pulse width control logic 157 are applied as the two inputs to NOR gate 186E. Normally both of these signals are logic "0" and, hence, the output of NOR gate 186E is a logic "1". At the time latch 186D becomes set and the Q output therefrom becomes logic "1", both inputs to NAND gate 186F are logic "1" causing the output thereof to be a logic "0". This maintains the output from NAND gate 186C at a logic "1", so latch 186D continues to be set each time a VCO signal is applied thereto from clock logic 158.

After fast counter 152 has counted to a value equal to the value programmed in the pulse width portion of memory 140, and the output from each of the EXCLUSIVE NOR gates 157A through 157G in pulse width control logic 157 becomes logic "0", the output from inverter 157I becomes logic "1". This logic "1" is applied to NOR gate 186E and causes the output thereof to become a logic "0", which in turn, causes the output of NAND gate 186F to become a logic "1", and the output of NAND gate 186C, to become a logic "0". Hence, latch 186D will be reset upon the occurrence of the next VCO pulse applied thereto from clock logic 158. Thus, latch 186 is set upon the occurrence of pre-resync latch 184 being set and reset upon the passage of the proper pulse width time.

In the event that a verify pulse is to be provided, the output from NOR gate 188D becomes logic "1" after both latches 152C and 152E are reset. This causes the other input of NOR gate 186E to become logic "1" and the same chain of events occurs to terminate the verify pulse. It should be recalled that the verify pulse was initiated by NAND gate 188C applying a logic "0" signal to NAND gate 180A in digital rate limit logic 180.

The $\overline{Q}$ output from pulse width logic latch 186D is applied to the clock input of post-resync latch 187A and the data input of the latch 187A is coupled to the voltage source to always receive a logic "1" signal. The set input to post-resync latch 187A is coupled to the output of NOR gate 176B in R-sync gate 176 which provides a logic "1" pulse signal whenever a natural heartbeat is sensed if the pacemaker is programmed in the demand mode. The reset input to post-resync latch 187A is coupled to the Q output of recharge latch 164A.

The purpose of post-resync latch 187A is to resync the logic system to the change in clock signals from the VCO clock to the XTAL external oscillator clock in the event an artificial stimulating pulse is provided and to cause the setting of the recharge latch 164A in the event a natural heartbeat is detected or an artificial stimulating pulse is provided. Latch 187A is set in response to the trailing edge of the pulse width signal from latch 186D, that is, at the time latch 186D is reset, or in response to a logic "1" signal from NOR gate 176B whenever a natural heartbeat is sensed. The $\overline{Q}$ output from latch 187A is applied through NAND gate 154E to cause an extra slo clock logic 154 pulse from the output of latch 154G. This, in turn, causes fast counter 152 to be reset to the count of zero, at the conclusion of the stimulating pulse or after a natural beat is sensed. The Q output from latch 187A is also applied through NAND gate 184B to reset pre-resync latch 184A.

The Q output from post-resync latch 187A is applied to the data input of recharge latch 164 and the slow clock logic 154 signal is applied to the clock input of recharge logic 164A. Thus, recharge latch 164A is set by the slow clock logic 154 pulse caused by the setting of post-resync latch 187A and reset by the next slow clock logic 154 pulse approximately 7.8 msec thereafter.

The $\overline{Q}$ output from recharge latch 164A is applied through inverter 164B to become the RECHARGE signal applied to analog circuit 42, which allows the capacitor in the voltage doubler portion of analog circuit 42 to be recharged quickly. The Q output from recharge latch 164A is applied to reset post-resync latch 187A and to force set slow counter 156 to a count of 208, and to reset both rate decode latch 172M, and overflow latch 166C.

The output control pulse from the Q output of latch 186D in pulse width logic 186 is a logic "1" pulse signal having a duration equal to the programmed pulse width. This signal is applied to one input of each of NAND gates 178A and 178B in output logic 178. Output logic 178 also includes inverters 178C, 178D and 178E with inverter 178D being coupled between the output of NAND gate 178A and the SINGLE output pad and inverter 178E being coupled between the output of NAND gate 178B and the DOUBLE output pad. Whenever a logic "1" pulse signal is applied to the SINGLE output pad and from there to analog circuit 42, a stimulating pulse having a magnitude of battery 44 voltage is provided by pulse generator 16. Similarly, whenever a logic "1" pulse signal is provided to the DOUBLE output pad and from there to analog circuit 42, an artificial stimulating pulse is provided from pulse generator 16 having double battery 44 voltage.

Also coupled to NAND gate 178B is the signal provided by the output portion of memory 140. This same signal is provided through inverter 178C to a second input of NAND gate 178A. Connected in this manner, if the data bits stored in the output portion of memory 140 is a logic "1", NAND gate 178B is enabled and the pulse width logic 186 signal is provided to the DOUBLE output pad. On the other hand, if the data bits stored by the output portion of memory 140 is a logic "0", NAND gate 178A is enabled and the pulse width logic 186 signal is provided to the SINGLE output pad.

Whenever it is desired to inhibit the provision of output pulses, both NAND gates 178A and 178B are disabled by a logic "0" inhibit signal provided thereto from the $\overline{Q}$ output of latch 134C and inhibit logic 134, shown in FIG. 6C.

Referring now to FIG. 6N, blank logic 169, reversion and sense reset logic 170 and refractory logic 168 will now be described. The primary purpose of blank logic 169 is to provide to the BLANK output pad, a logic "0" pulse having a duration of 100 msec, measured from the leading edge of an artificial stimulating pulse or from the sensing of a natural heartbeat. The blank logic 169 pulse is provided from the BLANK output pad to analog circuit 42 to cause the sense amplifier therein to be disabled during this 100 msec time period, that is, to be incapable of sensing any cardiac activity.

Blank logic 169 includes five input NAND gates 169B and 169C, three input NAND gates 169D, latch 169A, two input NOR gate 169E and inverters 169F and 169G.

The inputs to NAND gates 169B are from the $\overline{Q}$ output of battery latch 162A and the Q outputs from each of latches 156D, 156E, 156G and 156H of slow counter 156. The inputs to NAND gate 169C are from the Q outputs from each of latches 156B, 156D, 156F, 156G and 156H of slow counter 156. The outputs from each of NAND gates 169B and 169C are coupled as two of the inputs to NAND gate 169B. The third input to NAND gate 169D is coupled to the $\overline{Q}$ output from latch 169A. The output of NAND gate 169D is coupled to the data input of latch 169A. The clock input of latch 169A is the output of slow clock logic 154. The reset input into latch 169A is coupled to the output of inverter 169F, which inverts the signal provided from NOR gate 169E. The two inputs to NOR gate 169E are provided respectively from the output of NOR gate 176B in R-sync gate 176 shown in FIG. 6M, and the output from inverter 184C from pre-resync logic 184 shown in FIG. 6K. The $\overline{Q}$ output from latch 169A is coupled through inverter 169G to the BLANK output path.

In operation, latch 169A is normally set so that the $\overline{Q}$ output is a logic "0" signal, which when applied back through NAND gate 169D maintains the signal applied to the data input of latch 169A at logic "1". Thus, each time a slow clock logic 154 signal is provided to the clock input of latch 169A, it is maintained in a set state. During this period of time, the signals applied to NOR gate 169E are normally both logic "0" and hence the output thereof is a logic "1", which when inverted by inverter 169F provides a logic "0" signal to the reset input of latch 169A. Whenever an artificial stimulating pulse is to be provided, pre-resync logic 184A is set, causing the output from inverter 184C to become logic "1". This, in turn, causes the output from NOR gate 169E to become logic "0" and the output of inverter 169F to become logic "1" and resets latch 169A. Furthermore, if a natural heartbeat is sensed, the output from NOR gate 176B is R-sync gate 176 becomes a logic "1", causing the output of NOR gate 169E to become logic "0" and the output of inverter 169F to become logic "1" and reset latch 169A. Whenever latch 169A is reset by a signal from the output of inverter 169F, the $\overline{Q}$ output thereof becomes logic "1". At this time, the outputs from both NAND gates 169B and 169C are also logic "1" and thus the output from NAND gate 169D becomes a logic "0". Subsequent slow clock logic 154 pulses maintain latch 169A in a reset condition.

Eventually, slow counter 156 will be incremented to a count such that one of NAND gates 169B or 169C has all logic "1" signals applied to the input thereof. The particular one of NAND gates 169B or 169C will depend upon whether battery latch 162A is set or reset. Whenever one of NAND gates 169B or 169C provides a logic "0" signal, the output of NAND gate 169D will become logic "1" and the next occurring slow clock logic 154 pulse will cause latch 169A to become set. With the $\overline{Q}$ output from latch 169A being applied through NAND gate 169B, this set condition will continue until such time as latch 169A is again reset by a logic "1" signal from inverter 169F. It should be noted that the inputs to NAND gates 169B and 169C from the selected stages of slow counter 156 are such that a logic "0" output will occur from these particular gates at 100 msec following a cardiac stimulating pulse or the detection of a natural heartbeat.

Refractory logic 168 is designed to allow a signal to be generated which causes reversion and sense reset logic 170 to ignore any sensed natural cardiac activity for a set refractory time. The refractory time may be selected by the code contained in the refractory portion of memory 140 to be either 220 msec, 325 msec, 400 msec or infinity. If infinity is selected as a refractory time, pulse generator 16 operates as an asynchronous pacemaker. This is the manner in which pulse generator 16 can be programmed to operate in the asynchronous mode.

Refractory logic 168 includes a pair of six input NAND gates 168A and 168B having their outputs coupled as the inputs to a NAND gate 168C. Refractory logic 168 also includes two input NAND gate 168D, three input NAND gates 168E and 168F, four input NAND gate 168G, a latch 168H and two inverters, 168I and 168J. NAND gate 168D is utilized to control the 220 msec refractory time. NAND gate 168E is utilized to control the 325 msec refractory time and NAND gate 168F is used to control the 400 msec refractory time. The refractory 1 signal provided from the upper stage of the refractory portion of the memory 140 shown in FIG. 6E is applied as one input to NAND gate 168F and through inverter 168I to NAND gates 168D and 168E. The refractory 2 signal from the lower stage of the refractory portion of memory 140 is applied as one input to NAND gate 168E and through inverter 168G to one input of NAND gates 168D and 168F. The output from NAND gate 168C is provided as the final input to NAND gate 168E and the overflow logic signal at the output of NAND gate 166B in overflow logic 166 is provided as a third input to NAND gate 168F. The outputs of each of NAND gates 168D, 168E and 168F are provided to inputs of NAND gate 168G, together with the $\overline{Q}$ output from latch 168H. The output of NAND gate 168G is provided to the data input of latch 168H and a slow clock logic 154 signal is provided to the clock input of latch 168H. The reset input to latch 168H is the recharge logic 164 signal from the Q output of latch 164A.

The inputs to NAND gate 168A are provided from the $\overline{Q}$ output of battery latch 162A and from the Q outputs of latches 156B, 156E, 156F, 156G and 156H of slow counter 156. The inputs to NAND gate 168B are provided from the Q outputs of latches 156B, 156C, 156E, 156F, 156G, and 156H of slow counter 156. Connected in this manner, the outputs of NAND gates 168A and 168B become logic "0" as a result of all logic "1" signals being applied thereto 325 msec after slow counter 156 is forced set to the count of 208 by the recharge signal. Latch 168B provides the signal so long as normal battery voltage is being provided and battery latch 168A is maintained in the set condition. On the other hand, battery latch 162A becomes reset 325 msec signals provided from the output of NAND gate 168A.

The particular one of NAND gates 168D, 168E, or 168F which can be enabled is determined by the code of the refractory 1 and refractory 2 signals provided from the refractory portion of memory 140. If the code of these signals, which manifests the code stored by the refractory portion of memory 140, is "0-0", NAND gate 168D is enabled, and always provides a logic "0" signal. If the code is "0-1", NAND gate 168E is enabled and provides a logic "0" whenever NAND gate 168C provides a logic "1" signal thereto as a result of the passage of 325 msec as determined by NAND gates 168A and 168B. If the refractory signal code is "1-0", the NAND gate 168F is enabled and provides a logic "0" signal whenever the 400 msec time period has passed, as determined by overflow logic 166. If the refractory code is "1-1", then none of the gates 168D, 168E or 168F will ever be enabled and they will all continue to provide logic "1" signals at their outputs. In this latter instance, NAND gate 168G will always provide a logic "0" signal at its output and latch 168H can never be set by one of the slow clock logic 154 pulses. This will prevent any response to the sensing of natural cardiac activity.

In operation, latch 168H in refractory logic 168 is reset by the rechage logic 164 signal from the Q output of latch 164A after each artificial stimulating pulse is provided or after each natural beat is detected. If NAND gate 168D is enabled by the refractory portion of memory 140, latch 168H will be immediately set, causing the Q output thereof to become logic "1". If one of NAND gates 168E or 168F is enabled by the refractory portion of memory 140, all of the signals provided to NAND gate 168G are logic "1", and the output thereof is logic "0". Latch 168H is thus maintained in a reset condition by slow clock logic 154 pulse until the selected one of NAND gates 168E or 168F provides a logic "0" signal to one of the inputs of NAND gate 168G after the selected period of time. At this point the output of NAND gate 168G becomes logic "1" and upon the next occurring slow clock logic 154 pulse, latch 168H becomes set, causing the Q output thereof to become logic "1" and the $\overline{Q}$ output thereof to become logic "0". With the $\overline{Q}$ output being applied back through NAND gate 168G, latch 168H is maintained in a set condition, until it is again reset by a recharge logic 164 signal.

Referring now to reversion and sense reset logic 170, the SENSE signal from analog circuit 42 is provided and if it occurs at a proper time, latch 170A is set to indicate that a natural heartbeat has been detected. Reversion and sense reset logic 170 includes a reversion counter consisting of latches 170B, 170C, 170D, 170E and 170F, each having its $\overline{Q}$ output coupled back to its data input and each having its clock input coupled to the $\overline{Q}$ output of the preceding stage. In the case of latch 170B, the clock input is coupled to the output of NOR gate 170G, which has as its inputs the outputs from NOR gate 170H and a slow clock logic 154 signal from the $\overline{Q}$ output of latch 154G. NOR gate 170H has applied to its four inputs the $\overline{Q}$ outputs from each of latches 170B, 170C, 170E and 170F. Lastly, the reset inputs to each of latches 170B through 170F are coupled to the output from NAND gate 170I, which provides a logic "1" signal each time natural cardiac activity is sensed or a recharge signal is provided from the $\overline{Q}$ output of latch 164A.

Connected in the manner described above, latches 170B through 170F and NOR gates 170G and 170H form a 212 msec resettable monostable multivibrator. Whenever latches 170B through 170F become reset as a result of a logic "1" signal from NAND gate 170I, the output of NOR gate 170H becomes logic "0" and enables NOR gate 170G to pass the slow clock logic 154 signals. These signals are counted by the counter formed by latches 170B through 170F until such time as latches 170B, 170C, 170E and 170F are all set and latch 170D is reset, which takes approximately 220 msec, from the time the counter was last reset. The additional 8 msec is caused by an extra SLO CLK interval being added as a result of the recharge signal resetting the counter. At this point, the output of NOR gate 170H becomes logic "1" as a result of each of its inputs being logic "0" and this, in turn, disables NOR gate 170G from passing any further slow clock logic signals.

Hence, the counter formed by latches 170B through 170F stops counting. However, if prior to the passage of the 220 msec time period, a logic "1" signal has been provided at the output of NAND gate 170I, latches 170B through 170F would have been reset and another 212 msec would be required before NOR gate 170H provided a logic "1" signal.

Reversion and sense reset logic 170 also includes six input NAND gate 170J, to which is applied the $\overline{Q}$ output of each of latches 170B through 170F and the slow clock logic 154 signal from the $\overline{Q}$ output of latch 154G. Connected in this manner, NAND gate 170J provides a logic "0" signal coincident with the slow clock logic 154 signal each time the counter formed by latches 170B through 170F is reset. The output from NAND gate 170J is applied as one input to NAND gate 170K, the other input of which is provided from the Q output of latch 169A in blank logic 169. The output of NAND gate 170K is provided to the reset input of latch 170L. The data input to latch 170L is connected to battery voltage or a logic "1" signal. The clock input to latch 170L is connected to the output of NOR gate 170M, one input of which has applied thereto the SENSE signal from analog circuit 42 and the other input of which has applied thereto the signal from the output of NOR gate 190A in demand logic 190. Normally, the output of NOR gate 190A is a logic "0" signal and maintains NOR gate 170M enabled.

The $\overline{Q}$ output from latch 170L is provided as one input to NAND gate 170I. The other input to NAND gate 170I is the recharge logic 164 signal provided from the Q output of latch 164A. Connected in this manner, NAND gate 170I provides a logic "1" signal at its output to reset the reversion counter whenever either latch 170L becomes set as a result of the provision of a sense signal or whenever a recharge signal is provided from recharge logic 164 as a result of the provision of a pulse which logic 186 signal or the sensing of a natural cardiac beat.

The Q output from latch 170L is applied to the clock input of latch 170A, and the data input to latch 170A is coupled to the output of NAND gate 170N, which has the output from NOR gate 170H applied to one input thereof and the output of refractory logic latch 168H applied to the other input thereof. The set input to latch 170A is coupled to the recharge logic 164 signal from the Q output of recharge latch 164A. Each time an artificial beat is provided or natural activity is sensed and the recharge signal is provided from recharge logic 164, latch 170A is forced set, causing the Q output thereof to become a logic "1" and the $\overline{Q}$ output thereof to become logic "0". The only manner in which latch 170A can become reset is by the data input signal from NAND gate 170N becoming logic "0" prior to the time that the SENSE signal is provided through NOR gate 170M to set latch 170L. In order for the data input of latch 170A to become logic "0", both inputs to NAND gate 170N must be logic "1". Thus, the reversion counter consisting of latches 170B through 170F must have counted past the 212 msec time period, and, in addition, latch refractory logic 168H must be set as a result of the passage of the selected refractory time period. If after both of these time periods have passed, the SENSE signal is provided from a sense amplifier in analog circuit 42, latch 170L becomes set, causing the Q output thereof to become logic "1". This, in turn, clocks the logic "0" signal from NAND gate 170N into latch 170A, causing the Q output thereof to become logic "0" and the $\overline{Q}$ output thereof to become logic "1". The $\overline{Q}$ output from latch 178 is provided to hysteresis logic 174 to reset latches 174H and 174J therein in the manner previously explained.

With respect to reversion and sense reset logic 170, it should be noted that if gate 168D in refractory logic 168 is selected by the code of the refractory portion of memory 140, latch 168H will always be set and only the 220 msec time from reversion counter 170D would control the refractory time. Thus, there would have been selected a 220 msec refractory time. It also should be noted that if an infinite refractory time is selected by the code of the refractory portion of memory 140, latch 168H can never be set and hence the output from NAND gate 170N can never become logic "0". In this situation, latch 170A can never be reset to indicate the sensing of natural cardiac activity. Hence, pulse generator 16 would operate in an asynchronous mode.

It should also be noted that in the event natural cardiac activity is sensed prior to the expiration of the 220 msec timeout period of the reversion counter formed by latches 170B through 170F the conversion counter will be reset and another 212 msec time period will be required. This feature becomes important in the event that there is a continuous interference signal being detected by the sense amplifier within analog circuit 42. If this continuous interference has a frequency greater than approximately five hz, the reversion counter formed by latches 170B through 170F will continually be reset and never be able to count to the 212 msec time period. Hence, NOR gate 170H will never provide a logic "1" signal to allow NAND gate 170N to be able to provide a logic "0" signal. Hence, pulse generator 16 will be operate into the asynchronous mode, or as is more commonly referred to, will be reverted to the asynchronous mode due to the presence of the continuous wave of external interference signal.

Referring now to R-sync gate 176 shown in FIG. 6M, there is included NAND gate 176A, NOR gate 176B and OR gate 176C, each having two inputs and an output. One of the inputs of each of NAND gate 176A and NOR gate 176B is coupled to the output of OR gate 176C, which has the R-sync portion of memory 140 and the Q output of latch 188A in verify pulse logic 188 coupled thereto. If the R-sync portion of memory 140 or the Q output of latch 188A provides a logic "1" signal, OR gate 176C provides a logic "1" signal to enable NAND gate 176A to cause pulse generator 16 to operate in the R-synchronous mode. If the R-sync portion of memory provides a logic "0" signal and latch 188A is not set, NOR gate 176B is enabled to allow pulse generator 16 to operate in the demand mode. The other input of NAND gate 176A is coupled to the $\overline{Q}$ output of latch 170A in reversion and sense reset logic 170 and the other input to NOR gate 176B is coupled to the Q output of latch 170A. If NAND gate 176A is enabled, the R-synchronous mode of operation is programmed and thus, each time a SENSE signal is provided and latch 170A is set, a logic "0" will be provided from NAND gate 176A to NAND gate 180G in digital rate limit circuit 180 to cause a cardiac stimulating pulse to be provided in the manner previously described. On the other hand, if NOR gate 176B is enabled by a logic "0" signal from the R-sync portion of memory 140, manifesting a demand mode of operation, each time latch 178A is set as a result of the sensing of natural cardiac activity, a logic "1" signal will be applied from NOR gate 170B to set post-resync logic latch 187A to cause the recharge signal to be provided to reset slow counter 156 and begin a timeout period for a new pulse. If latch 188A is set, the extra verify pulse and the pulse preceding it will occur in the R-sync mode to insure that the venerable portion of the heart cycle is not pulsed.

Referring now to demand logic 190, shown in FIG. 6I, there is included six input NOR gate 190A, two input NOR gate 190B, latch 190C and inverter 190D. The purpose of demand logic 190 is to control the mode of the pacemaker during the time reed switch 46 is closed. Normally, pulse generator 16 operate in the asynchronous mode whenever reed switch 46 is closed. However, in certain situations, especially while a physician is continually programming the pacemaker to perform certain diagnostic tests, it may be desired to operate pulse generator 16 in the demand mode. Additionally, it would be expected to be necessary to operate pulse generator 16 in a demand mode whenever certain parameters are being programmed, such as SENSITIVITY, R-SYNCHRONOUS and REFRACTORY in the temporary mode, since these parameters are dependent upon the proper operation of the sense amplifer.

Latch 190C has provided to its data input the output from stage 132-8 of temporary memory 132, or in other words, the least significant bit of the data portion of the programming word. The output from NAND gate 132L, manifesting the permanent DEMAND parameter, is provided through inverter 190D to the clock input of latch 190C and the Q output from reed switch latch 159A in reed switch logic 159 is provided to the set input of latch 190C, as well as to one input of NOR gate 190A. The Q output from latch 190C is also provided as one input to NOR gate 190A. The output from stage 132-8 of temporary memory 132 is also provided as one input to NOR gate 190B. The other input to NOR gate 190B is provided from the output from NAND gate 138BB in parameter decode logic 138, which is the temporary DEMAND parameter output. The output of NOR gate 190B is provided as a third input to NOR gate 190A. The other three inputs to NOR gate 190A are coupled to the temporary REFRACTORY signal, the temporary SENSITIVITY signal and the temporary R-SYNCHRONOUS signals provided from parameter decode logic 138 through inverters included in memory 140.

In operation, when reed switch 46 is in its normally opened position, the output of NOR gate 190A is a logic "0" and maintains NOR gate 170M in reversion and sense reset logic 170 enabled. When reed switch 46 becomes closed and latch 159A set, causing the Q̄ output thereof to become logic "0", NOR gate 190A provides a logic "1" signal if all of the other signals applied thereto are a logic "0". This would normally be the case, unless one of the REFRACTORY, SENSITIVITY or R-SYNCHRONOUS parameters are being programmed in the temporary mode, so as to cause the temporary REFRACTORY, temporary SENSIVITY and temporary R-SYNC signals to become logic "1". Also, if the temporary DEMAND parameter is being programmed and the eighth data bit is a logic "0" indicating the DEMAND mode, NOR gate 190B will provide a logic "1" signal, and hence the output of NOR gate 190A will be logic "0". Finally, if the permanent DEMAND parameter is being programmed and the eighth data bit is a logic "0", indicating a demand mode, latch 190C will be reset, causing the Q̄ output thereof to become logic "1", which in turn causes the output of NOR gate 190A to become logic "0".

It should be noted that the programming of the permanent demand feature is in fact only a semi-permanent situation in that it only lasts as long as the reed switch is closed, whereas the permanent programming of other parameters lasts until they are subsequently changed.

Referring now to reed switch logic 159 shown in FIG. 6M, there is included latch 159A and inverter 159B. The reed switch signal which is normally a logic "0" when reed switch 46 is open and a logic "1" when reed switch 46 is closed, is applied to the data input of latch 159A and through inverter 159B to the reset input of latch 159A. The clock input to reed switch logic 159A is coupled to the output of inverter 169F in blank logic 169. Thus reed switch latch 159A is clocked each time a stimulating pulse is to be provided or a natural heartbeat is detected. If reed switch 46 is closed, latch 159A is clocked into a set condition, causing the Q output thereof to become logic "1" and the Q̄ output thereof to become logic "0", and if reed switch 46 is open, latch 159A is reset immediately through inverter 159B.

What is claimed is:

1. A digitally controlled cardiac pacemaker pulse generator powered by an electrical power source for providing cardiac stimulating pulses at a defined rate and at a defined pulse width, said pulse generator comprising:
   clock means for providing a series of clock pulses;
   a resettable first counter for counting clock pulses applied thereto;
   means for coupling said series of clock pulses to said first counter;
   a second counter for counting pulses applied thereto;
   counter interface means responsive to said first counter for providing a counting pulse to said second counter each time said first counter reaches a first count and for resetting said first counter;
   rate decoding means responsive to the count of said second counter reaching a defined value for providing a signal manifesting that a cardiac stimulating pulse is to be provided;
   pulse width decoding means responsive to said rate decoding means signal and the count of said first counter reaching a defined value for providing a signal manifesting the desired pulse width of said cardiac stimulating pulse; and
   output means responsive to said rate decoding means signal and said pulse width decoding means signal for providing said cardiac stimulating pulse.

2. The invention according to claim 1 wherein said pulse generator further comprises:
   a depletion sensing circuit for providing a control signal whenever said power source energy depletes to a predetermined value; and
   wherein said counter interface means responds to said control signal and said first counter reaching a second count instead of said first count whenever said control signal is provided for providing said counting pulse to said second counter and for resetting said first counter, thereby changing the rate at which said stimulating pulses are generated.

3. The invention according to claim 2 wherein said counter interface means includes gate means responsive to said control signal and the first and second counts of said first counter for providing a signal to cause said counting pulse to be provided.

4. The invention according to claim 1:
wherein said first counter includes a series of resettable bistable circuits coupled as a binary counter, said clock signal being applied to the first of said series of bistable circuits; and
wherein said counter interface means responds to the last of said series of bistable circuits being triggered to another state for providing a pulse to said second counter and resetting each of said series of bistable circuits.

5. The invention according to claim 4 wherein said pulse generator further comprises:
a depletion sensing circuit for providing a control signal of a certain value whenever said power source energy depletes to a predetermined value; and
wherein said counter interface means responds to only the last one of said series of bistable circuits being triggered to another state when said control signal is not provided at said certain value, and further responds to the last and to certain other ones of said series of bistable circuits being triggered to another state whenever said control signal is at said certain value for providing said pulse to said second counter and resetting each of said series of bistable circuits.

6. The invention according to claim 5 wherein said counter interface means includes first and second gate circuits, said first gate circuit being responsive to said certain other ones of said series of bistable circuits being triggered and to said control signal for providing an enable signal whenever either said control signal is not at said certain value or each of said certain other ones of said bistable circuits are triggered and said control signal is at said certain value, said second gate circuit responding to the simultaneous occurrence of said enable signal and said last one of said series of bistable circuits being triggered to said other state for providing a signal to cause said pulse to be provided to said second counter and to reset each of said bistable circuits.

7. The invention according to claim 6 wherein said output means includes additional bistable means having an output which changes from one state to another in response to said rate decoding signal and which changes back to said one state in response to said pulse width decoding signal.

8. The invention according to claim 7 wherein said additional bistable means includes logic means responsive to said rate decoding signal, said pulse width decoding signal and said clock pulses for synchronizing said additional bistable means change of states with the occurrence of said clock pulses.

9. The invention according to claim 8 wherein said counter interface means responds to said additional bistable means by providing additional pulses to reset said first counter each time said additional bistable means changes states.

10. The invention according to claim 9 wherein said additional bistable means includes means to reset said second counter to an initial value each time said additional bistable means changes from said other state to said one state.

11. The invention according to claim 1 wherein said output means includes bistable means having an output which changes from one state to another in response to said rate decoding signal and which changes back to said one state in response to said pulse width decoding signal.

12. The invention according to claim 11 wherein said bistable means includes logic means responsive to said rate decoding signal, said pulse width decoding signal and said clock pulses for synchronizing said bistable means change of states with the occurrence of said clock pulses.

13. The invention according to claim 12 wherein said pulse generator further comprises:
a depletion sensing circuit for providing a control signal whenever said power source energy depletes to a predetermined value; and
wherein said counter interface means responds to said control signal and said first counter reaching a second count instead of said first count whenever said control signal is provided for providing said counting pulse to said second counter and for resetting said first counter, thereby changing the rate at which said stimulating pulses are generated.

14. The invention according to claim 13 wherein said counter interface means includes gate means responsive to said control signal and the first and second counts of said first counter for providing a signal to cause said counting pulse to be provided.

* * * * *